US009637526B2

(12) United States Patent
Sentissi et al.

(10) Patent No.: US 9,637,526 B2
(45) Date of Patent: May 2, 2017

(54) CHLOROTOXIN POLYPEPTIDES AND CONJUGATES AND USES THEREOF

(71) Applicant: MORPHOTEK, INC., Exton, PA (US)

(72) Inventors: Abdellah Sentissi, Dover, MA (US); Douglas B. Jacoby, Wellesley, MA (US)

(73) Assignee: Morphotek, Inc., Exton, PA (US)

( * ) Notice: Subject to any disclaimer, the term of this patent is extended or adjusted under 35 U.S.C. 154(b) by 0 days.

(21) Appl. No.: 14/956,261

(22) Filed: Dec. 1, 2015

(65) Prior Publication Data

US 2016/0152671 A1 Jun. 2, 2016

Related U.S. Application Data

(60) Division of application No. 14/450,182, filed on Aug. 1, 2014, now Pat. No. 9,234,015, which is a continuation of application No. 13/577,169, filed as application No. PCT/US2011/023823 on Feb. 4, 2011, now Pat. No. 9,018,347.

(60) Provisional application No. 61/301,615, filed on Feb. 4, 2010.

(51) Int. Cl.
A61K 47/48 (2006.01)
C07K 14/435 (2006.01)
A61K 38/00 (2006.01)
G01N 33/574 (2006.01)
A61K 31/337 (2006.01)
A61K 51/08 (2006.01)
A61K 31/7068 (2006.01)

(52) U.S. Cl.
CPC ...... C07K 14/43522 (2013.01); A61K 31/337 (2013.01); A61K 31/7068 (2013.01); A61K 47/48215 (2013.01); A61K 47/48261 (2013.01); A61K 51/088 (2013.01); G01N 33/57415 (2013.01); G01N 33/57434 (2013.01); A61K 38/00 (2013.01)

(58) Field of Classification Search
CPC .............. A61K 38/00; A61K 47/48215; A61K 31/337; A61K 51/088; A61K 31/7068; A61K 47/48261; C07K 14/43522; G01N 33/57434; G01N 33/57415
See application file for complete search history.

(56) References Cited

U.S. PATENT DOCUMENTS

| | | | |
|---|---|---|---|
| 4,444,744 A | 4/1984 | Goldenberg |
| 5,051,364 A | 9/1991 | Isacke et al. |
| 5,212,290 A | 5/1993 | Vogelstein et al. |
| 5,223,253 A | 6/1993 | Hall et al. |
| 5,236,844 A | 8/1993 | Basset et al. |
| 5,314,992 A | 5/1994 | Guyre et al. |
| 5,591,829 A | 1/1997 | Matsushita |
| 5,626,862 A | 5/1997 | Brem et al. |
| 5,688,773 A | 11/1997 | Chiocca et al. |
| 5,750,376 A | 5/1998 | Weiss et al. |
| 5,756,340 A | 5/1998 | Hammock et al. |
| 5,866,570 A | 2/1999 | Liang et al. |
| 5,905,027 A | 5/1999 | Ullrich et al. |
| 5,935,795 A | 8/1999 | Lin et al. |
| 5,985,822 A | 11/1999 | Edelman et al. |
| 6,028,174 A | 2/2000 | Ullrich et al. |
| 6,130,101 A | 10/2000 | Mao et al. |
| 6,319,891 B1 | 11/2001 | Sontheimer et al. |
| 6,429,187 B1 | 8/2002 | Sontheimer et al. |
| 6,514,481 B1 | 2/2003 | Prasad et al. |
| 6,555,652 B1 | 4/2003 | Itoh et al. |
| 6,667,156 B2 | 12/2003 | Lyons et al. |
| 6,767,635 B1 | 7/2004 | Bahr et al. |
| 6,849,714 B1 | 2/2005 | Bridon et al. |
| 6,870,029 B2 | 3/2005 | Sontheimer et al. |
| 6,926,896 B2 | 8/2005 | Bosslet et al. |
| 6,972,326 B2 | 12/2005 | Haugland et al. |
| 7,094,868 B2 | 8/2006 | Samoylova et al. |
| 7,252,998 B2 | 8/2007 | Skerra et al. |
| 7,462,446 B2 | 12/2008 | Zhang et al. |
| 7,678,759 B2 | 3/2010 | Sontheimer et al. |
| 8,227,439 B2 | 7/2012 | O'Neill et al. |
| 8,470,607 B2 | 6/2013 | Jacoby et al. |
| 8,778,310 B2 | 7/2014 | Zhang et al. |
| 9,023,595 B2 | 5/2015 | O'Neill et al. |
| 9,234,015 B2 | 1/2016 | Sentissi et al. |
| 2001/0007025 A1 | 7/2001 | Bennett et al. |
| 2001/0055751 A1 | 12/2001 | Reiter et al. |
| 2002/0065216 A1 | 5/2002 | Sontheimer et al. |
| 2002/0146749 A1 | 10/2002 | Lyons et al. |

(Continued)

FOREIGN PATENT DOCUMENTS

| | | |
|---|---|---|
| CN | 1924006 A | 3/2007 |
| CN | 101003788 A | 7/2007 |

(Continued)

OTHER PUBLICATIONS

Adelstein, S.J. et al., Radiotoxicity of iodine-125 and other auger-electron-emitting radionuclides: background to therapy, Cancer Biotherapy and Radiopharmaceuticals, 18(3):301-16 (2003).
Akabani et al., Dosimetry and Radiographic Analysis of 131 I-Labeled Anti-Tenascin 81 C6 Murine Monoclonal Antibody in Newly Diagnosed Patients with Malignant Gliomas: A Phase II Study, Journal of Nuclear Medicine, 46(6):1042-1051 (2005).
Akabani et al., Dosimetry of 131 I-Labeled 81C6 Monoclonal Antibody Administered into Sugically Created Resection Cavities in Patients with Malignant Brain Tumors, J of Nucl. Med., 40:631-638 (1999).
Akcan, M. et al., Chemical Re-engineering of Chlorotoxin Improves Bioconjugation Properties for Tumor Imaging and Targeted Therapy, J. of Medicinal Chem., 54(3):782-7 (2011).

(Continued)

Primary Examiner — Julie Ha
Assistant Examiner — Li Ni Komatsu
(74) Attorney, Agent, or Firm — Brenda Herschbach Jarrell; Choate, Hall & Stewart LLP

(57) ABSTRACT

Reduced lysine chlorotoxin polypeptides that may be used to generate single species conjugates of chlorotoxin. Conjugates comprising such chlorotoxin polypeptides and pharmaceutical compositions thereof. Methods of using such compositions and/or conjugates.

72 Claims, No Drawings

(56) References Cited

U.S. PATENT DOCUMENTS

| | | |
|---|---|---|
| 2003/0021810 A1 | 1/2003 | Sontheimer et al. |
| 2003/0201208 A1 | 10/2003 | Koch et al. |
| 2003/0216322 A1 | 11/2003 | Samoylova et al. |
| 2003/0232013 A1 | 12/2003 | Sieckman et al. |
| 2004/0101822 A1 | 5/2004 | Wiesner et al. |
| 2004/0102381 A1 | 5/2004 | Ekwuribe et al. |
| 2004/0105980 A1 | 6/2004 | Sudarshan et al. |
| 2004/0141981 A1 | 7/2004 | Sontheimer et al. |
| 2004/0180846 A1 | 9/2004 | Huang et al. |
| 2005/0142062 A1 | 6/2005 | Sontheimer et al. |
| 2005/0261191 A1 | 11/2005 | Barasch et al. |
| 2006/0019256 A1 | 1/2006 | Clarke et al. |
| 2006/0019347 A1 | 1/2006 | Cho et al. |
| 2006/0088899 A1 | 4/2006 | Alvarez et al. |
| 2006/0166892 A1 | 7/2006 | Alvarez et al. |
| 2007/0071764 A1 | 3/2007 | Sullivan et al. |
| 2007/0154965 A1 | 7/2007 | Zhang et al. |
| 2007/0237714 A1 | 10/2007 | Alvarez |
| 2007/0275902 A1 | 11/2007 | Gonda et al. |
| 2008/0153745 A1 | 6/2008 | Tian |
| 2008/0153746 A1 | 6/2008 | Alvarez et al. |
| 2008/0279780 A1 | 11/2008 | Zhang et al. |
| 2009/0004105 A1 | 1/2009 | Cheng et al. |
| 2009/0123946 A1 | 5/2009 | Birkenmeyer et al. |
| 2009/0123970 A1 | 5/2009 | Tu et al. |
| 2009/0124022 A1 | 5/2009 | Birkenmeyer et al. |
| 2009/0176274 A1 | 7/2009 | Tu et al. |
| 2009/0203598 A1 | 8/2009 | McCarty et al. |
| 2009/0263894 A1 | 10/2009 | Birkenmeyer et al. |
| 2009/0269777 A1 | 10/2009 | Birkenmeyer et al. |
| 2009/0304592 A1 | 12/2009 | O'Neill et al. |
| 2009/0311224 A1 | 12/2009 | Lee et al. |
| 2010/0098637 A1 | 4/2010 | Orringer et al. |
| 2010/0105150 A1 | 4/2010 | Adamczyk et al. |
| 2010/0210546 A1 | 8/2010 | Alvarez et al. |
| 2010/0215575 A1 | 8/2010 | O'Neill et al. |
| 2010/0215576 A1 | 8/2010 | Sontheimer et al. |
| 2011/0027177 A1 | 2/2011 | Jacoby et al. |
| 2011/0091380 A1 | 4/2011 | Jacoby et al. |
| 2011/0311445 A1 | 12/2011 | Alvarez et al. |
| 2012/0156131 A1 | 6/2012 | Alvarez |
| 2012/0183544 A1 | 7/2012 | Sontheimer et al. |
| 2013/0028836 A1 | 1/2013 | Sentissi et al. |
| 2013/0045163 A1 | 2/2013 | O'Neill et al. |
| 2013/0195760 A1 | 8/2013 | Olson |
| 2014/0241993 A1 | 8/2014 | Zhang et al. |
| 2015/0010473 A1 | 1/2015 | Alvarez |

FOREIGN PATENT DOCUMENTS

| | | |
|---|---|---|
| CN | 101270158 A | 9/2008 |
| CN | 101381405 A | 3/2009 |
| CN | 101824084 A | 9/2010 |
| CN | 101921769 A | 12/2010 |
| EP | 0155396 A2 | 9/1985 |
| EP | 1430131 A2 | 6/2004 |
| EP | 2182004 A1 | 5/2010 |
| JP | H08-325291 A | 12/1996 |
| JP | H09-071599 A2 | 3/1997 |
| WO | WO-88/02117 A1 | 3/1988 |
| WO | WO-93/11222 A1 | 6/1993 |
| WO | WO-94/15615 A1 | 7/1994 |
| WO | WO-97/24619 A1 | 7/1997 |
| WO | WO-99/29715 A1 | 6/1999 |
| WO | WO-00/62807 A1 | 10/2000 |
| WO | WO-00/62810 A1 | 10/2000 |
| WO | WO-03/000203 A2 | 1/2003 |
| WO | WO-03/008583 A2 | 1/2003 |
| WO | WO-03/101474 A1 | 12/2003 |
| WO | WO-03/101475 A1 | 12/2003 |
| WO | WO-2005/002604 A1 | 1/2005 |
| WO | WO-2005/053611 A2 | 5/2005 |
| WO | WO-2005/099774 A2 | 10/2005 |
| WO | WO-2005/107793 A2 | 11/2005 |
| WO | WO-2006/040574 A2 | 4/2006 |
| WO | WO-2006/095164 A1 | 9/2006 |
| WO | WO-2006/110581 A2 | 10/2006 |
| WO | WO-2006/110582 A1 | 10/2006 |
| WO | WO-2006/116156 A2 | 11/2006 |
| WO | WO-2006/115633 A2 | 12/2006 |
| WO | WO-2007/044994 A2 | 4/2007 |
| WO | WO-2007/047458 A2 | 4/2007 |
| WO | WO-2007/117467 A2 | 10/2007 |
| WO | WO-2007/137163 A2 | 11/2007 |
| WO | WO-2008/088422 A2 | 7/2008 |
| WO | WO-2008/155134 A1 | 12/2008 |
| WO | WO-2009/021136 A1 | 2/2009 |
| WO | WO-2009/049184 A2 | 4/2009 |
| WO | WO-2009/052390 A1 | 4/2009 |
| WO | WO-2009/052392 A1 | 4/2009 |
| WO | WO-2009/052400 A1 | 4/2009 |
| WO | WO-2009/062520 A1 | 5/2009 |
| WO | WO-2009/140599 | 6/2009 |
| WO | WO-2009/108762 A2 | 9/2009 |
| WO | WO-2009/117018 A1 | 9/2009 |
| WO | WO-2009/156456 A1 | 12/2009 |
| WO | WO-2011/057295 A2 | 5/2011 |
| WO | WO-2011/094671 A2 | 8/2011 |
| WO | WO-2011/097533 A1 | 8/2011 |
| WO | WO-2011/142858 A2 | 11/2011 |
| WO | WO-2012/022742 A1 | 2/2012 |

OTHER PUBLICATIONS

Amersham Biosciences Publication, Labelling of Proteins with CyOye N-hydroxysuccinimide Esters for Fluorescent Applications on the LEAOSeeker Homogeneous Imaging System, Leadseeker L8:1-4, (2001).

AnaSpec Database, Chlorotoxin (Cltx), A 36-amino acid Cl-channel blocker from Leiurus quinquestriatus scorpion venom, Catalog #AS-60770, 1 page, retrieved from the internet: http://www.anaspec.com/products/product.asp?id=30976 (last accessed Oct. 8, 2014).

Applebaum et al., Treatment Of Malignant Lymphoma In 100 Patients With Chemotherapy, Total Body Irradiation, And Marrow Transplantation, J. Clin. Oncol., 5:1340-1341 (1987).

Author Not Known, CyDye™ mono-reactive NHS-Esters, Amersham Biosciences, pp. 1-20 (2002).

Baker, Effects of an epithelial Cl channel blocker on whole cell voltage clamp and patch clamp recordings from a human astrocytoma in culture, J. Physiol. 438:128-129 (1991).

Banks, W.A. et al., Delta sleep-inducing peptide crosses the blood-brain-barrier in dogs: some correlations with protein binding, Pharmacol. Biochem. Behav., 17(5):1009-14 (1982).

Berendsen, Herman JC, A Glimpse of the Holy Grail?, Science, 282:642-643 (1998).

Berlier, J. E. et al., Quantitative comparison of long-wavelength Alexa Fluor dyes to Cy dyes: fluorescence of the dyes and their bioconjugates, J Histochem Cytochem, 51(12):1699-712 (2003).

Bertolini et al., Inhibition of angiogenesis and induction of endothelial and tumor cell apoptosis by green tea in animal models of human high-grade non-Hodgkin's lymphoma, Leukemia, 14:1477-1482 (2000).

Binger et al., Iodine-131-Labeled Antitenasein Monoclonal Antibody 81C6 Treatment of Patients with Recurrent Malignant Gliomas: Phase I Trial Results Journal of Clinical Oncology, 16(6): 2202-2212 (1998).

Bodey et al., Failure of Cancer Vaccines: The Significant Limitations of this Approach to Immunotherapy, Anticancer Res., 20: 2665-2667 (2000).

Bowie et al., Deciphering the Message in Protein Sequences: Tolerance to Amino Acid Substitutions, Science, 257:1306-1310 (1990).

Bradley and Barrick, Limits of Cooperativity in a Structurally Modular Protein: Response of the Notch Ankyrin Domain to Analogous Alanine Substitutions in Each Repeat, J. Mol. Biol. 324:373-386 (2002).

Brem et al., Placebo-controlled trial of safety and efficacy of intraoperative controlled delivery by biodegradable polymers of chemotherapy for recurrent gliomas, The Lancet, 345:1008-1012 (1995).

(56) References Cited

OTHER PUBLICATIONS

Brismar, T. and Collins, V., Inward rectifying potassium channels in human malignant glioma cells, Brain Res. 480:249-258 (1989).
Brismar, T. and Collins, V., Potassium and sodium channels in human malignant glioma cells, Brain Res. 480:259-267 (1989).
Britton et al, Prostate cancer: the contribution of nuclear medicine, BJU Int'l 86(1):135-142 (2000).
Burger et al., Topographic anatomy and CT correlations in the untreated glioblastoma multiforme, J. Neurosurg, 68:698-704 (1988).
Burgess et al., Possible Dissociation of the Heparin-binding and Mitogenic Activities of Herparin-binding (Acidic Fibroblast) Growth Factor-1 from Its Receptor-binding Activities by Site-directed Mutagenesis of a Single Lysine Residue, J Cell Biol, 111:2129-2138 (1990).
Buskens et al., Adenocarcinomas of the Gastro-Esophageal Junction: A Comparative Study of the Gastric Cardia and the Esophagus with Respect to Cyclooxygenase-2 Expression, Digestive Disease Week Abstracts and Itinerary Planner (2003) Abstract 850.
Butterworth, M. D. et al., Preparation of Ultrafine Silica-and PEG-Coated Megnetite Particles, Colloids and Surfaces A: Physiochemical and Engineering Aspects 179:93-102 (2001).
Castro, M.G. et al., Gene therapy for Parkinson's disease: recent achievements and remaining challenges, Histl. Histopathol. 16(4):1225-1238 (2001).
Chien et al., The two-hybrid system: A method to identify and clone genes for proteins that interact with a protein of interest, Proc. Natl. Acad. Sci. USA, 88:9578-9582 (1991).
Chiu, S. and Wilson G., The role of potassium channels in Schwann cell proliferation in Wallerian degeneration of explant rabbit sciatic nerves, J. Physiol. 408:199-222 (1989).
Chuthapisith et al. Annexins in human breast cancer: possible predictors of pathological response to neoadjuvant chemotherapy, European J of Cancer, 45:1274-81 (2009).
Citrin, D. et al., In vivo tumor imaging in mice with near-infrared labeled endostatin, Mol Cancer Ther, 3(4):481-8 (2004).
Communication pursuant to Article 94(3) EPC for European Application 09 150 772.3, 15 pages (Feb. 14, 2012).
Daly et al, Pumiliotoxin alkaloids: a new class of sodium channel agents, Biochem Pharmacol., 40(2):315-326 (1990), Abstract only.
Davis, C. G., The many faces of epidermal growth factor repeats, The New Biologist, 2(5):410-419 (1990).
De Muralt, B. et al., Reactivity of antiglioma monoclonal antibodies for a large panel of cultured gliomas and other neuroectoderm derived tumors, Anticancer Res. 3:1-6 (1983).
Deane, K. and Mannie, M., An alternative pathway of B cell activation: stilbene disulfonates interact with a Cl binding motif on AEn-related proteins to stimulate motogenesis, Eur. J. Immunol. 22:1165-1171 (1992).
Debin, J. et al., Purification and characterization of chlorotoxin, a chloride channel ligand from the venom of the scorpion, Am. J. Physiol. 264:C361-369 (1993).
Debin, J.A. and Strichartz, G.R., Chloride channel inhibition by the venom of the scorpion Leiurus quinquestriatus, Toxicon. 29:1403-1408 (1991).
Definition of 'same' retrieved from http://dictionary.reference.com/browse/same on Jun. 20, 2012 4 pages.
Dermer, G.B., Another Anniversary for the War on Cancer, Bio/Technology, 12:320 (1994).
Deshane et al., Chlorotoxin inhibits glioma cell invasion via matrix metalloproteinase-2, Journal of Biological Chemistry 278(6):4135-4144 (2002).
Drexler, Recent Results on the Biology of Hodgkin and Reed-Sternberg cells, Leukemia and Lymphoma, 9:1-25 (1993).
Eck, S. and Wilson, J., Goodman & Gilman's The Pharmacological Basis of Therapeutics, McGraw-Hill, New York, p. 77-101 (1996).
Egleton, R.D. and Davis T.P., Development of neuropeptide drugs that cross the blood-brain barrier, NeuroRx, 2(1):44-53 (2005).
Entrez Gene entry for ANXA 2 annexin A2, updated Aug. 26, 2010, downloaded from http://ncbi.nlm.nih.gov/gene/302.
Epstein et al., Morphological and Virological Investigations On Cultured Burkitt Tumor Lymphoblasts (Strain Raji), J. Natl. Cancer Inst., 37:547-559 (1966).
European Partial Search Report for EP10178613.5, 9 pages (Feb. 15, 2012).
European Search Report for EP09150772.3, 15 pages (Feb. 14, 2012).
Evans et al., Design of Nonpeptidal Ligands for a Peptide Receptor: Cholecystokinin Antagonists, J. Med. Chem., 30:1229-1239 (1987).
Examination Report for AU2008310664, 3 pages (Feb. 11, 2013).
Examination Report for EP08837002.8, 7 pages (Feb. 11, 2013).
Examination Report for European Application 09 747 680.8, 6 pages (May 22, 2014).
Extended European Search Report for 08873442.1, 9 pages (May 20, 2015).
Extended European Search Report for EP 11740464.0, 10 pages (Jul. 2, 2013).
Extended European Search Report for EP08837002.8, 9 pages (Nov. 23, 2010).
Extended European Search Report for EP09150772.3, 18 pages (Jul. 30, 2010).
Extended European Search Report for EP10178613, 26 pages (Jun. 4, 2012).
Extended European Search Report for European Application 09 176 234.4, 9 pages (Apr. 6, 2010).
Extended European Search Report for European Application 11 780 950.9 (Oct. 15, 2013).
Fauchere, Elements for the rational design of peptide drugs, Adv. Drug Res., 15:29-69 (1986).
Field and Song, A novel genetic system to detect protein-protein interactions, Nature, 340:245-246 (1989).
Fiveash et al, Tumor Specific Targeting of Intravenous <131>I-chlorotoxin (TM-601) in Patients With Recurrent Glioma, Int'l J of Radiation: Oncol. Biol. Physics 69(3):S257-S258 (2007).
Fiveash et al., Safety and Tolerance of Multiple Weekly of Intracavitary Injections of 131I-chlorotoxin (TM-601): Preliminary result of a prospective clinical trial in patients with recurrent gliobastoma multiforme, J. Clin. Oncol., ASCO Annual Meeting Proceedings Part I, 24(18S): Abstract 1555 (2006).
Free Dictionary citing American Heritage Medical Dictionary, 1 page (2007).
Freshney, Culture of Animal Cells, A Manual of Basic Technique, Alan R. Liss, Inc., 4 (1983).
Friedman, H. et al., Temozolomide and Treatment of Malignant Glioma1, Clinical Cancer Res., 6:2585-2597 (2000).
Goldstein, G. and Betz, A., The Blood Brain Barrier, Sci. Am. 255:74-83 (1986).
Gorecki, D.C., Prospects and problems of gene therapy: an update, Expert Opin. Emerging Drugs 6(2):187-198 (2001).
Gorman et al., The Hype and the Hope, Time, 151(19): 40-44 *1998).
Gray, P.T.A. and Ritchie, J.M., A voltage-gated chloride conductance in rat cultured astrocytes, Proc. R. Soc. Land. 228:267-288 (1986).
Grimes et al., TM-601 targets human cancer cells via a phosphatidylinositol phosphate in lamellipodia, J. Clin. Oncol., ASCO Annual Meeting Proceedings Part I, Abstract 9556 (2005).
Grissmer, S. et al., Calcium-activated potassium channels in resting and activated human T lymphocytes, J. Gen. Phys. 102(4):601-630 (1993).
Grossman and Batara, Current management of glioblastoma multiforme, Semin. Oncol., 31:635-644 (2004).
Gura, T., Systems for Identifying New Drugs are Often Faulty, Sci., 278:1041-1042 (1997).
Hajjar, K.A. and Krishnan, S., "Annexin II: A Mediator of the Plasmin/Plasminogen Activator System," Trends in Cardiovascular Medicine 9(5):128-138 (1999).
Hamman, J.H. et al., Oral delivery of peptide drugs: barriers and developments, Biodrugs 19(3):165-177 (2005).
Hartwell et al., Integrating Genetic Approaches into the Discovery of Anticancer Drugs, Science, 278:1064-1068 (1997).
Hockaday, D. et al., Imaging Glioma Extent with 131 1-TM-601, J. Nucl. Med. 46(4):580-586 (2005).

(56) References Cited

OTHER PUBLICATIONS

Holmes, K. and Lantz, L., Protein Labeling with Fluorescent Probes, Methods in Cell Biology 63:185-204 (2001).
Hosli, E and Hosli, L., Evidence for GABA-B receptors on cultured astrocytes of rat CNS: autoradiographic binding studies, Exp. Brain. Res. 80:621-625 (1990).
Huang, Y. and Rane S., Potassium channel induction by the Ras/Raf signal transduction cascade, J. Biol. Chem. 269(49):31183-31189 (1994).
Huys, I. et al., Structure-function study of a chlorotoxin-chimer and its activity on Kv1.3 channels, J Chromatogr B Analyt Technol Biomed Life Sci, 803(1):67-73 (2004).
International Preliminary Report on Patentability for PCT/US04/39325, 4 pages (May 29, 2006).
International Preliminary Report on Patentability for PCT/US05/011523, 7 pages (Oct. 11, 2006).
International Preliminary Report on Patentability for PCT/US2007/008309, 9 pages (Sep. 30, 2008).
International Preliminary Report on Patentability for PCT/US2008/076740, 7 pages (Sep. 30, 2010).
International Preliminary Report on Patentability for PCT/US2008/079547, 4 pages (Apr. 13, 2010).
International Preliminary Report on Patentability for PCT/US2009/044149, 5 pages (Nov. 25, 2010).
International Preliminary Report on Patentability for PCT/US2011/023797, 6 pages (Nov. 13, 2012).
International Preliminary Report on Patentability for PCT/US2011/023823, 8 pages (Aug. 16, 2012).
International Search Report for PCT/US00/10453, Jun. 30, 2000.
International Search Report for PCT/US03/17410, 4 pages (Nov. 13, 2003).
International Search Report for PCT/US04/39325, 2 pages (Mar. 27, 2006).
International Search Report for PCT/US05/11523, 3 pages (Feb. 9, 2006).
International Search Report for PCT/US2006/010170, 5 pages (Oct. 6, 2006).
International Search Report for PCT/US2007/008309, 4 pages (Nov. 20, 2007).
International Search Report for PCT/US2008/076740, 3 pages (Jan. 1, 2009).
International Search Report for PCT/US2009/044149, 4 pages (Oct. 19, 2009).
International Search Report for PCT/US2011/023797, 6 pages (Nov. 18, 2011).
International Search Report for PCT/US2011/023823, 3 pages (Apr. 25, 2011).
International Search Report for PCT/US2013/074215 (Apr. 8, 2014).
Jacoby, D. et al., Potent Pleiotropic Anti-Angiogenic Effects of TM601, a Synthetic Chlorotoxin Peptide, Anticancer Res. 30:39-46 (2010).
Jalonen, T., Single-channel characteristics of the large-conductance anion channel in rat cortical astrocytes in primary culture, Glia 9:227-237 (1993).
Jiang, T. et al., Tumor imaging by means of proteolytic activation of cell-penetrating peptides, Proc Natl Acad Sci, U S A, 101(51):17867-72 (2004).
Kaiser, First Pass at Cancer Genome Reveals Complex Landscape, Science, 313:1370 (2006).
Kastin, A.J. and Akerstrom V., Orexin A but not orexin B rapidly enters brain from blood by simple diffusion, J. Pharmacol. Exp. Ther., 289(1):219-23 (1999).
Kaye, F.J. et al., A single amino acid substitution results in a retinoblastoma protein defective in phosphorylation and oncoprotein binding, Proc. Natl. Acad. Sci. USA 87(17):6922-6926 (1990).
Kesavan, K. et al., "Annexin A2 is a Molecular Target for TM601, a Peptide with Tumor-Tarqetinq and Anti-anqioqenic Effects," Journal of Bioloqical Chemistry 285(7):4366-4374 (2010).

Kessler, R. et al., "Identification of the Putative Brain Tumor Antigen BF7/GE2 as the (De)Toxifying Enzyme Microsomal Epoxide Hydrolase." Published by the American Association for Cancer Research, Philadelphia. PA, Cancer Research 60:1403-1409 (2000).
Kimura, R. et al., A Dual-Labeled Knottin Peptide for PET and Near-Infrared Fluorescence Imaging of Integrin Expression in Living Subjects, Bioconjugage Chem. 21(3):436-444 (2010).
Kirkin et al., Melanoma-associated antigens recognized by cytotoxic T lymphocytes, APMIS, 106: 665-679 (1998).
Klein et al., Surface Igm-Kappa Specificity On A Burkitt Lymphoma Cell In Vivo And In Derived Culture Lines, Cancer Res., 28:1300-1310 (1968).
Kohler, N. A bifunctional poly(ethylene glycol) silane immobilized on metallic oxide-based nanoparticles for conjugation with cell targeting agents, J Am Chem Soc, 126(23):7206-11 (2004).
Kuan et al., EGFRvIII as a promising target for antibody-based brain tumor therapy, Brain Tumor Pathol., 17:71-78 (2000).
Kunwar, S. et al., Cytotoxicity and antitumor effects of growth factor-toxin fusion proteins on human glioblastoma multiforme cells, J. Neurosurg. 79(4):569-576 (1993).
Laumonnier et al., Identification of the annexin A2 heterotetramer as a receptor for the plasmin-induced signaling in human peripheral monocytes, Blood, 107:3342-3349 (2006).
Lazar et al., Transforming Growth Factor ?: Mutation of Aspartic Acid 47 and Leucine 48 Results in Different Biological Activities, Mol Cell Biol, 8:1247-1252 (1998).
Lee et al., Increased Vaccine-Specific T Cell Frequiency After Peptide-Based Vaccination Correlates with Increased Susceptibility to In Vitro Stimulation But Does Not Lead to Tumor Regression ,J. Immunol, 163: 6292-6300 (1999).
Lee, M.J. et al., Rapid pharmacokinetic and biodistribution studies using cholorotoxin-conjugated iron oxide nanoparticles: a novel non-radioactive method, PLoS One, 5(3):e9536 (2010).
Levin, V.A., The place of hydroxyurea in the treatment of primary brain tumors, Database accession No. NLM1641655 (abstract), Seminars in Oncology, 19(3):34-39 (1992), Abstract only.
Lippens et al., NMR Sequencial Assignments and Solution Structure of Chlorotoxin, a Small scorpion Toxin that Blocks Chloride Channels, Biochemistry 34(1):13-21 (1995).
Lokman et al., The role of annexin A2 in tumorigenesis and cancer progression, Cancer Microenvironment, published online Mar. 5, 2001, DOI 10.1007/s12307-011-0064-9 (2011).
Lynch, Chemoprevention with Special reference to inherited colorectal cancer, Familial Cancer, 7:59-64 (2008).
Lyons, S. et al., Chlorotoxin, a Scorpion-Derived Peptide, Spcifically Binds to Gliomas and Tumors of Neuroectodermal Origin, GLIA 39:162-173 (2002).
Malinowska, D.H. et al., Recombinant chlorotoxin: An inhibitor of gastric C1-channels, Biophysical Journal, 66(2):A100 (1994).
Mamelak et al, PhaseI/II Trial of Intracavitary 131I-TM-601 in Adult Patients with Recurrent High-Grade Glioma, Neuro-Oncology online, 5:340 (2003).
Mamelak, A. and Jacoby, D., Targeted Delivery of Antitumoral Therapy to Glioma and Other Malignancies with Synthetic Chlorotoxin (TM-601 ), Expert Opin. Drug Delivery 4(2):175-186 (2007).
Mamelak, A. et al., Phase I Single-Dose Study of Intracavitary-Administered Iodine-131-TM-601 in Adults With Recurrent High-Grade Glioma, J. Clinic. Oncology 24(22)3644-3650 (2006).
McFerrin and Sontheimer, A role for ion channels in glioma cell invasion, Neuron. Glia Biology, 2:39-49 (2005).
McKie, R., Cancer Research Set Back a Decade, The Observer, 1-4 (2001).
McMichael, Leukocyte Typing III, Oxford University Press, 302-363 and 432-469 (1987).
Mellman, Where Next for Cancer Immunotherapy?, The Scientist, 20(1): 47-56 (2006).
Milross et al., Relationship of Mitotic Arrest and Apoptosis to Antitumor Effect of Paclitaxel, J. Nat'l Cancer Inst., 88:1308-1314 (1996).

(56) References Cited

OTHER PUBLICATIONS

Minowada et al., Rosette-Forming Human Lymphoid Cell Lines. I. Establishment and Evidence for Origin of Thymus-Derived Lymphocytes, J. Natl. Cancer Inst., 49:891-895 (1972).
Moiety, Definition of, from http://dictionary.reference.com/browse/moiety, pp. 1-3 (last accessed Aug. 26, 2010).
Mousa, S. et al., Potent anti-angiogenesis efficacy of chlorotoxin and its synergistic interactions with Anti-VEGF targets, American Association for Cancer Research Annual Meeting Proceedings, Abstract #268 (2008).
Muro et al., Convection-Enhanced and Local Delivery of Targeted Cytotoxins in the Treatment of Malignant Gliomas, Technology in Cancer Research and Treatment, 5(3):201-213, ISSN 1533-0346 (2006).
NCI Dictionary of Cancer Terms for Non-Hodgkin Lymphoma (Apr. 30, 2012).
Newlands et al., Temozolomide: A Review of Its Discovery, Chemical Properties, Pre-clinical Development and Clinical Trials, Cancer Treatment Reviews 23(1):35-61 (1997).
Ngo et al., Computational Complexity, Protein Structure Prediction, and the Levinthal Paradox, The Protein Folding Problem and Terriary Structure Prediction, 491-494 (1994).
Nilius, B. and Wohlrab, W., Potassium channels and regulation of proliferation of human melanoma cells, J. Physiol. 445:537-548 (1992).
O'Neill et al. "Treatment of Metastatic Tumors." U.S. Appl. No. 61/053,651, filed May 15, 2008. (Not published.).
Office Action for CA2487425, 5 pages (Oct. 24, 2012).
Office Action for Canadian Application 2,487,425, 10 pages (Jan. 8, 2010).
Office Action for Chinese Application 200980123047.4, 15 pages (Jun. 12, 2014).
Office Action for CN 201180012427.8, 7 pages (Aug. 11, 2014).
Office Action for JP2011-052039 dated Feb. 18, 2014.
Office Action for U.S. Appl. No. 11/897,721, 13 pages (Sep. 15, 2009).
Office Action for U.S. Appl. No. 11/897,721, 7 pages (Mar. 24, 2010).
Pappas, C. et al., Reduction of glial proliferation by K+ channel blockers is mediated by changes in pH;, NeuroReport 6:193-196 (1994).
Pappone, P. and Ortiz-Miranda, S., Blockers of voltage-gated K channels inhibit proliferation of cultured brown fat cells, Am. J. Physiol. 264(4 Pt 1):C1014-1019 (1993).
Partial European Search Report for EP09150772.3, 8 pages (Apr. 8, 2010).
Partial European Search Report for European Application 10 178 613.5, 9 pages (Feb. 15, 2012).
Phillips, P. et al., Transforming growth factor-alpha-pseudomonas exotoxin fusion protein (TGF-alpha-PE38) treatment of subcutaneous and intracranial human glioma and medulloblastoma xenografts in athymic mice, Cancer Research 54(4):1008-1015 (1994).
PTO892, 1 page (Nov. 6, 2012).
Puro, D. et al., Retinal glial cell proliferation and ion channels: A possible link, Invest. Ophthalmol. Vis. Sci. 30(3):521-529 (1989).
Ramakrishnan et al., Targeting Tumor Vasculature Using VEGF-Toxin Conjugates, Methods in Molecular Biology 166:219-234 (2001).
Ravic, M., Intracavitary treatment of malignant gliomas: radioimmunotherapy targeting fibronectin, Acta Neurochir, Suppl 88:77-82 (2003).
Rawstron et al., Quantitation of minimal disease levels in chronic lymphocytic leukemia using a sensitive flow cytometric assay improves the prediction of outcome and can be used to optimize therapy, Blood, 98:29-35 (2001).
Reardon et al., A pilot study: 131I-antitenascin monoclonal antibody 81c6 to deliver a 44-Gy resection cavity boost, Neuro-Oncology, 10(2):182-189 (2008).
Reardon et al., Phase II Trial of Murine 131 I-Labeled Antitenascin Monoclonal Antibody 81C6 Administered Into Surgically Created Resection Cavities of Patients With Newly Diagnosed Malignant Gliomas, J of Clin. Oncol., 20(5):389-1397 (2002).
Rescher, U. and Gerke, V., "Annexins-unique membrane binding proteins with diverse functions," Journal of Cell Science, 117:2631-2639 (2004).
Ricotti et al., c-kit is expressed in soft tissue sarcoma of neuroectodermic origin and its ligand prevents apoptosis of neoplastic cells, Blood, 91:2397-2405 (1998).
Rousselle, C. et al., New advances in the transport of doxorubicin through the blood-brain barrier by a peptide vector-mediated strategy, Mol. Pharmacol., 57(4):679-86 (2000).
Rudinger, Peptide Hormones, J.A. Parsons, Ed., pp. 1-7 (1976).
Sakamoto, H. et al., Identification of a new outwardly rectifying Cl-channel that belongs to a subfamily of the CIC Cl-channels, J. Biol. Chem. 271(17):10210-10216 (1996).
Sgouros, Bone Marrow Dosimetry for Radioimmunotherapy: Theoretical Considerations, J. Nucl. Med., 34:689-694 (1993).
Sharma and Sharma, The Role of Annexin II in Angiogenesis and Tumor Progression: A Potential Therapeutic Target, Current Pharmaceutical Design, 13:3568-3575 (2007).
Shen et al., Patient-Specific Dosimetry of Pretargeted Radioimmunotherapy Using CC49 Fusion Protein in Patients with Gastrointestinal Malignancies, J. Nucl. Med., 46:642-651 (2005).
Shen et al., Practical determination of patient-specific marrow dose using radioactivity concentration in blood and body, J. Nucl. Med., 40:2102-2106 (1999).
Shen et al., Radiation dosimetry of 131I-chlorotoxin for targeted radiotherapy in glioma-bearing mice, J. Neuro-Oncol., 71:113-119 (2005).
Shen, S. et al., Dosimetry of Phase I/II Study of Intracavitary Administered I-131-TM-601 Peptide in Patients with Recurrent High-Grade Glioma, Proceedings of the 46th Annual ASTRO Meeting, S259:1 (2004).
Shiue, L. Identification of candidate genes for drug discovery by differential display, Drug Development Research, New York, 41:142-159 (1997).
Sigma, Custom Peptide Synthesis, Sigma Genosys (2004).
Silva et al., Agents that bind annexin A2 suppress ocular neovascularization, J Cell. Physiol., 225:855 (2010).
Skolnick, J. and Fetrow, J.S., From genes to protein structure and function: novel applications of computational approaches in the genomic era, Trends in Biotech 18(1):34-39 (2000).
Smith et al., Molecular Markers in Head and Neck Squamous Cell Carcinoma: Their Biological Function and Prognostic Significance, Annals Otology, Rhinology, and Laryngology, 110(3): 221-228 (2001).
Somogyi. P. et al., Subcellular localization of benzodiazepine/GABAA receptors in the cerebellum of rat, cat and monkey using monoclonal antibodies, J. Neurosci. 9(6):2197-2209 (1989).
Sontheimer, H., Voltage-dependent ion channels in glial cells, Glia 11:156-172 (1994).
Soroceanu, L. et al., Modulation of glioma cell migration and invasion using Cl(−) and K(+) ion channel blockers, J. Neuroscience 19(14):5942-5954 (1999).
Soroceanu, L. et al., Use of chlorotoxin for targeting of primary brain tumors, Cancer Research 58(21):4871-4879 (1998).
Stabin, Mirdose: Personal computer. software for internal dose assessment in nuclear. medicine, J. Nucl. Med., 37:538-546 (1996).
Steinmeyer, K. et al., Cloning and functional expression of rat CLC-5, a chloride channel related to kidney disease, J. Biol. Chem. 270(52):31172-31177 (1995).
Stewart, Chemotherapy in adult high-grade glioma: a systematic review and meta-analysis of individual patient data from 12 randomised trials, Lancet, 359:1011-1018 (2002).
Stupp et al., Current and future developments in the use of temozolomide for the treatment of brain tumors, The Lancet, 2:552-560 (2001), Abstract only.
Sun et al., In Vivo MRI Detection of Gliomas by Chlorotoxin-Conjugated Superparamagnetic Nanoprobes Small, 4(3):372-379 (2008).

(56) References Cited

OTHER PUBLICATIONS

Sun, C. et al., Tumor-targeted drug delivery and MRI contrast enhancement by chlorotoxin-conjugated iron oxide nanoparticles, NIH Public Access Author manuscript Nanomedicine, p. 1-16 (2008).
Sun, S. and Zeng, H. Size-controlled synthesis of magnetite nanoparticles, J Am Chem Soc, 124(28):8204-5 (2002).
Supplementary European Search Report for EP05763889.2, 4 pages (Sep. 24, 2007).
Supplementary Partial European Search Report for EP 00 92 6105, Mar. 11, 2003.
Supplementary Partial European Search Report for European Application 03 73 1504, 8 pages (Aug. 28, 2007).
Supplementary Partial European Search Report for European Application 08 87 3442, 4 pages (Jan. 23, 2015).
Syed et al., Angiostatin receptor annexin II in vascular tumors including angiosarcoma, Human Pathol., 38(3):508-13 (2007) Abstract.
Taber's Cyclopedic Medical Dictionary, F.A. Davis Company, Philadelphia, 274 (1985).
Tan, P. et al., Deduction of Functional Peptide Motifs in Scorpion Toxins, J. Peptide Science 12:420-427 (2006).
Tanaka et al., Redox regulation of annexin 2 and its implications for oxidative stress-induced renal carcinogenesis and metastasis, Oncogene, 23:3980-3989 (2004).
Tatenhorst, L. et al., Knockdown of annexin 2 decreases migration of human glioma cells in vitro, Neuropathology and Applied Neurobiology, 32(3):271-7 (2006).
Tatikolov, A.S. and Costa, S.M., Complexation of polymethine dyes with human serum albumin: a spectroscopic study, Biophys Chem, 107(1):33-49 (2004).
Te Velde, E.A. et al., The use of fluorescent dyes and probes in surgical oncology, Eur. J. Surg. Oncol., 36(1):6-15 (2010).
Torchilin, V.P. and Lukyanov, A.N., Peptide and protein drug delivery to and into tumors: challenges and solutions, DDT 8(6):259-266 (2003).
Transmolecular, A Phase I Imaging and Safety Study of Intravenous 131-I-TM-601 Labeled Chlorotoxin in Patients With Recurrent or Refractory Somatic and/or Cerebral Metastatic Solid Tumors, Clinical Trials NCT00379132, 3pages (Aug. 2006).
Tytgat et al., Purification and partial characterization of a "short" insectotoxin-like peptide from the venom of the scorpion Parabuthus schlechteri, FEBS, 441:387-391 (1998).
Uchida, S. et al., Localization and functional characterization of rat kidney-specific chloride channel ClC-K1, J. Clin. Invest. 95(1):104-113 (1995).
Ullrich and Sontheimer, Cell cycle-dependent expression of a glioma-specific chloride current: proposed link to cytoskeletal changes, Am. J. Physiol., 273:C1290-1297 (1997).
Ullrich, N. and Sontheimer, H., Biophysical and Pharmacological Characterization of Chloride Currents in Human Astrocytoma Cells, Am. J. Physiology 270:C1511-C1521 (1996).
Ullrich, N. et al., Expression of Voltage-Activated Chloride Currents in Acute Slices of Human Gliomas, Neuroscience 83(4):1161-1173 (1998).
Ullrich, N. et al., Human astrocytoma cells express a unique chloride current, NeuroReport 7(5):1020-1024 (1996).
UniProt Database, Accession No. P45639 (accessed 2007).
Veber and Freidinger, The design of metabolically-stable peptide analogs, Trends Neurosci., 8:392-396 (1985).
Veiseh et al., Optical and MRI Multifunctional Nanoprobe for Targeting Gliomas, Nano Letters, 5(6):1003-1008 (2005).
Veiseh, M. et al., Tumor Paint: A Chlorotoxin: Cy5.5 Bioconjugate for Intraoperative Visualization of Cancer Foci, Caner Res. 67:6882-6888 (2007).
Veiseh, O. et al., A ligand-mediated nanovector for targeted gene delivery and transfection in cancer cells, Biomaterials, 30(4):649-657 (2009).
Veiseh, O. et al., Specific targeting of brain tumors with an optical/magnetic resonance imaging nanoprobe across the blood-brain barrier, Cancer Res, 69(15):6200-7 (2009).
Voet and Voet, Biochemistry, John Wiley & Sons, Inc., 235-241 (1995).
Weissleder, R. and Ntziachristos, V., Shedding light onto live molecular targets, Nat Med, 9(1):123-8 (2003).
Wen et al., PTEN controls tumor-induced angiogenesis, Proc Natl Acad Sci USA, 98:4622-4627 (2001).
Wilson, G. and Chiu, S., Mitogenic factors regulate ion channels in Schwann cells cultured from newborn rat sciatic nerve, J. Physiol. 470:501-520 (1993).
Wishart, D.S. et al., 1H, 13C and 15N chemical shift referencing in biomolecular NMR, J Biomol NMR, 6(2):135-40 (1995).
Woodfork, K. et al., Inhibition of ATP-sensitive potassium channels causes reversible cellcycle arrest of human breast cancer cells in tissue culture, J. Cell. Physiol. 162:163-171 (1995).
Written Opinion for PCT/US04/39325, 3 pages (Mar. 27, 2006).
Written Opinion for PCT/US05/11523, 6 pages (Feb. 9, 2006).
Written Opinion for PCT/US2006/010170, 8 pages (Oct. 22, 2007).
Written Opinion for PCT/US2007/008309, 8 pages (Nov. 20, 2007).
Written Opinion for PCT/US2008/076740, 5 pages (Jan. 9, 2009).
Written Opinion for PCT/US2009/044149, 8 pages (Oct. 19, 2009).
Written Opinion for PCT/US2011/023797, 5 pages (Nov. 18, 2011).
Written Opinion for PCT/US2011/023823, 6 pages (Apr. 25, 2011).
Yasuda et al., Annexin A2 autoantibodies detected in serum of cancer patients, Anticancer Res., 30(7):2631-9 (2010).
Ye, Y. and Chen, X., Integrin Targeting for Tumor Optical Imaging, Theranostics 1:102-126 (2011).
Zellner et al., Disparity in expression of protein kinase C alpha in human glioma versus glioma-derived primary cell lines: therapeutic implications, Clin. Can. Res., 4:1797-1802 (1998).
Zhang, Y. et al., Surface modification of superparamagnetic magnetite nanoparticles and their intracellular uptake, Biomaterials, 23(7):1553-61 (2002).
Zips et al., New Anticancer Agents: In Vitro and In Vivo Evaluation, In Vivo, 19:1-8 (2005).

CHLOROTOXIN POLYPEPTIDES AND CONJUGATES AND USES THEREOF

RELATED APPLICATIONS

This application is a divisional of U.S. patent application Ser. No. 14/450,182, filed Aug. 1, 2014, which issued as U.S. Pat. No. 9,234,015 on Jan. 12, 2016, and which is a continuation of U.S. patent application Ser. No. 13/577,169, filed Aug. 3, 2012 (and having a 35 U.S.C. 371(c) date of Oct. 3, 2012), which issued as U.S. Pat. No. 9,018,347 on Apr. 28, 2015, and which is a U.S. National Stage Application filed under 35 U.S.C. 371 based on International Application No. PCT/US2011/23823, filed Feb. 4, 2011, which claims the benefit of U.S. Provisional Application No. 61/301,615, filed Feb. 4, 2010, each of which is herein incorporated by reference in its entirety.

BACKGROUND

Chlorotoxin is a peptide component of venom from the scorpion *Leiurius quinquestriatus* that has been shown to bind specifically to tumor cells. Chlorotoxin has been used as a targeting agent to deliver cytotoxic and/or imaging agents to a variety of tumors including metastatic tumors and brain tumors such as malignant glioma. For example, chlorotoxin has been conjugated to the radioactive isotope iodine-131, and such chlorotoxin conjugates have been shown to be effective anti-tumor therapeutic agents. Other chlorotoxin conjugates including protein fusions, such as a chlorotoxin-GST fusion protein attached to saporin, have also been shown to result in a significant and selective killing of tumor cells.

SUMMARY

Chlorotoxin can be potentially conjugated to any of a wide variety of agents, including cytotoxic and/or imaging agents. Although currently available chlorotoxin conjugates have demonstrated anti-tumor properties, the present invention encompasses the recognition that a greater repertoire of chlorotoxin conjugates may offer many advantages. To give but one example, different chlorotoxin conjugates may have their own sets of pharmacokinetic properties that may be particularly desirable for a given tumor type and/or patient. Furthermore, the present invention identifies a previously undocumented source of a potential problem with certain types of chlorotoxin conjugates, stemming from the reality that the wild type chlorotoxin polypeptide (and many variants of that polypeptide) contains more than one site at which conjugation can occur. The present invention therefore provides the insight that chemical reactions to generate conjugates with chlorotoxin often result in mixtures of conjugate species. In at least some embodiments, such different species may have different properties. Moreover, efforts to reproduce findings made with such chlorotoxin conjugate mixtures may be hampered by challenges reproducing the distribution of different species within the preparation. Quality control, and even analysis, may be difficult or impossible.

The present invention provides new types of chlorotoxin conjugates, and identifies the source of problems that can be encountered with other chlorotoxin conjugates. That is, the present invention recognizes that many prior chlorotoxin conjugates are prepared by chemically conjugating a moiety or entity of interest to a chlorotoxin polypeptide. According to the present invention, it is recognized that in at least some instances, such approaches generate mixed populations of conjugates in which moieties or entities of interest are conjugated to chlorotoxin at different points or locations. The present invention encompasses the recognition that such mixed populations may be difficult to characterize and/or reproduce, and may show different properties (e.g., pharmacokinetic properties), which differences may be unpredictable. The present invention encompasses the recognition that preparations containing only a single species chlorotoxin conjugates may be more desirable than preparations containing mixtures of conjugates, for example, in therapeutic and/or diagnostic applications.

The present invention also provides solutions to this identified source of a problem. For example, the present invention provides reduced lysine chlorotoxin polypeptides that can generate single species conjugates. In certain embodiments, provided are reduced lysine chlorotoxin polypeptides. In various aspects, provided are chlorotoxin conjugates comprising chlorotoxin polypeptides having not more than one lysine available as a site for conjugation ("monolysine chlorotoxin conjugates"), pharmaceutical compositions comprising such conjugates, and methods of using such conjugates. In some embodiments, provided reduced lysine chlorotoxin polypeptides have no lysine residues.

In certain embodiments, the present invention provides methods of making and of using reduced lysine chlorotoxin polypeptides and conjugates thereof. In some embodiments, provided reduced lysine chlorotoxin polypeptides and/or conjugates thereof may be used in medicine (e.g., in various therapeutic and/or diagnostic contexts).

DEFINITIONS

As used herein, the terms "about" and "approximately," in reference to a number, is used herein to include numbers that fall within a range of 20%, 10%, 5%, or 1% in either direction (greater than or less than) the number unless otherwise stated or otherwise evident from the context (except where such number would exceed 100% of a possible value).

As used herein, the term "characteristic sequence element" or "sequence element" refers to a stretch of contiguous amino acids, typically at least 5 amino acids, e.g., at least 5-50, 5-25, 5-15 or 5-10 amino acids, that shows at least about 80%, 85%, 90%, 95%, 96%, 97%, 98%, 99% or 100% identity with another polypeptide. In some embodiments, a characteristic sequence element participates in or confers function on a polypeptide. In some embodiments, reduced lysine chlorotoxin polypeptides comprise a characteristic sequence element. In some such embodiments, reduced lysine chlorotoxin polypeptides comprise a characteristic sequence element that is TTDHQMAR (SEQ ID NO: 29).

The terms "chemotherapeutic," "anti-cancer agent" and "anti-cancer drug" are used herein interchangeably. They refer to medications that are used to treat cancer or cancerous conditions. Anti-cancer drugs are conventionally classified in one of the following group: radioisotopes (e.g., Iodine-131, Lutetium-177, Rhenium-188, Yttrium-90), toxins (e.g., diphtheria, *pseudomonas*, ricin, gelonin), enzymes, enzymes to activate prodrugs, radio-sensitizing drugs, interfering RNAs, superantigens, anti-angiogenic agents, alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones and anti-androgens. Examples of such anti-cancer agents include, but are not limited to, BCNU, cisplatin, gemcitabine, hydroxyurea, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomysin, tamoxifen, flutamide, leuprolide, goserelin, aminogluthimide, anastrozole, amsacrine, asparaginase, mitoxantrone, mitotane and amifostine.

As used herein, the term "chlorotoxin" refers to a peptide of 36 amino acids in length, having an amino acid sequence (SEQ ID NO: 1). The term "chlorotoxin" as used herein encompasses chlorotoxin that is isolated from venom of scorpion *Leiurius quinquestriatus* or other organisms in which chlorotoxin may be found, as well as recombinant and synthetic chlorotoxin.

As used herein, the phrase "chlorotoxin conjugate" refers to a chlorotoxin polypeptide covalently associated with one or more entity/entities or moiety/moieties of interest. In some embodiments, the entity of interest is not a polypeptide, and/or is not linked within the polypeptide chain. In some embodiments, the entity of interest is liked to an amino acid side chain. In some embodiments, the entity of interest is linked to the chlorotoxin polypeptide via a lysine residue.

As used herein, the phrase "chlorotoxin polypeptide" refers to a polypeptide showing at least 45% overall sequence identity with chlorotoxin (SEQ ID NO: 1), and having a length of between twenty four and forty amino acids, inclusive. In some embodiments, the chlorotoxin polypeptide has at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% overall sequence identity with SEQ ID NO: 1. In some embodiments, a chlorotoxin polypeptide has at least 65% overall sequence identity with SEQ ID NO: 1. In some embodiments, a chlorotoxin polypeptide has at least 91% overall sequence identity with SEQ ID NO: 1. In some embodiments, a chlorotoxin polypeptide has at least 94% overall sequence identity with SEQ ID NO: 1. In some embodiments, a chlorotoxin polypeptide has at least 97% overall sequence identity with SEQ ID NO: 1. In some embodiments, a chlorotoxin polypeptide further shares at least one characteristic sequence element with SEQ ID NO: 1. In some embodiments, the characteristic sequence element is TTDHQMAR (SEQ ID NO: 29). In some embodiments, a chlorotoxin polypeptide has a length between twenty-four and forty amino acids inclusive. In some embodiments, a "chlorotoxin polypeptide" includes one or more additional stretch(es) of amino acids, typically at the C- and/or N-terminus and/or as discrete block inserted within a sequence. Typically such additional stretches are about 3 to about 1000 amino acids long. In some embodiments, additional stretches are about 3-100, 3-90, 3-80, 3-70, 3-60, 3-50, 3-40, 3-30 or 3-20 amino acids long. In some embodiments, additional stretches are about or less than 20 amino acids long, about or less than 15 amino acids long, or about or less than 10 amino acids long. In some embodiments, the additional stretch comprises one or more known tags. In some embodiments, the additional stretch comprises a cytotoxic agent.

As used herein, the phrase "combination therapy" refers to the administration of two or more active agents to the same subject, such that the subject is exposed to both agents at the same time. Those of ordinary skill in the art will appreciate that any individual agent may desirably be administered in a single dose, or in multiple doses, for example spaced out over predetermined intervals or in a predetermined pattern. Combination therapy does not require that individual doses of the two or more active agents be administered at the same time so long as the subject receiving the doses is simultaneously exposed to both agents. Combination therapy also does not require that the two or more active agents be administered by the same route. In some embodiments, one or both of the at least two active agents administered in combination therapy is administered at a dose and/or frequency that is reduced as compared with its dose or frequency when administered alone.

The phrase "corresponding to," when used to describe positions or sites within amino acid or nucleotide sequences, is used herein as it is understood in the art. As is well known in the art, two or more amino acid or nucleotide sequences can be aligned using standard bioinformatic tools, including programs such as BLAST, ClustalX, Sequencher, and etc. Even though the two or more sequences may not match exactly and/or do not have the same length, an alignment of the sequences can still be performed and, if desirable, a "consensus" sequence generated. Indeed, programs and algorithms used for alignments typically tolerate definable levels of differences, including insertions, deletions, inversions, polymorphisms, point mutations, etc. Such alignments can aid in the determination of which positions in one nucleotide sequence correspond to which positions in other nucleotide sequences.

As used herein, the phrase "dosing regimen" refers to a set of unit doses (typically more than one) that are administered individually separated by periods of time. The recommended set of doses (i.e., amounts, timing, route of administration, etc.) for a particular pharmaceutical agent or composition constitutes its dosing regimen.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the purpose(s) may be: to inhibit angiogenesis, cause regression of neovasculature, interfere with activity of another bioactive molecule, cause regression of a tumor, inhibit metastases, reduce extent of metastases, etc. The relevant intended purpose may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

As used herein, terms "fluorophore," "fluorescent moiety," "fluorescent label," "fluorescent dye" and "fluorescent labeling moiety" are used herein interchangeably. They refer to a molecule that, in solution and upon excitation with light of appropriate wavelength, emits light back. Numerous fluorescent dyes of a wide variety of structures and characteristics are suitable for use in the practice of this invention. Similarly, methods and materials are known for fluorescently labeling nucleic acids (see, for example, R. P. Haugland, "*Molecular Probes: Handbook of Fluorescent Probes and Research Chemicals* 1992-1994", $5^{th}$ Ed.", a 1994, Molecular Probes, Inc.). In choosing a fluorophore, it is often desirable that the fluorescent molecule absorbs light and emits fluorescence with high efficiency (i.e., high molar absorption coefficient and fluorescence quantum yield, respectively) and is photostable (i.e., it does not undergo significant degradation upon light excitation within the time necessary to perform the analysis).

As used herein, the term "inhibit" means to prevent something from happening, to delay occurrence of something happening, and/or to reduce the extent or likelihood of something happening. Thus, "inhibiting angiogenesis" and "inhibiting the formation of neovasculature" is intended to encompass preventing, delaying, and/or reducing the likelihood of angiogenesis occiring as well as reducing the number, growth rate, size, etc., of neovessels.

The terms "labeled" and "labeled with a detectable agent or moiety" are used herein interchangeably to specify that an entity (e.g., a reduced lysine chlorotoxin polypeptide or chlorotoxin conjugate) can be visualized, for example following binding to another entity (e.g., a neoplastic tumor tissue). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionuclides, fluorophores, chemiluminescent agents, microparticles, enzymes, colorimetric labels, magnetic labels, haptens, molecular beacons, aptamer beacons, and the like.

As used herein, the term "macular degeneration" refers to a medical condition that results in loss of vision in the center of the visual field (the macula) because of damage to the retina. Several forms of macular degeneration are known to exist, and unless specified, the term "macular degeneration" includes all forms. "Wet macular degeneration" (also known as the neovascular or exudative form) refers to macular degeneration that involves the growth of blood vessels from the choroid behind the retina. In wet macular degeneration, the retina may sometimes become detached. In "dry macular degeneration" (also known as the non-exudative form), cellular debris called drusen accumulate between the retina and the choroid, but no blood vessel formation occurs. "Age-related macular degeneration" (ARMD) refers to the most common form of macular degeneration, which typically begins later in life with characteristic yellow deposits in the macula. ARMD may occur in either the wet or dry forms of macular degeneration.

As used herein, the term "metastasis" (sometimes abbreviated as "mets"; plural "metastases") refers to the spread of tumor cells from one organ or tissue to another location. The term also refers to tumor tissue that forms in a new location as a result of metastasis. A "metastatic cancer" is a cancer that spreads from its original, or primary, location, and may also be referred to as a "secondary cancer" or "secondary tumor." Generally, metastatic tumors are named for the tissue of the primary tumor from which they originate. Thus, a breast cancer that has metastasized to the lung may be referred to as "metastatic breast cancer" even though some cancer cells are located in the lung.

As used herein, the phrase "monolysine chlorotoxin polypeptide" refers to a chlorotoxin polypeptide that has only one lysine residue that is available as a site for conjugation. In some embodiments, monolysine chlorotoxin polypeptides have only one lysine residue. In some embodiments, monolysine chlorotoxin polypeptides have more than one lysine residue, but only one of the lysine residues is available as a site for conjugation. In some such embodiments, one or more blocking groups on some lysines make them unavailable as a site for conjugation.

As used herein, the term "neovasculature" refers to newly formed blood vessels that have not yet fully matured, i.e., do not have a fully formed endothelial lining with tight cellular junctions or a complete layer of surrounding smooth muscle cells. As used herein, the term "neovessel" is used to refer to a blood vessel in neovasculature.

The terms "pharmaceutical agent," "therapeutic agent" and "drug" are used herein interchangeably. They refer to a substance, molecule, compound, agent, factor or composition effective in the treatment, inhibition, and/or detection of a disease, disorder, or clinical condition.

A "pharmaceutical composition" is herein defined as a composition that comprises an effective amount of at least one active ingredient (e.g., a reduced lysine chlorotoxin polypeptide or chlorotoxin conjugate that may or may not be labeled), and at least one pharmaceutically acceptable carrier.

As used herein, the term "preventing" when used to refer to the action of an agent to a process (e.g., angiogenesis, metastasis, cancer progression, etc.) means reducing extent of and/or delaying onset of such a process when the agent (e.g., a therapeutic agent such as a chlorotoxin conjugate) is administered prior to development of one or more symptoms or attributes associated with the process.

As used herein, the term "primary tumor" refers to a tumor that is at the original site where the tumor first arose, i.e., as opposed to having spread there.

The term "prodrug" refers to a compound that, after in vivo administration, is metabolized or otherwise converted to the biologically, pharmaceutically or therapeutically active form of the compound. A prodrug may be designed to alter the metabolic stability or the transport characteristics of a compound, to mask side effects or toxicity, to improve the flavor of a compound and/or to alter other characteristics or properties of a compound. By virtue of knowledge of pharmacodynamic processes and drug metabolisms in vivo, once a pharmaceutically active compound is identified, those of skill in the pharmaceutical art generally can design prodrugs of the compound (Nogrady, "Medicinal Chemistry A Biochemical Approach", 1985, Oxford University Press: N.Y., pages 388-392). Procedures for the selection and preparation of suitable prodrugs are also known in the art. In some embodiments, a prodrug is a compound whose conversion to its active form (after in vivo administration) involves enzymatic catalysis.

The terms "protein," "polypeptide" and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative slicing or limited proteolysis), or in the alternative, may arise from differential post-translational modification (e.g., glycosylation, acylation or phosphorylation).

As used herein, the phrase "reduced lysine chlorotoxin polypeptide" refers to a chlorotoxin polypeptide that has fewer lysine residues than chlorotoxin (SEQ ID NO: 1) has and/or has fewer lysine residues that are available as a site for conjugation than chlorotoxin has. In certain embodiments, a reduced lysine chlorotoxin polypeptide has not more than one lysine residue. In some embodiments, a reduced lysine chlorotoxin polypeptide has only one lysine residue. In certain embodiments, a reduced lysine chlorotoxin polypeptide has not more than one lysine residue available as a site for conjugation. In some embodiments, all but one lysine residue in a reduced lysine chlorotoxin polypeptide have been modified such that they are not available as a site for conjugation. In some embodiments, all lysine residues in a reduced lysine chlorotoxin polypeptide have been modified such that they are not available as a site for conjugation. In some embodiments, a reduced lysine chlorotoxin polypeptide contains a single site available for conjugation.

The term "regress," when used to refer to blood vessels and/or vasculature (including neovasculature and/or neovessels), is used herein to mean to retract, shrink, etc.

The terms "subject" and "individual" are used herein interchangeably. They refer to a human or another mammal (e.g., mouse, rat, rabbit, dog, cat, cattle, swine, sheep, horse or primate) that can be afflicted with or is susceptible to a disease or disorder (e.g., cancer, macular degeneration, etc.) but may or may not have the disease or disorder. In many embodiments, the subject is a human being. In many embodiments, the subject is a patient. Unless otherwise stated, the terms "individual" and "subject" do not denote a particular age, and thus encompass adults, children, and newborns.

As used herein, the term "susceptible" means having an increased risk for and/or a propensity for (typically based on genetic predisposition, environmental factors, personal history, or combinations thereof) something, i.e., a disease, disorder, or condition (such as, for example, cancer, metastatic cancer, macular degeneration, rheumatoid arthritis, etc.) than is observed in the general population. The term takes into account that an individual "susceptible" for a condition may never be diagnosed with the condition.

As used herein, the term "systemic administration" refers to administration of an agent such that the agent becomes widely distributed in the body in significant amounts and has a biological effect, e.g., its desired effect, in the blood and/or reaches its desired site of action via the vascular system. Typical systemic routes of administration include administration by (1) introducing the agent directly into the vascular system or (2) oral, pulmonary, or intramuscular administration wherein the agent is adsorbed, enters the vascular system, and is carried to one or more desired site(s) of action via the blood.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" a cancer may refer to inhibiting survival, growth, and/or spread of tumor cells; preventing, delaying, and/or reducing the likelihood of occurrence of metastases and/or recurrences; and/or reducing the number, growth rate, size, etc., of metastases. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of a pharmaceutical composition to a subject.

As used herein, the phrase "unit dose" refers to a discrete amount of a pharmaceutical composition comprising a predetermined amount of an active ingredient (e.g., a therapeutic agent). The amount of the active ingredient is generally equal to the dosage of the active ingredient that would be administered to a subject and/or a convenient fraction of such a dosage such as, for example, one-half or one-third of such a dosage.

DETAILED DESCRIPTION OF CERTAIN
EMBODIMENTS OF THE INVENTION

I. Reduced Lysine Chlorotoxin Polypeptides

As shown in Table 1 and as listed in SEQ ID NO: 1, chlorotoxin is a 36-amino acid peptide having three lysine residues, at positions 15, 23, and 27 of SEQ ID NO: 1. In certain embodiments, the present invention provides chlorotoxin polypeptides having a reduced number of lysine residues ("reduced lysine chlorotoxin polypeptides"). In certain embodiments, a reduced lysine chlorotoxin polypeptide has an amino acid sequence corresponding to that of SEQ ID NO: 1 in that the reduced lysine chlorotoxin polypeptide has at least 45% overall sequence identity with SEQ ID NO: 1 and a length of between twenty-four and forty amino acid residues inclusive. In some embodiments, a reduced lysine chlorotoxin polypeptide has at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% overall sequence identity with SEQ ID NO: 1. In some embodiments, a reduced lysine chlorotoxin polypeptide has at least 65% overall sequence identity with SEQ ID NO: 1. In some embodiments, a chlorotoxin polypeptide has at least 91% overall sequence identity with SEQ ID NO: 1. For example, a reduced lysine chlorotoxin polypeptide may be identical in amino acid sequence to chlorotoxin at 33 out of 36 amino acid residues (i.e., ~91.7% sequence identity). In some embodiments, a chlorotoxin polypeptide has at least 94% overall sequence identity with SEQ ID NO: 1. For example, a reduced lysine chlorotoxin polypeptide may be identical in amino acid sequence to chlorotoxin at 34 out of 36 amino acid residues (i.e., ~94.4% sequence identity). In some embodiments, a reduced lysine chlorotoxin polypeptide has at least 97% overall sequence identity with SEQ ID NO: 1. For example, a reduced lysine chlorotoxin polypeptide may be identical in amino acid sequence to chlorotoxin at 35 out of 36 amino acid residues (i.e., ~97.2% sequence identity). In some embodiments, a reduced lysine chlorotoxin polypeptide is and/or contains a stretch of 33, 34, 35, 36, 37, or 38 amino acids whose sequence corresponds to or shows at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% overall sequence identity with the sequence of chlorotoxin.

Table 1 depicts the sequence of chlorotoxin and sequences of exemplary reduced lysine chlorotoxin polypeptides. Table 1 is not intended to be limiting, but rather, is used to illustrate certain exemplary reduced lysine chlorotoxin polypeptides provided by the present invention.

TABLE 1

Sequences of Chlorotoxin and of Exemplary Reduced Lysine Chlorotoxin Polypeptides

| SEQ ID NO: | Comment | Sequence (N-terminus to C-terminus) |
|---|---|---|
| | Chlorotoxin | |
| 1 | Full length chlorotoxin | MCMPC FTTDH QMARK CDDCC GGKGR GKCYG PQCLC R |
| | Exemplary reduced lysine polypeptides | |
| 2 | No lysines | MCMPC FTTDH QMARC DDCCG GGRGC YGPQC LCR |
| 3 | No lysines at positions 15, 23, or 27 of SEQ ID NO: 1; lysine at N-terminus | KMCMP CFTTD HQMAR CDDCC GGGRG CYGPQ CLCR |
| 4 | No lysines at positions 15, 23 or 27 of SEQ ID NO: 1; lysine at C-terminus | MCMPC FTTDH QMARC DDCCG GGRGC YGPQC LCRK |
| 5 | Lysines at positions 15, 23, and 27 of SEQ ID NO: 1 replaced by alanine | MCMPC FTTDH QMARA CDDCC GGAGR GACYG PQCLC R |
| 6 | Lysines at positions 15, 23, and 27 of SEQ ID NO: 1 replaced by arginine | MCMPC FTTDH QMARR CDDCC GGRGR GRCYG PQCLC R |
| 7 | Lysines at positions 15, 23, and 27 of SEQ ID NO: 1 replaced by alanine; lysine at N-terminus | KMCMP CFTTD HQMAR ACDDC CGGAG RGACY GPQCL CR |
| 8 | Lysines at positions 15, 23, and 27 of SEQ ID NO: 1 replaced by arginine; lysine at N-terminus | KMCMP CFTTD HQMAR RCDDC CGGRG RGRCY GPQCL CR |
| 9 | Lysines at positions 15, 23, and 27 of SEQ ID NO: 1 replaced by alanine; lysine at C-terminus | MCMPC FTTDH QMARA CDDCC GGAGR GACYG PQCLC RK |
| 10 | Lysines at positions 15, 23, and 27 of SEQ ID NO: 1 replaced by arginine; lysine at C-terminus | MCMPC FTTDH QMARR CDDCC GGRGR GRCYG PQCLC RK |
| 11 | No lysine at position 15 of SEQ ID NO: 1 | MCMPC FTTDH QMARC DDCCG GKGRG KCYGP QCLCR |
| 12 | No lysine at position 23 of SEQ ID NO: 1 | MCMPC FTTDH QMARK CDDCC GGGRG KCYGP QCLCR |

TABLE 1-continued

Sequences of Chlorotoxin and of Exemplary Reduced Lysine Chlorotoxin Polypeptides

| SEQ ID NO: | Comment | Sequence (N-terminus to C-terminus) |
|---|---|---|
| 13 | No lysine at position 27 of SEQ ID NO: 1 | MCMPC FTTDH QMARK CDDCC GGKGR GCYGP QCLCR |
| 14 | No lysines at positions 15 and 23 of SEQ ID NO: 1 | MCMPC FTTDH QMARC DDCCG GGRGK CYGPQ CLCR |
| 15 | No lysines at positions 15 and 27 of SEQ ID NO: 1 | MCMPC FTTDH QMARC DDCCG GKGRG CYGPQ CLCR |
| 16 | No lysines at positions 23 and 27 of SEQ ID NO: 1 | MCMPC FTTDH QMARK CDDCC GGGRG CYGPQ CLCR |
| 17 | Lysines at positions 15 and 23 of SEQ ID NO: 1 replaced by alanine | MCMPC FTTDH QMARA CDDCC GGAGR GKCYG PQCLC R |
| 18 | Lysines at positions 15 and 27 of SEQ ID NO: 1 replaced by alanine | MCMPC FTTDH QMARA CDDCC GGKGR GACYG PQCLC R |
| 19 | Lysines at positions 23 and 27 of SEQ ID NO: 1 replaced by alanine | MCMPC FTTDH QMARK CDDCC GGAGR GACYG PQCLC R |
| 20 | Lysines at positions 15 and 23 of SEQ ID NO: 1 replaced by arginine | MCMPC FTTDH QMARR CDDCC GGRGR GKCYG PQCLC R |
| 21 | Lysines at positions 15 and 27 of SEQ ID NO: 1 replaced by arginine | MCMPC FTTDH QMARR CDDCC GGKGR GRCYG PQCLC R |
| 22 | Lysines at positions 23 and 27 of SEQ ID NO: 1 replaced by arginine | MCMPC FTTDH QMARK CDDCC GGRGR GRCYG PQCLC R |
| 23 | Lysine at position 15 of SEQ ID NO: 1 replaced by arginine; lysine at position 27 of SEQ ID NO: 1 replaced by alanine | MCMPC FTTDH QMARR CDDCC GGKGR GACYG PQCLC R |
| 24 | No lysine at position 15 of SEQ ID NO: 1; lysines at positions 23 and 27 of SEQ ID NO: 1 replaced by arginine | MCMPC FTTDH QMARC DDCCG GAGRG ACYGP QCLCR |
| 25 | No lysine at position 23 of SEQ ID NO: 1; lysines at positions 15 and 27 replaced by arginine | MCMPC FTTDH QMARA CDDCC GGGRG ACYGP QCLCR |
| 26 | No lysine at position 27 of SEQ ID NO: 1; lysines at positions 15 and 23 replaced by arginine | MCMPC FTTDH QMARR CDDCC GGRGR GCYGP QCLCR |

In certain embodiments, reduced lysine chlorotoxin polypeptides have not more than one lysine available as a site for conjugation. In some such embodiments, one lysine is available and it is at a position within the chlorotoxin polypeptide that corresponds to a position where a lysine is present in chlorotoxin (i.e., position 15, 23 or 27 of SEQ ID NO: 1). In some embodiments, the single lysine that is available is at position 15 of SEQ ID NO: 1. In some embodiments, the single lysine that is available is at position 23 of SEQ ID NO: 1. In some embodiments, the single lysine that is available is at position 27 of SEQ ID NO: 1. In some embodiments, a single lysine is present in a reduced lysine chlorotoxin polypeptide of the present invention at a position corresponding to a site in chlorotoxin that does not contain a lysine residue (i.e., not at a position corresponding to any of positions 15, 23 or 27 of SEQ ID NO: 1).

In certain embodiments, a reduced lysine chlorotoxin polypeptide lacks at least one amino acid residue corresponding to position 15, 23, or 27 of SEQ ID NO: 1.

In certain embodiments, a reduced lysine chlorotoxin polypeptide lacks lysine residues entirely. (See, e.g., SEQ ID NOs: 2, 5, 6, 24, 25 and 26). In some embodiments, an amino acid is missing where a lysine residue is normally found in chlorotoxin. In some embodiments, one or more lysine residues normally found in chlorotoxin is/are replaced by another amino acid residue and/or by an amino acid derivative. In other words, at least one amino acid residue in the polypeptide corresponding to positions 15, 23 or 27 of SEQ ID NO: 1 is not a lysine. In addition to the nineteen other naturally occurring amino acids of which polypeptides are typically comprised (alanine, arginine, aspartic acid, asparagine, cysteine, glutamic acid, glutamine, glycine, histidine, isoleucine, leucine, methionine, phenylalanine, proline, serine, threonine, tyrosine, tryptophan, and valine), a variety of substitutes may be used. Non-limiting examples of substitutes include other naturally occurring amino acids, non-naturally occurring amino acids such as D-amino acids, and amino acid derivatives. Non-limiting examples of other naturally occurring amino acids include beta-alanine, carnitine, citrulline, cystine, gamma-aminobutyric acid, hydroxyproline, ornithine, and taurine. (For additional examples of naturally occurring amino acids and of amino acid derivatives, see, e.g., Wagner and Musso (1983), "New Naturally Occuring Amino Acids," *Agnew. Chem. Int. Ed. Engl.,* 22:816-828, the entire of contents of which are herein incorporated by reference.) In some embodiments, one or more lysine residues is/are replaced by arginine and/or alanine.

In some embodiments in which a reduced lysine chlorotoxin polypeptide lacks lysine residues entirely, one terminus or both termini (i.e., the N- and/or C-terminus) of the reduced lysine chlorotoxin polypeptide can serve as a site for chemical conjugation. Availability of the terminus or termini may depend on the particular conjugation chemistry employed. In some embodiments in which a reduced lysine chlorotoxin polypeptide lacks lysine residues entirely, only the alpha amino group at the N-terminus is available as a site for conjugation.

In embodiments in which more than one lysine residue is replaced, the same or different amino acid residue(s) or amino acid derivative(s) may be used to replace the lysine residues. See, e.g., SEQ ID NOs: 17-22 for non-limiting examples in which the same amino acid residue has been used to replace lysine residues and SEQ ID NO: 23 for a non-limiting example in which different amino acid residues have been used to replace lysine residues.

In some embodiments, a reduced lysine chlorotoxin polypeptide has only one lysine in the sequence (a "monolysine chlorotoxin polypeptide"). In some embodiments, such a chlorotoxin polypeptide has a lysine residue where a lysine residue is normally present in chlorotoxin, e.g., at a position corresponding to position 15, 23, or 27 of SEQ ID NO: 1 (See, e.g., SEQ ID NOs: 14-23 for non-limiting examples). In some embodiments, a reduced lysine chlorotoxin polypeptide does not have any lysine residues where a lysine residue is normally present in chlorotoxin (i.e., positions 15, 23, and 27 of SEQ ID NO: 1), but has a lysine residue at a position that does not correspond to any of positions 15, 23, and 27 of SEQ ID NO: 1. As with chlorotoxin polypeptides having no lysines at all, monolysine chlorotoxin polypeptides may be missing amino acids at one or more positions corresponding to positions 15, 23 and 27 of SEQ ID NO: 1, and/or may have an amino acid or amino acid derivative substitution at one or more positions corresponding to positions 15, 23 and 27 of SEQ ID NO: 1.

In some embodiments, provided reduced lysine chlorotoxin polypeptides have an amino acid sequence that includes one or more than one lysine residues but nonetheless have a reduced number of lysines available for conjugation when compared with chlorotoxin. In some embodiments, one or more lysine residues in a reduced lysine chlorotoxin polypeptide provided herein is/are made unavailable as a site for conjugation though they are present in the chlorotoxin polypeptide. For example, one or more lysine residue(s) can be covalently or non-covalently modified such that the one or more lysine residue(s) is/are blocked from participating in a chemical conjugation reaction, leaving fewer than 3, 2 or 1 (i.e., "reduced" lysine) lysine residue(s) available as a site for conjugation. Non-limiting examples of covalent modifications to lysine residues that could be employed in this manner include pegylation (i.e., modification by attachment of a polyethylene glycol polymer), methylation (including di- and tri-methylation), and attachment of other alkyl group(s). In certain embodiments, one or more lysine residues is/are modified at the epsilon $NH_2$ group. For example, if a given R group (e.g., butyl, propyl, or ethyl group) is used to covalently modify a lysine residue, the epsilon $NH_2$ group can be modified to an $NR_2$ or $NR_3$ group.

Table 2 presents some non-limiting examples of modification schemes that could be used to produce reduced lysine chlorotoxin polypeptides.

TABLE 2

Exemplary modification schemes

| SEQ ID NO: | Core sequence (N-terminus to C-terminus) | Position(s) of lysine residue(s) |
|---|---|---|
| 1 | MCMPC FTTDH QMARK CDDCC<br>5     10     15     20<br>GGKGR GKCYG PQCLC R<br>25     30     35 | 15, 23 and 27<br>15 and 23<br>15 and 27<br>23 and 27 |
| 11 | MCMPC FTTDH QMARC DDCCG<br>5     10     15     20<br>GKGRG KCYGP QCLCR<br>25     30     35 | 22 and 26<br>22<br>26 |
| 12 | MCMPC FTTDH QMARK CDDCC<br>5     10     15     20<br>GGGRG KCYGP QCLCR<br>25     30     35 | 15 and 26<br>15<br>26 |

TABLE 2-continued

Exemplary modification schemes

| SEQ ID NO: | Core sequence (N-terminus to C-terminus) | Position(s) of lysine residue(s) |
|---|---|---|
| 13 | MCMPC FTTDH QMARK CDDCC<br>     5      10     15    20<br>GGKGR GCYGP QCLCR<br>  25      30     35 | 15 and 23<br>15<br>23 |
| 27 (lysine added to N-term) | KMCMP CFTTD HQMAR KCDDC<br>     5      10     15    20<br>CGGKG RGKCY GPQCL CR<br>  25      30     35 | 16, 24 and 28 |
| 28 (lysine added to C-term) | CMCMPC FTTDH QMARK CDDCC<br>     5      10     15    20<br>GGKGR GKCYG PQCLC RK<br>  25      30     35 | 15, 23 and 27 |

In certain embodiments, blocking of particular lysine residue is achieved by incorporating a modified lysine (in which sites available for conjugation are already blocked) during the appropriate step during synthesis of the reduced lysine chlorotoxin polypeptide. Modified lysines are readily available commercially and can be synthesized by routine methods known in the art. Non-limiting examples of modified lysines that can be used in this manner include, but are not limited to, di-substituted lysine or trisubstituted lysines (e.g., N,N—$R_2$-lysine or N,N,N—$R_3$-lysine, where R is the blocking group) and lysines with short PEG molecules attached to them. R can be any group that when covalently attached to the lysine would serve to block the lysine residue from participating in a chemical conjugation reaction. For example, alkyl groups (e.g., butyl, methyl, and ethyl) may serve as blocking groups. For example, N,N-dimethyl-lysine and/or N,N,N-trimethyl-lysine be used during synthesis.

In certain embodiments, one terminus or both termini (i.e., the N- and/or C-terminus) of the reduced lysine chlorotoxin polypeptide is blocked so as to prevent the terminus/ termini from participating in a chemical conjugation reaction. For example, in some embodiments, a conjugation chemistry is used in which at least one terminus would participate in the conjugation reaction if it were not blocked. A variety of methods of blocking N- and/or C-termini of polypeptides are known in the art, including, but not limited to, covalent modification by the addition of alkyl groups (e.g., methylation) at amines.

Methods of synthesizing reduced lysine chlorotoxin polypeptides as described herein are known in the art. In some peptide synthesis methods, an amino group of one amino acid (or amino acid derivative) is linked to a carboxyl group of another amino acid (or amino acid derivative) that has been activated by reacting it with a reagent such as dicyclohexylcarbodiimide (DCC). When the free amino group attacks the activated carboxyl group, a peptide bond is formed and dicyclohexylurea is released. In such methods, other potentially reactive groups (such as the α-amino group of the N-terminal amino acid or amino acid derivative and the carboxyl group of the C-terminal amino acid or amino acid derivative) may be blocked ("protected") from participating in the chemical reaction. Thus, only particular active groups react such that the desired product is formed. Blocking groups useful for this purpose include without limitation tertbutoxycarbonyl groups (t-Boc) and benzoyloxycarbonyl groups to protect amine groups; and simple esters (such as methyl and ethyl groups) and benzyl esters to protect carboxyl groups. Blocking groups can typically be subsequently removed with a treatment that leaves peptide bonds intact (for example, treatment with dilute acid). This process of protecting reacting groups that should not react, coupling to form a peptide bond, and deprotecting reactive groups may be repeated. A peptide may be synthesized by sequentially adding amino acids to a growing peptide chain. Both liquid-phase and solidphase peptide synthesis methods are suitable for use in accordance with the invention. In solid-phase peptide synthesis methods, the growing peptide chain is typically linked to an insoluble matrix (such as, for example, polystyrene beads) by linking the carboxyterminal amino acid to the matrix. At the end of synthesis, the peptide can be released from the matrix using a cleaving reagent that does not disrupt peptide bonds, such as hydrofluoric acid (HF).

Protecting groups are also typically removed at this time. Automated, high throughput, and/or parallel peptide synthesis methods may also be used in accordance with the invention. For more information about peptide synthesis methods, see, e.g., Merrifield (1969) "Solid-phase peptide synthesis," Adv Enzymol Relat Areas Mol Biol., 32:221-96; Fridkin et al. (1974) *Annu Rev Biochem.*, 43 (0):419-43; Merrifield (1997) "Concept and Early Development of Solid Phase Peptide Synthesis," *Methods in Enzymology*, 289:3-13; Sabatino et al. (2009) "Advances in automatic, manual and microwave-assisted solid-phase peptide synthesis," *Curr Opin Drug Discov Devel.*, 11(6):762-70, the entire contents of each of which are herein incorporated by reference.

In some embodiments, modifications to lysine residues are used in combination with other means as described herein (e.g., replacement of a lysine residue with another amino acid or amino acid derivative and/or lack of a lysine residue where one is normally found in chlorotoxin).

In some embodiments, the protecting group in the N-terminus is not removed at the end of synthesis. Leaving the protecting group on may, for example, serve to generate a reduced lysine chlorotoxin polypeptide with a blocked N-terminus, thus limiting the sites available for conjugation in a particular chemical conjugation scheme.

II. Chlorotoxin Conjugates

In certain embodiments, provided are chlorotoxin conjugates comprising a reduced lysine chlorotoxin polypeptide associated with one or more entities or moieties. Chlorotoxin conjugates of the present invention can include a polypeptide of any length that comprises a reduced lysine chlorotoxin polypeptide as described herein.

A. Conjugation

In some embodiments, the one or more entities or moieties is/are associated with reduced lysine chlorotoxin polypeptides via a lysine residue and/or via a terminus of the reduced lysine chlorotoxin polypeptide. In some such embodiments, the position(s) where entities or moieties can be attached to a reduced lysine chlorotoxin polypeptide is limited by the number of lysine residues available as a site for conjugation. For example, entities or moieties can be attached at the single available lysine residue in monolysine chlorotoxin polypeptides.

In some embodiments, entities or moieties are associated at the N-terminus of or at the C-terminus of the reduced lysine chlorotoxin polypeptide. In some such embodiments, the reduced lysine chlorotoxin polypeptide does not have any lysine residues available for conjugation at any of the "native" positions within chlorotoxin (e.g., positions corresponding to positions 15, 23 and 27).

In some embodiments, the reduced lysine chlorotoxin polypeptide is covalently associated to the one or more entity/entities or moeity/moieties. As will be appreciated by those skilled in the art, a reduced lysine chlorotoxin polypeptide and one or more entity/entities and/or moiety/moieties may be attached either directly or indirectly (e.g., through a linker).

A variety of conjugation chemistries are known in the art and may be used in the practice of the present invention. In certain embodiments, one or more entity/entities or moiety/moieties are attached to the epsilon amino group of a lysine residue. In some embodiments, the conjugation chemistry is based on NHS (N-hydroxysuccinimide)/EDC (1-ethyl-3-[3-dimethylaminopropyl]carbodiimide hydrochloride) chemistry. In some embodiments, the conjugation chemistry is based on thiolation chemistry, i.e., using a thiolating agent such as Traut's reagent and/or 2-Iminothiolane.

In certain embodiments, a reduced lysine chlorotoxin polypeptide and one or more entity/entities or moiety/moieties are directly, covalently, linked to each other. Such direct covalent binding can be achieved in any of a variety of ways, for example, via amide, ester, carbon-carbon, disulfide, carbamate, ether, thioether, urea, amine, or carbonate bonds. Such covalent binding can be achieved, for example, by taking advantage of function groups present on the entity/entities or moiety/moieties and/or on the reduced lysine chlorotoxin polypeptide. Suitable functional groups that can be used include, but are not limited to, amines, anhydrides, hydroxyl groups, carboxyl groups, thiols, and the like. In certain embodiments, a functional group of one part of the future conjugate is activated for coupling to the other part of the future conjugate. For example, an activating agent, such as a carbodiimide, can be used to effect such a coupling. A wide variety of activating agents are known in the art and are suitable for forming a provided conjugate.

In some embodiments, a reduced lysine chlorotoxin polypeptide and one or more entity/entities or moiety/moieties are indirectly covalently linked to each other via a linker group. Such indirect covalent linkage can be accomplished by using any of a number of stable bifunctional agents well known in the art, including homofunctional and heterofunctional agents. For non-limiting examples of such agents, see, e.g., Pierce Catalog and Handbook. Use of a bifunctional agent differs from use of an activating agent in that the former results in a linking moiety being present in the resulting conjugate, whereas the latter results in a direct coupling between two moieties involved in the reaction. A role of the bifunctional agent may be to allow a reaction between two otherwise inert moieties. Alternatively or additionally, the bifunctional agent, which becomes part of the reaction product, may be selected such that in confers some degree of conformational flexibility to the conjugate. For example, the bifunctional agent may comprise a straight alkyl chain containing several atoms, for example, between 2 and 10 carbon atoms. Alternatively or additionally, the bifunctional agent may be selected such that the linkage formed between the reduced lysine chlorotoxin polypeptide and the one or more entity/entities or moiety/moieties is cleavable, e.g., hydrolysable. (For non-limiting examples of such linkers, see, e.g., U.S. Pat. Nos. 5,773,001; 5,739,116 and 5,877,296, the contents of each of which is incorporated herein by reference.) Such linkers may, for example, be used when the entity or moiety being conjugated to the reduced lysine chlorotoxin polypeptide is a therapeutic moiety that is observed to have a higher activity after hydrolysis from the reduced lysine chlorotoxin polypeptide. Exemplary mechanisms to achieve cleavage include hydrolysis in the acidic pH of lysosomes (hydrazones, acetals, and cis-aconitate-like amides), peptide cleavage by lysosomal enzymes (e.g., cathepsins and other lysosomal enzymes), and reduction of disulfides. Additional cleavage mechanisms include hydrolysis at physiological pH extra- or intracellularly. This mechanism may be applied when the crosslinker used to couple the one or more entity/entities or moiety/moieties to the reduced lysine chlorotoxin polypeptide is a biodegradable/bioerodible entity, such as polydextran and the like.

For example, for conjugates comprising one or more therapeutic moieties, hydrazone-containing conjugates can be made with introduced carbonyl groups that provide the desired drug-release properties. Conjugates can also be made with a linker that comprises an alkul chain with a disulfide group at one end and a hydrazine derivative at the other end.

Linkers containing functional groups other than hydrazones also have the potential to be cleaved in the acidic miliey of lysosomes. For example, conjugates can be made from thiol-reactive linkers that contain a group other than a hydrazone that is cleavable intracellularly, such as esters, amides, and acetals/ketals. Ketals made from a 5 to 7 member ring ketone that has one of the oxygen atoms attached to the entity or moiety and the other to a linker for attachment to a reduced lysine chlorotoxin polypeptide can also be used.

A further example of class pH-sensitive linkers are the cis-aconitates, which have a carboxylic acid group juxtaposed to an amide group. The carboxylic acid accelerates amide hydrolysis in the acidid lysosomes. Linkers that achieve a similar type of hydrolysis rate acceleration with several other types of structures can also be used.

Enzymatic hydrolysis of peptides by lysosomal enzymes may also be used to release entities or moieties from conjugates. For example, a reduced lysine chlorotoxin polypeptide can be attached via an amide bond to para-aminobenzyl alcohol and then a carbamate or carbonate can be made between the benzyl alcohol and the entity or moiety. Cleavage of the reduced lysine chlorotoxin polypeptide leads to collapse of the amino benzyle carabamate or carbonate, and release of the entity or moeity. As a further example, a phenol can be cleaved by collapse of the linker instead of the carbamate. As a yet further example, disulfide reaction is used to initiate collapse of a para-meraptobenzyl carbamate or carbonate.

Many therapeutic moieties, in particular anti-cancer agents, have little, if any, solubility in water, which limits drug loading on a conjugate due to aggregation of the therapeutic moiety. One approach to overcoming this is to add solubilizing groups to the linker Conjugates made with a linker consisting of PEG (polyethylene glycol) and a dipeptide can be used, including, for example, those having a PEG di-acid thiol-acid, or maleimide-acid attached to the reduced lysine chlorotoxin conjugate, a dipeptide spacer, and an amide bound to the entity or moiety. Approaches that incorporate PEG groups may be beneficial in overcoming aggregation and limits in drug loading.

In embodiments in which entity or moiety within a chlorotoxin conjugate is a protein, polypeptide, or peptide, the chlorotoxin conjugate may be a fusion protein. A fusion protein is a molecule comprising two or more proteins, polypeptides, or peptides linked by a covalent bond via their individual peptide backbones. Fusion proteins used in methods of the present invention can be produced by any suitable method known in the art. For example, they can be produced by direct protein synthetic methods using a polypeptide synthesizer. Alternatively, PCR amplification of gene fragments can be carried out using anchor primers which give rise to complementary overhangs between two consecutive gene fragments that can subsequently be annealed and re-amplified to generate a chimeric gene sequence. Fusion proteins can be obtained by standard recombinant methods (See, for example, Maniatis et al. "*Molecular Cloning: A Laboratory Manual,*" 2$^{nd}$ Ed., 1989, Cold Spring Harbor Laboratory, Cold Spring, N.Y., the entire contents of which are herein incorporated by reference). These methods generally comprise (1) construction of a nucleic acid molecule that encodes the desired fusion protein; (2) insertion of the nucleic acid molecule into a recombinant expression vector; (3) transformation of a suitable host cell with the expression vector; and (4) expression of the fusion protein in the host cell. Fusion proteins produced by such methods may be recovered and isolated, either directly from the culture medium or by lysis of the cells, as known in the art. Many methods for purifying proteins produced by transformed host cells are well-known in the art. These include, but are not limited to, precipitation, centrifugation, gel filtration, and column chromatography (e.g., ionexchange, reverse-phase, and affinity). Other purification methods have been described (See, for example, Deutscher et al. "*Guide to Protein Purification*" in Methods in Enzymology, 1990, vol. 192, Academic Press, the entire contents of which are herein incorporated by reference).

In certain embodiments, the reduced lysine chlorotoxin polypeptide is noncovalently associated to the one or more entity/entities or moiety/moieties. Examples of non-covalent associations include, but are not limited to, hydrophobic interactions, electrostatic interactions, dipole interactions, van der Waals interactions, and hydrogen bonding.

Irrespective of the nature of the association between the toxin moiety and therapeutic agent, the association is typically selective, specific, and strong enough so that the conjugate does not dissociate before or during transport to and into cells. Association between a reduced lysine chlorotoxin polypeptide and one or more entity/entities or moiety/moieties may be achieved using any chemical, biochemical, enzymatic, or genetic coupling known to one skilled in the art.

As can readily be appreciated by those skilled in the art, a conjugate of the present invention can comprise any number of reduced lysine chlorotoxin polypeptides and any number of entities or moieties, associated to one another by any number of different ways. The design of a conjugate will be influenced by its intended purpose(s) and the properties that are desirable in the particular context of its use. Selection of a method to associate or bind a reduced lysine chlorotoxin polypeptide to an entity or moiety to form a conjugate is within the knowledge of one skilled in the art and will generally depend on the nature of the association desired (i.e., covalent vs. non-covalent and/or cleavable vs. non-cleavable), the nature of the reduced lysine chlorotoxin polypeptide and the entity/moiety, the presence and nature of functional chemical groups, and the like.

B. Entities/Moieties

As mentioned above, in certain embodiments, chlorotoxin conjugates comprise one or more non-chlorotoxin entities. Any of a variety of such entities or moieties may be employed.

1. Therapeutic Entities/Moieties

In certain embodiments, provided conjugates comprise one or more therapeutic entities or moeities, as described below and in International Patent Publication No. WO 2009/021136 A1, the entire contents of which are herein incorporated by reference in their entirety.

a. Anti-Cancer Agents

In some embodiments, the one or more therapeutic entities or moieties comprises an anti-cancer agent. Suitable anti-cancer agents include any of a large variety of substances, molecules, compounds, agents or factors that are directly or indirectly toxic or detrimental to cancer cells, including, for example, cytotoxic agents. Anti-cancer agents suitable for use in the practice of the invention may be synthetic or natural. Anticancer agents may comprise a single molecule or a complex of different molecules.

Suitable anti-cancer agents can belong to any of various classes of compounds including, but not limited to, small molecules, peptides, saccharides, steroids, antibodies, fusion proteins, antisense polynucleotides, ribozymes, small interfering RNAs, peptidomimetics, and the like. Similarly, suitable anti-cancer agents can be found among any of a variety of classes of anti-cancer agents including, but not limited to, alkylating agents, anti-metabolite drugs, anti-mitotic antibiotics, alkaloidal anti-tumor agents, hormones and anti-hormones, interferons, non-steroidal anti-inflammatory drugs, and various other anti-tumor agents.

Particularly suitable anti-cancer agents are agents that cause undesirable side effects due to poor selectivity/specificity for cancer cells; agents that undergo no or poor cellular uptake and/or retention; agents that are associated with cellular drug resistance; and agents that cannot be readily formulated for administration to cancer patients due to poor water solubility, aggregation, and the like.

Examples of suitable anti-cancer agents that can be used in conjugates of the present invention are described in more detail below.

Poorly Water Soluble Anti-Cancer Drugs

In certain embodiments, an anti-cancer agent within an inventive conjugate is a poorly water soluble compound. As will be recognized by one skilled in the art, a wide variety of poorly water soluble anti-cancer agents are suitable for use in the present invention.

For example, an anti-cancer agent may be selected among taxanes, which are recognized as effective agents in the treatment of many solid tumors that are refractory to other anti-neoplastic agents. Two currently approved taxanes are paclitaxel (TAXOL™) and docetaxel (TAXOTERE™). Paclitaxel, docetaxel, and other taxanes act by enhancing the polymerization of tubulin, an essential protein in the formation of spindle microtubules. Polymerization of tubulin results in the formation of very stable, nonfunctional tubules, which inhibits cell replication and leads to cell death.

Paclitaxel is very poorly water soluble, and therefore, cannot be practically formulated with water for intravenous administration. Some formulations of TAXOL™ for injection or intravenous infusion have been developed using CREMOPHOR EL™ (polyoxyethylated castor oil) as a drug carrier. However, CREMOPHOR™ EL is itself toxic, and is considered to be, at least in part, responsible for the hypersensitivity reactions (severe skin rashes, hives, flushing, dyspnea, tacchycardia and others) associated with administration of such preparations. To avoid such side effects, premedication is often prescribed along with paclitaxel formulations containing CREMOPHOR™. Docetaxel, which is an analog of paclitaxel, is like paclitaxel poorly soluble in water. The currently most preferred solvent used to dissolve docetaxel for pharmaceutical use is polysorbate 80 (TWEEN 80). In addition to causing hypersensitivity reactions in patients, TWEEN 80 cannot be used with PVC delivery apparatus, because of its tendency to leach diethylhexyl phthalate, which is highly toxic.

A conjugate according to the present invention comprising a taxane and chlorotoxin polypeptide can be used as an improved delivery method to avoids the use of solvents and carriers that induce adverse reactions in patients.

In some embodiments, an anti-cancer agent within a chlorotoxin conjugate may belong to the enediyne family of antibiotics. As a family, the enediyne antibiotics are particularly potent anti-tumor agents. Some members are 1000 times more potent than adriamycin, one of the most effective, clinically used anti-tumor antibiotics (Y. S. Zhen et al., J. Antibiot., 1989, 42: 1294-1298). For example, an anti-cancer agent within an inventive conjugate may be a member of the enediyne family of calicheamicins. Originally isolated from a broth extract of the soil microorganism *Micromonospora echinospora* ssp. *calichensis*, the calicheamicins were detected in a screen for potent DNA damaging agents (M. D. Lee et al., J. Am. Chem. Soc., 1987, 109: 3464-3466; M. D. Lee et al., J. Am. Chem. Soc., 1987, 109: 3466-3468; W. M. Maiese et al., J. Antibiot., 1989, 42: 558-563; M. D. Lee et al., J. Antibiot., 1989, 42: 1070-1087).

Calicheamicins are characterized by a complex, rigid bicyclic enediyne allylic trisulfide core structure linked through glycosyl bonds to an oligosaccharide chain. The oligosaccharide portion contains a number of substituted sugar derivatives, and a substituted tetrahydropyran ring. The enediyne containing core (or aglycone) and carbohydrate portions of calicheamicins have been reported to carry out different roles in the biological activity of these molecules. It is generally believed that the core portion cleaves DNA, whereas the oligosaccharide portion of the calicheamicins serves as a recognition and delivery system and guides the drug to a double-stranded DNA minor groove in which the drug anchors itself ("Enediyne Antibiotics as Antitumor Agents", Doyle and Borders, 1995, Marcel-Dekker: New York). Double-stranded DNA cleavage is a type of damage that is usually non-repairable or non-easily repairable for the cell and is most often lethal.

Because of their chemical and biological properties, several analogues of the calicheamicins have been tested in preclinical models as potential anti-tumor agents. Their development as single agent therapies has not been pursued because of delayed toxicities that limit the therapeutic dose range for treatment. However, their potency makes them particularly useful for targeted chemotherapy.

Other examples of suitable poorly water soluble anti-cancer agents include tamoxifen and BCNU. Tamoxifen has been used with varying degrees of success to treat a variety of estrogen receptor positive carcinomas such as breast cancer, endometrial carcinoma, prostate carcinoma, ovarian carcinoma, renal carcinoma, melanoma, colorectal tumors, desmoid tumors, pancreatic carcinoma, and pituitary tumors. In addition to being limited by poor water solubility, chemotherapy using tamoxifen can cause side effects such as cellular drug resistance. BCNU (1,3-bis(2-chloroethyl)-1-nitrosourea) is well known for its anti-tumor properties and, since 1972, it has been charted by the National Cancer Institute for use against brain tumors, colon cancer, Hodgkin's Disease, lung cancer and multiple myeloma. However, the efficient use of this anti-cancer drug is also compromised by its low solubility.

Anti-Cancer Agents Associated with Drug Resistance

In certain embodiments of the present invention, chlorotoxin conjugates comprise an anti-cancer agent associated with drug resistance. As used herein, the term "anti-cancer agent associated with drug resistance" refers to any chemotherapeutic to which cancer cells are or can become resistant. As already mentioned above, resistance to an anti-cancer agent can be due to many factors and can operate by different mechanisms. Administration of a conjugate of the present invention comprising a reduced lysine chlorotoxin polypeptide and an anti-cancer agent associated with drug resistance can enhance cellular uptake of the anti-cancer agent and carry it into tumor cells, e.g., resistant tumor cells.

Any of a wide variety of anti-cancer agents associated with drug resistance are suitable for use in the present invention. For example, the anti-cancer agent associated with drug resistance may be methotrexate. Methotrexate, a widely used cancer drug, is an analogue of folic acid and blocks important steps in the synthesis of tetrahydrofolic acid which itself is a critical source of compounds utilized in the synthesis of thymidylate, a building block that is specific and therefore especially critical for DNA synthesis. Methotrexate-induced drug resistance is linked to a deficiency in cellular uptake of that drug.

Other examples of suitable anti-cancer agents include purine and pyrimidine analogs that are associated with drug resistance due to inadequate intracellular activation of the drug through loss of enzymatic activity. An example of such a purine analog is 6-mercaptopurine (6-MP). A common cause of tumor cell resistance to 6-MP is the loss of the enzyme hypoxanthine guanine phosphoribosyl transferase (HGPRT) which activates 6-MP into its corresponding nucleotide, 6-mercaptophosphoribosylpurine (6-MPRP), the lethal form of the drug. Without being held to theory, it is postulated that resistance could be overcome if 6-MPRP itself could be introduced into the cell. Although this compound is commercially available, it has not yet been used therapeutically in cancer treatment because it is not adequately transported into living cells. Association of 6-MPRP to a reduced lysine chlorotoxin polypeptide according to the present invention would dramatically increase its ability to cross the cell membrane. Thioguanine is another example of anti-cancer agent that is associated with drug resistance due to lack of the enzyme HGPRT.

Examples of pyrimidine analogs that are associated with drug resistance due to inadequate intracellular activation include cytosine arabinoside and adenosine arabinoside which are activated by the enzyme deoxycytidine kinase (DOCK) to the lethal forms cytosine diphosphate and adenosine diphosphate, respectively. A reduced lysine chlorotoxin polypeptide can be coupled to the activated form of such pyrimidine analogs to enhance their cellular uptake and overcome cellular drug resistance.

Other examples of anti-cancer agents associated with drug resistance include, but are not limited to, 5-fluorouracil, fluorodeoxyuridine, cytosine, arabinoside, vinblastin, vincristin, daunorubicin, doxorubicin, actinomycin, and bleomycin.

Other Anti-Cancer Agents

In some embodiments, an anti-cancer agent is selected from the group consisting of alkylating drugs (e.g., mechlorethamine, chlorambucil, cyclophosphamide, melphalan, ifosfamide), antimetabolites (e.g., methotrexate), purine antagonists and pyrimidine antagonists (e.g., 6-mercaptopurine, 5-fluorouracil, cytarabile, gemcitabine), spindle poisons (e.g., vinblastine, vincristine, vinorelbine, paclitaxel), podophyllotoxins (e.g., etoposide, irinotecan, topotecan), antibiotics (e.g., doxorubicin, Neomycin, mitomycin), nitrosoureas (e.g., carmustine, lomustine), inorganic ions (e.g., cisplatin, carboplatin), enzymes (e.g., asparaginase), and hormones (e.g., tamoxifen, leuprolide, flutamide, and megestrol), to name a few. For a more comprehensive discussion of updated cancer therapies see <www.cancer-

Nucleic Acid Agents

In certain embodiments, chlorotoxin conjugates comprise a nucleic acid agent.

Numerous cancers and tumors have been shown to be associated with varying degrees of genetic impairment, such as point mutations, gene deletions, or duplications. Many new strategies for the treatment of cancer, such as those that have been termed "antisense," "antigene" and "RNA interference" have been developed to modulate the expression of genes (A. Kalota et al., Cancer Biol. Ther., 2004, 3: 4-12; Y. Nakata et al., Crit. Rev. Eukaryot. Gene Expr., 2005, 15: 163-182; V. Wacheck and U. Zangmeister-Wittke, Crit. Rev. Oncol. Hematol., 2006, 59: 65-73; A. Kolata et al., Handb. Exp. Pharmacol., 2006, 173: 173-196). These approaches utilize, for example, antisense nucleic acids, ribozymes, triplex agents, or short interfering RNAs (siRNAs) to block the transcription or translation of a specific mRNA or DNA of a target gene, either by masking that mRNA with an antisense nucleic acid or DNA with a triplex agent, by cleaving the nucleotide sequence with a ribozyme, or by destruction of the mRNA, through a complex mechanism involved in RNA-interference. In many of these strategies, mainly oligonucleotides are used as active agents, although small molecules and other structures have also been applied. While oligonucleotide-based strategies for modulating gene expression have a huge potential for the treatment of some cancers, pharmacological applications of oligonucleotides have been hindered mainly by ineffective delivery of these compounds to their sites of action within cancer cells. (P. Herdewijn et al., Antisense Nucleic Acids Drug Dev., 2000, 10: 297-310; Y. Shoji and H. Nakashima, Curr. Charm. Des., 2004, 10: 785-796; A. W Tong et al., Curr. Opin. Mol. Ther., 2005, 7: 114-124).

In certain embodiments, provided chlorotoxin conjugates comprise a reduced lysine chlorotoxin polypeptide and a nucleic acid molecule that is useful as a therapeutic (e.g., anti-cancer) agent. A variety of chemical types and structural forms of nucleic acid can be suitable for such strategies. These include, by way of non-limiting example, DNA, including single-stranded (ssDNA) and double-stranded (dsDNA); RNA, including, but not limited to ssRNA, dsRNA, tRNA, mRNA, rRNA, enzymatic RNA; RNA:DNA hybrids, triplexed DNA (e.g., dsDNA in association with a short oligonucleotide), and the like.

In some embodiments, the nucleic acid agent is between about 5 and 2000 nucleotides long. In some embodiments, the nucleic acid agent is at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides long. In some embodiments, the nucleic acid agent is less than about 2000, 1900, 1800, 1700, 1600, 1500, 1400, 1300, 1200, 1100, 1000, 900, 800, 700, 600, 500, 450, 400, 350, 300, 250, 200, 150, 100, 50, 45, 40, 35, 30, 25, 20 or fewer nucleotides long.

In some embodiments, the nucleic acid agent comprises a promoter and/or other sequences that regulate transcription. In some embodiments, the nucleic acid agent comprises an origin of replication and/or other sequences that regulate replication. In some embodiments, the nucleic acid agent does not include a promoter and/or an origin of replication.

Nucleic acid anti-cancer agents suitable for use in the practice of the present invention include those agents that target genes associated with tumorigenesis and cell growth or cell transformation (e.g., proto-oncogenes, which code for proteins that stimulate cell division), angiogenic/anti-angiogenic genes, tumor suppressor genes (which code for proteins that suppress cell division), genes encoding proteins associated with tumor growth and/or tumor migration, and suicide genes (which induce apoptosis or other forms of cell death), especially suicide genes that are most active in rapidly dividing cells.

Examples of genes associated with tumorigenesis and/or cell transformation include MLL fusion genes, BCR-ABL, TEL-AML1, EWS-FLI1, TLS-FUS, PAX3-FKHR, Bcl-2, AML1-ETO, AML1-MTG8, Ras, Fos PDGF, RET, APC, NF-1, Rb, p53, MDM2 and the like; overexpressed genes such as multidrug resistance genes; cyclins; beta-Catenin; telomerase genes; c-myc, n-myc, Bcl-2, Erb-B1 and Erb-B2; and mutated genes such as Ras, Mos, Raf, and Met. Examples of tumor suppressor genes include, but are not limited to, p53, p21, RB1, WT1, NF1, VHL, APC, DAP kinase, p16, ARF, Neurofibromin, and PTEN. Examples of genes that can be targeted by nucleic acid agents useful in anti-cancer therapy include genes encoding proteins associated with tumor migration such as integrins, selectins, and metalloproteinases; anti-angiogenic genes encoding proteins that promote formation of new vessels such as Vascular Endothelial Growth Factor (VEGF) or VEGFr; anti-angiogenic genes encoding proteins that inhibit neovascularization such as endostatin, angiostatin, and VEGF-R2; and genes encoding proteins such as interleukins, interferon, fibroblast growth factor ($\alpha$-FGF and ($\beta$-FGF), insulin-like growth factor (e.g., IGF-1 and IGF-2), Platelet-derived growth factor (PDGF), tumor necrosis factor (TNF), Transforming Growth Factor (e.g., TGF-$\alpha$ and TGF-$\beta$, Epidermal growth factor (EGF), Keratinocyte Growth Factor (KGF), stem cell factor and its receptor c-Kit (SCF/c-Kit) ligand, CD40L/CD40, VLA-4 VCAM-1, ICAM-1/LFA-1, hyalurin/CD44, and the like. As will be recognized by one skilled in the art, the foregoing examples are not exclusive.

Nucleic acid agents suitable for use in the invention may have any of a variety of uses including, for example, use as anti-cancer or other therapeutic agents, probes, primers, etc. Nucleic acid agents may have enzymatic activity (e.g., ribozyme activity), gene expression inhibitory activity (e.g., as antisense or siRNA agents, etc), and/or other activities. Nucleic acids agents may be active themselves or may be vectors that deliver active nucleic acid agents (e.g., through replication and/or transcription of a delivered nucleic acid). For purposes of the present specification, such vector nucleic acids are considered "therapeutic agents" if they encode or otherwise deliver a therapeutically active agent, even if they do not themselves have therapeutic activity.

In certain embodiments, chlorotoxin conjugates comprise a nucleic acid therapeutic agent that comprises or encodes an antisense compound. The terms "antisense compound or agent," "antisense oligomer," "antisense oligonucleotide," and "antisense oligonucleotide analog" are used herein interchangeably, and refer to a sequence of nucleotide bases and a subunit-to-subunit backbone that allows the antisense compound to hybridize to a target sequence in an RNA by Watson-Crick base pairing to form an RNA oligomer heteroduplex within the target sequence. The oligomer may have exact sequence complementarity within the target sequence or near complementarity. Such antisense oligomers may block or inhibit translation of the mRNA containing the target sequence, or inhibit gene transcription. Antisense oligomers may bind to double-stranded or single-stranded sequences.

Examples of antisense oligonucleotides suitable for use in the practice of the present invention include, for example, those mentioned in the following reviews: R. A Stahel et al., Lung Cancer, 2003, 41: S81-S88; K. F. Pirollo et al., Pharmacol. Ther., 2003, 99: 55-77; A. C. Stephens and R. P. Rivers, Curr. Opin. Mol. Ther., 2003, 5: 118-122; N. M. Dean and C. F. Bennett, Oncogene, 2003, 22: 9087-9096; N. Schiavone et al., Curr. Pharm. Des., 2004, 10: 769-784; L. Vidal et al., Eur. J. Cancer, 2005, 41: 2812-2818; T. Aboul-Fadl, Curr. Med. Chem., 2005, 12: 2193-2214; M. E. Gleave and B. P. Monia, Nat. Rev. Cancer, 2005, 5: 468-479; Y. S. Cho-Chung, Curr. Pharm. Des., 2005, 11: 2811-2823; E. Rayburn et al., Lett. Drug Design & Discov., 2005, 2: 1-18; E. R. Raybum et al., Expert Opin. Emerg. Drugs, 2006, 11: 337-352; I. Tamm and M. Wagner, Mol. Biotechnol., 2006, 33: 221-238 (each of which is incorporated herein by reference in its entirety).

Examples of suitable antisense oligonucleotides include, for example oblimersen sodium (also known as Genasense™ or G31239, developed by Genta, Inc., Berkeley Heights, N.J.), a phosphorothioate oligomer targeted towards the initiation codon region of the bcl-2 mRNA. Bcl-2 is a potent inhibitor of apoptosis and is overexpressed in many cancer including follicular lymphomas, breast cancer, colon cancer, prostate cancer, and intermediate/high-grade lymphomas (C. A. Stein et al., Semin. Oncol., 2005, 32: 563-573; S. R. Frankel, Semin. Oncol., 2003, 30: 300-304). Other suitable antisense oligonucleotides include GEM-231 (HYB0165, Hybridon, Inc., Cambridge, Mass.), which is a mixed backbone oligonucleotide directed against cAMP-dependent protein kinase A (PKA) (S. Goel et al., Clin. Cancer Res., 203, 9: 4069-4076); Affinitak (ISIS 3521 or aprinocarsen, ISIS pharmaceuticals, Inc., Carlsbad, Calif.), an antisense inhibitor of PKCalpha; OGX-011 (Isis 112989, Isis Pharmaceuticals, Inc.), a 2'-methoxyethyl modified antisense oligonucleotide against clusterin, a glycoprotein implicated in the regulation of the cell cycle, tissue remodeling, lipid transport, and cell death and which is overexpressed in cancers of breast, prostate and colon; ISIS 5132 (Isis 112989, Isis Pharmaceuticals, Inc.), a phosphorothioate oligonucleotide complementary to a sequence of the 3'-unstranslated region of the c-raf-1 mRNA (S. P. Henry et al., Anticancer Drug Des., 1997, 12: 409-420; B. P. Monia et al., Proc. Natl. Acad. Sci. USA, 1996, 93: 15481-15484; C. M. Rudin et al., Clin. Cancer Res., 2001, 7: 1214-1220); ISIS 2503 (Isis Pharmaceuticals, Inc.), a phosphorothioate oligonucleotide antisense inhibitor of human H-ras mRNA expression (J. Kurreck, Eur. J. Biochem., 2003, 270: 1628-1644); oligonucleotides targeting the X-linked inhibitor of apoptosis protein (XIAP), which blocks a substantial portion of the apoptosis pathway, such as GEM 640 (AEG 35156, Aegera Therapeutics Inc. and Hybridon, Inc.) or targeting survivin, an inhibitor of apoptosis protein (IAP), such as ISIS 23722 (Isis Pharmaceuticals, Inc.), a 2'-O-methoxyethyl chimeric oligonucleotide; MG98, which targets DNA methyl transferase; and GTI-2040 (Lorus Therapeutics, Inc. Toronto, Canada), a 20-mer oligonucleotide that is complementary to a coding region in the mRNA of the R2 small subunit component of human ribonucleotide reductase.

Other suitable antisense oligonucleotides include antisense oligonucleotides that are being developed against Her-2/neu, c-Myb, c-Myc, and c-Raf (see, for example, A. Biroccio et al., Oncogene, 2003, 22: 6579-6588; Y. Lee et al., Cancer Res., 2003, 63: 2802-2811; B. Lu et al., Cancer Res., 2004, 64: 2840-2845; K. F. Pirollo et al., Pharmacol. Ther., 2003, 99: 55-77; and A. Rait et al., Ann. N.Y. Acad. Sci., 2003, 1002: 78-89).

In certain embodiments, chlorotoxin conjugates of the present invention comprise a nucleic acid anti-cancer agent that comprises or encodes an interfering RNA molecule. The terms "interfering RNA" and "interfering RNA molecule" are used herein interchangeably, and refer to an RNA molecule that can inhibit or downregulate gene expression or silence a gene in a sequence-specific manner, for example by mediating RNA interference (RNAi). RNA interference (RNAi) is an evolutionarily conserved, sequence-specific mechanism triggered by double-stranded RNA (dsRNA) that induces degradation of complementary target single-stranded mRNA and "silencing" of the corresponding translated sequences (McManus and Sharp, 2002, Nature Rev. Genet., 2002, 3: 737). RNAi functions by enzymatic cleavage of longer dsRNA strands into biologically active "short-interfering RNA" (siRNA) sequences of about 21-23 nucleotides in length (Elbashir et al., Genes Dev., 2001, 15: 188). RNA interference has emerged as a promising approach for therapy of cancer.

An interfering RNA suitable for use in the practice of the present invention can be provided in any of several forms. For example, an interfering RNA can be provided as one or more of an isolated short interfering RNA (siRNA), double-stranded RNA (dsRNA), micro-RNA (miRNA), or short hairpin RNA (shRNA).

Examples of interfering RNA molecules suitable for use in the present invention include, for example, the iRNAs cited in the following reviews: O. Milhavet et al., Pharmacol. Rev., 2003, 55: 629-648; F. Bi et al., Curr. Gene. Ther., 2003, 3: 411-417; P. Y. Lu et al., Curr. Opin. Mol. Ther., 2003, 5: 225-234; I. Friedrich et al., Semin. Cancer Biol., 2004, 14: 223-230; M. Izquierdo, Cancer Gene Ther., 2005, 12: 217-227; P. Y. Lu et al., Adv. Genet., 2005, 54: 117-142; G. R. Devi, Cancer Gene Ther., 2006, 13: 819-829; M. A. Behlke, Mol. Ther., 2006, 13: 644-670; and L. N. Putral et al., Drug News Perspect., 2006, 19: 317-324 (the contents of each of which are incorporated herein by reference in their entirety).

Other examples of suitable interfering RNA molecules include, but are not limited to, p53 interfering RNAs (e.g., T. R. Brummelkamp et al., Science, 2002, 296: 550-553; M. T. Hemman et al., Nat. Genet., 2003, 33: 396-400); interfering RNAs that target the bcr-abl fusion, which is associated with development of chronic myeloid leukemia and acute lymphoblastic leukemia (e.g., M. Scherr et aL, Blood, 2003, 101: 1566-1569; M. J. Li et al., Oligonucleotides, 2003, 13: 401-409), interfering RNAs that inhibit expression of NPM-ALK, a protein that is found in 75% of anaplastic large cell lymphomas and leads to expression of a constitutively active kinase associated with tumor formation (U. Ritter et al., Oligonucleotides, 2003, 13: 365-373); interfering RNAs that target oncogenes, such as Raf-1 (T. F. Lou et al., Oligonucleotides, 2003, 13: 313-324), K-Ras (T. R. Brummelkamp et al., Cancer Cell, 2002, 2: 243-247), erbB-2 (G. Yang et al., J. Biol. Chem., 2004, 279: 4339-4345); interfering RNAs that target b-catenin protein, whose over-expression leads to transactivation of the T-cell factor target genes, which is thought to be the main transforming event in colorectal cancer (M. van de Wetering et al., EMBO Rep., 2003, 4: 609-615).

In certain embodiments, chlorotoxin conjugates comprise a nucleic acid therapeutic agent that is a ribozyme. As used herein, the term "ribozyme" refers to a catalytic RNA molecule that can cleave other RNA molecules in a target-specific marmer Ribozymes can be used to downregulate the expression of any undesirable products of genes of interest. Examples of ribozymes that can be used in the practice of the present invention include, but are not limited to, ANGIOZYME™ (RPI.4610, Sima Therapeutics, Boulder, Colo.), a ribozyme targeting the conserved region of human, mouse, and rat vascular endothelial growth factor receptor (VEGFR)-1 mRNA, and Herzyme (Sima Therapeutics).

Photosensitizers

In certain embodiments, entities or moieties within chlorotoxin conjugates comprise a photosensitizer used in photodynamic therapy (PDT). In PDT, local or systemic administration of a photosensitizer to a patient is followed by irradiation with light that is absorbed by the photosensitizer in the tissue or organ to be treated. Light absorption by the photosensitizer generates reactive species (e.g., radicals) that are detrimental to cells. For maximal efficacy, a photosensitizer typically is in a form suitable for administration, and also in a form that can readily undergo cellular internalization at the target site, often with some degree of selectivity over normal tissues.

While some photosensitizers (e.g., Photofrin®, QLT, Inc., Vancouver, BC, Canada) have been delivered successfully as part of a simple aqueous solution, such aqueous solutions may not be suitable for hydrophobic photosensitizer drugs, such as those that have a tetra- or poly-pyrrole-based structure. These drugs have an inherent tendency to aggregate by molecular stacking, which results in a significant reduction in the efficacy of the photosensitization processes (Siggel et al., J. Phys. Chem., 1996, 100: 2070-2075). Approaches to minimize aggregation include liposomal formulations (e.g., for benzoporphyrin derivative monoacid A, BPDMA, Verteporfin®, QLT, Inc., Vancouver, Canada; and zinc phthalocyanine, CIBA-Geigy, Ltd., Basel, Switzerland), and conjugation of photosensitizers to biocompatible block copolymers (Peterson et al., Cancer Res., 1996, 56: 3980-3985) and/or antibodies (Omelyanenko et al., Int. J. Cancer, 1998, 75: 600-608).

Chlorotoxin conjugates comprising a reduced lysine chlorotoxin polypeptide associated with a photosensitizer can be used as new delivery systems in PDT. In addition to reducing photosensitizer aggregation, delivery of photosensitizers according to the present invention exhibits other advantages such as increased specificity for target tissues/organ and cellular internalization of the photosensitizer.

Photosensitizers suitable for use in the present invention include any of a variety of synthetic and naturally occurring molecules that have photosensitizing properties useful in PDT. In certain embodiments, the absorption spectrum of the photosensitizer is in the visible range, typically between 350 nm and 1200 nm, preferably between 400 nm and 900 nm, e.g., between 600 nm and 900 nm. Suitable photosensitizers that can be coupled to toxins according to the present invention include, but are not limited to, porphyrins and porphyrin derivatives (e.g., chlorins, bacteriochlorins, isobacteriochlorins, phthalocyanines, and naphthalocyanines); metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid (R. W. Redmond and J. N. Gamlin, Photochem. Photobiol., 1999, 70: 391-475).

Exemplary photosensitizers suitable for use in the present invention include those described in U.S. Pat. Nos. 5,171,741; 5,171,749; 5,173,504; 5,308,608; 5,405,957; 5,512,675; 5,726,304; 5,831,088; 5,929,105; and 5,880,145 (the contents of each of which are incorporated herein by reference in their entirety).

Radiosensitizers

In certain embodiments, chlorotoxin conjugates comprise a radiosensitizer. As used herein, the term "radiosensitizer" refers to a molecule, compound or agent that makes tumor cells more sensitive to radiation therapy. Administration of a radiosensitizer to a patient receiving radiation therapy generally results in enhancement of the effects of radiation therapy. Ideally, a radiosensitizer exerts its function only on target cells. For ease of use, a radiosensitizer should also be able to find target cells even if it is administered systemically. However, currently available radiosensitizers are typically not selective for tumors, and they are distributed by diffusion in a mammalian body. Chlorotoxin conjugates of the present invention can be used as a new delivery system for radiosensitizers.

A variety of radiosensitizers are known in the art. Examples of radiosensitizers suitable for use in the present invention include, but are not limited to, paclitaxel (TAXOL®), carboplatin, cisplatin, and oxaliplatin (Amorino et al, Radiat. Oncol. Investig. 1999; 7: 343-352; Choy, Oncology, 1999, 13: 22-38; Safran et al., Cancer Invest., 2001, 19: 1-7; Dionet et al., Anticancer Res., 2002, 22: 721-725; Cividalli et al., Radiat. Oncol. Biol. Phys., 2002, 52: 1092-1098); gemcitabine (Gemzar®) (Choy, Oncology, 2000, 14: 7-14; Mornex and Girard, Annals of Oncology, 2006, 17: 1743-1747); etanidazole (Nitrolmidazole®) (Inanami et al., Int. J. Radiat. Biol., 2002, 78: 267-274); misonidazole (Tamulevicius et al., Br. J. Radiology, 1981, 54: 318-324; Palcic et al., Radiat. Res., 1984, 100: 340-347), tirapazamine (Masunaga et al., Br. J. Radiol., 2006, 79: 991-998; Rischin et al., J. Clin. Oncol., 2001, 19: 535-542; Shulman et al., Int. J. Radiat. Oncol. Biol. Phys., 1999, 44: 349-353); and nucleic acid base derivatives, e.g., halogenated purines or pyrimidines, such as 5-fluorodeoxyuridine (Buchholz et al., Int. J. Radiat. Oncol. Biol. Phys., 1995, 32: 1053-1058).

Radioisotopes

In certain embodiments, chlorotoxin conjugates comprise a radioisotope. Examples of suitable radioisotopes include any α-, β- or γ-emitter, which, when localized at a tumor site, results in cell destruction (S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (Eds.), Academic Press, 1985). Examples of such radioisotopes include, but are not limited to, iodine-131 ($^{131}$I), iodine-125 ($^{125}$I), bismuth-212 ($^{212}$Bi), bismuth-213 ($^{213}$Bi), astatine-211 ($^{211}$At), rhenium-186 ($^{186}$Re), rhenium-188 ($^{188}$Re), phosphorus-32 ($^{32}$P), yttrium-90 ($^{90}$yY), samarium-153 ($^{153}$Sm), and lutetium-177 ($^{177}$Lu).

Superantigens

In certain embodiments, chlorotoxin conjugates comprise a superantigen or biologically active portion thereof. Superantigens constitute a group of bacterial and viral proteins that are extremely efficient in activating a large fraction of the T-cell population. Superantigens bind directly to the major histocompatibility complex (MHC) without being processed. In fact, superantigens bind unprocessed outside the antigen-binding groove on the MHC class II molecules, thereby avoiding most of the polymorphism in the conventional peptide-binding site.

A superantigen-based tumor therapeutic approach has been developed for the treatment of solid tumors. In this approach, a targeting moiety, for example, an antibody or antibody fragment, is conjugated to a superantigen, providing a targeted superantigen. If the antibody, or antibody fragment, recognizes a tumor-associated antigen, the targeted superantigen, bound to tumors cells, can trigger superantigen-activated cytotoxic T-cells to kill the tumor cells directly by superantigen-dependent cell mediated cytotoxicity. (See, e.g., Søgaard et al. (1996) "Antibody-targeted superantigens in cancer immunotherapy," *Immunotechnology*, 2(3): 151-162, the entire contents of which are herein incorporated by reference.)

Superantigen-based tumor therapeutics have had some success. For example, fusion proteins with wild-type staphylococcal enterotoxin A (SEA) have been investigated in clinical trials of colorectal and pancreatic cancer (Giantonio et al., J. Clin. Oncol., 1997, 15: 1994-2007; Alpaugh et aL, Clin. Cancer Res., 1998, 4: 1903-1914; Cheng et aL, J. Clin. Oncol., 2004, 22: 602-609; the entire contents of each of which are herein incorporated by reference); staphylococcal superantigens of the enterotoxin gene cluster (egc) have been studied for the treatment of non-small cell lung cancer (Terman et al., Clin. Chest Med., 2006, 27: 321-324, the entire contents of which are herein incorporated by reference), and staphylococcal enterotoxin B has been evaluated for the intravesical immunotherapy of superficial bladder cancer (Perabo et al., Int. J. Cancer, 2005, 115: 591-598, the entire contents of which are herein incorporated by reference).

A superantigen, or a biologically active portion thereof, can be associated to a reduced lysine chlorotoxin polypeptide to form a chlorotoxin conjugate according to the present invention and used in a therapy, e.g., an anti-cancer therapy, as described herein.

Examples of superantigens suitable for use in the present invention include, but are not limited to, staphylococcal enterotoxin (SE) (e.g., staphylococcal enterotoxin A (SEA) or staphylococcal enterotoxin E (SEE)), *Streptococcus pyogenes* exotoxin (SPE), *Staphylococcus aureus* toxic shock-syndrome toxin (TSST-1), streptococcal mitogenic exotoxin (SME), streptococcal superantigen (SSA), and staphylococcal superantigens of the enterotoxin gene cluster. As known to one skilled in the art, the three-dimensional structures of the above listed superantigens can be obtained from the Protein Data Bank. Similarly, the nucleic acid sequences and the amino acid sequences of the above listed superantigens and other superantigens can be obtained from GenBank.

Prodrug Activating Enzymes

In certain embodiments, a chlorotoxin conjugate of the present invention may be used in directed enzyme prodrug therapy. In a directed enzyme prodrug therapy approach, a directed/targeted enzyme and a prodrug are administered to a subject, wherein the targeted enzyme is specifically localized to a portion of the subject's body where it converts the prodrug into an active drug. The prodrug can be converted to an active drug in one step (by the targeted enzyme) or in more than one step. For example, the prodrug can be converted to a precursor of an active drug by the targeted enzyme. The precursor can then be converted into the active drug by, for example, the catalytic activity of one or more additional targeted enzymes, one or more non-targeted enzymes administered to the subject, one or more enzymes naturally present in the subject or at the target site in the subject (e.g., a protease, phosphatase, kinase or polymerase), by an agent that is administered to the subject, and/or by a chemical process that is not enzymatically catalyzed (e.g., oxidation, hydrolysis, isomerization, epimerization, etc.).

Different approaches have been used to direct/target the enzyme to the site of interest. For example, in ADEPT (antibody-directed enzyme prodrug therapy), an antibody designed/developed against a tumor antigen is linked to an enzyme and injected in a subject, resulting in selective binding of the enzyme to the tumor. When the discrimination between tumor and normal tissue enzyme levels is sufficient, a prodrug is administered to the subject. The prodrug is converted to its active form by the enzyme only within the tumor. Selectivity is achieved by the tumor specificity of the antibody and by delaying prodrug administration until there is a large differential between tumor and normal tissue enzyme levels. Early clinical trials are promising and indicate that ADEPT may become an effective treatment for all solid cancers for which tumor-associated or tumor-specific antibodies are known. Tumors have also been targeted with the genes encoding for prodrug activating enzymes. This approach has been called virus-directed enzyme prodrug therapy (VDEPT) or more generally GDEPT (gene-directed enzyme prodrug therapy, and has shown good results in laboratory systems. Other versions of directed enzyme prodrug therapy include PDEPT (polymer-directed enzyme prodrug therapy), LEAPT (lectin-directed enzyme-activated prodrug therapy), and CDEPT (clostridial-directed enzyme prodrug therapy). A conjugate according to the present invention, which comprises a prodrug activating enzyme associated with a reduced lysine chlorotoxin polypeptide, can be used in a similar way.

Nonlimiting examples of enzyme/prodrug/active drug combinations suitable for use in the present invention are described, for example, in Bagshawe et al., Current Opinions in Immunology, 1999, 11: 579-583; Wilman, "Prodrugs in Cancer Therapy", Biochemical Society Transactions, 14: 375-382, 615$^{th}$ Meeting, Belfast, 1986; Stella et al., "*Prodrugs: A Chemical Approach To Targeted Drug Delivery*", in "*Directed Drug Delivery*", Borchardt et al., (Eds), pp. 247-267 (Humana Press, 1985). Nonlimiting examples of enzyme/prodrug/active anti-cancer drug combinations are described, for example, in Rooseboom et al., Pharmacol. Reviews, 2004, 56: 53-102.

Examples of prodrug activating enzymes include, but are not limited to, nitroreductase, cytochrome P450, purine-nucleoside phosphorylase, thymidine kinase, alkaline phosphatase, β-glucuronidase, carboxypeptidase, penicillin amidase, β-lactamase, cytosine deaminase, and methionine γ-lyase.

Examples of anti-cancer drugs that can be formed in vivo by activation of a prodrug by a prodrug activating enzyme include, but are not limited to, 5-(aziridin-1-yl)-4-hydroxylamino-2-nitro-benzamide, isophosphoramide mustard, phosphoramide mustard, 2-fluoroadenine, 6-methylpurine, ganciclovir-triphosphate nucleotide, etoposide, mitomycin C, p-[N,N-bis(2-chloroethyl)amino]phenol (POM), doxorubicin, oxazolidinone, 9-aminocamptothecin, mustard, methotrexate, benzoic acid mustard, doxorubicin, adriamycin, daunomycin, carminomycin, bleomycins, esperamicins, melphalan, palytoxin, 4-desacetylvinblastine-3-carboxylic acid hydrazide, phenylenediamine mustard, 4'-carboxyphthalato(1,2-cyclohexane-diamine) platinum, taxol, 5-fluorouracil, methylselenol, and carbonothionic difluoride.

b. Anti-Angiogenic Agents

In certain embodiments, a therapeutic (e.g., anti-cancer) agent within a chlorotoxin conjugate of the present invention comprises an anti-angiogenic agent. Antiangiogenic agents suitable for use in the present invention include any molecule, compound, or factor that blocks, inhibits, slows down, or reduces the process of angiogenesis, or the process by which new blood vessels form by developing from preexisting vessels. Such a molecule, compound, or factor can block angiogenesis by blocking, inhibiting, slowing down, or reducing any of the steps involved in angiogenesis, including (but not limited to) steps of (1) dissolution of the membrane of the originating vessel, (2) migration and proliferation of endothelial cells, and (3) formation of new vasculature by migrating cells.

Examples of anti-angiogenic agents include, but are not limited to, bevacizumab (AVASTIN®), celecoxib (CELEBREX®), endostatin, thalidomide, EMD121974 (Cilengitide), TNP-470, squalamine, combretastatin A4, interferon-α, anti-VEGF antibody, SU5416, SU6668, PTK787/2K 22584, Marimistal, AG3340, COL-3, Neovastat, and BMS-275291.

Anti-angiogenic agents may be used in a variety of therapeutic contexts, including, but not limited to, anti-cancer therapies and therapies for macular degeneration.

As will be recognized by one skilled in the art, the specific examples of therapeutic agents cited herein represent only a very small number of the therapeutic agents that are suitable for use in the practice of the present invention.

2. Detectable Entities/Moieties

In certain embodiments, provided conjugates comprise one or more detectable entities or moieties, i.e., conjugates are "labeled" with such entities or moieties. In some such embodiments, such conjugates are useful in diagnostic applications.

Any of a wide variety of detectable agents can be used in the practice of the present invention. Suitable detectable agents include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

a. Radioactive and/or Paramagnetic Isotopes or Ions

In certain embodiments, a reduced lysine chlorotoxin polypeptide is labeled with a radioactive and/or paramagnetic isotope or ion. For example, a reduced lysine chlorotoxin polypeptide may be isotopically-labeled (i.e., may contain one or more atoms that have been replaced by an atom having an atomic mass or mass number different from the atomic mass or mass number usually found in nature) or an isotope may be attached to the reduced lysine chlorotoxin polypeptide. Non-limiting examples of isotopes that can be incorporated into reduced lysine chlorotoxin polypeptides include isotopes of hydrogen, carbon, fluorine, phosphorous, copper, gallium, yttrium, technetium, indium, iodine, rhenium, thallium, bismuth, astatine, samarium, and lutetium (i.e., $^{3}H$, $^{13}C$, $^{14}C$, $^{18}F$, $^{32}P$, $^{35}S$, $^{64}Cu$, $^{67}Ga$, $^{90}Y$, $^{99m}Tc$, $^{111}In$, $^{125}I$, $^{123}I$, $^{129}I$, $^{131}I$, $^{135}I$, $^{186}Re$, $^{187}Re$, $^{201}Tl$, $^{212}Bi$, $^{211}At$, $^{153}Sm$, $^{177}Lu$).

In certain embodiments, reduced lysine chlorotoxin polypeptides comprise a radioisotope that is detectable by Single Photon Emission Computed Tomography (SPECT) or Position Emission Tomography (PET). Examples of such radionuclides include, but are not limited to, iodine-131 ($^{131}I$), iodine 125 ($^{125}I$), bismuth-212 ($^{212}Bi$), bismuth-213 ($^{213}Bi$), astatine-221 ($^{221}At$), copper-67 ($^{67}Cu$), copper-64 ($^{64}Cu$), rhenium-186 ($^{186}Re$), rhenium-188 ($^{118}Re$), phosphorus-32 ($^{32}P$), samarium-153 ($^{153}Sm$), lutetium-177 ($^{177}Lu$), technetium-99m ($^{99m}Tc$), gallium-67 ($^{67}Ga$), indium-111 ($^{111}In$), and thallium-201 ($^{201}Tl$).

In certain embodiments, a reduced lysine chlorotoxin polypeptide is labeled with a radioisotope that is detectable by Gamma camera. Examples of such radioisotopes include, but are not limited to, iodine-131 ($^{131}I$), and technetium-99m ($^{99m}Tc$).

In certain embodiments, a reduced lysine chlorotoxin polypeptide is labeled with a paramagnetic metal ion that is a good contrast enhancer in Magnetic Resonance Imaging (MRI). Examples of such paramagnetic metal ions include, but are not limited to, gadolinium III (Gd3+), chromium III (Cr3+), dysprosium III (Dy3+), iron III (Fe3+), manganese II (Mn2+), and ytterbium III (Yb3+). In certain embodiments, the labeling moieties comprises gadolinium III (Gd3+). Gadolinium is an FDA-approved contrast agent for MRI, which accumulates in abnormal tissues causing these abnormal areas to become very bright (enhanced) on the magnetic resonance image. Gadolinium is known to provide great contrast between normal and abnormal tissues in different areas of the body, in particular in the brain.

In certain embodiments, a reduced lysine chlorotoxin polypeptide is labeled with a stable paramagnetic isotope detectable by nuclear magnetic resonance spectroscopy (MRS). Examples of suitable stable paramagnetic isotopes include, but are not limited to, carbon-13 ($^{13}C$) and fluorine-19 ($^{19}F$).

In some embodiments, metal isotopes are non-covalently attached to the reduced lysine chlorotoxin conjugate by chelation. Examples of chelation include chelation of a metal isotope to a poly-His region fused to a reduced lysine chlorotoxin polypeptide.

In some embodiments, a metal such as gadolinium (Gd) is incorporated into a reduced lysine chlorotoxin polypeptide either through covalent bonding or through chelation, as described above.

b. Fluorescent Dyes

In certain embodiments, a reduced lysine chlorotoxin polypeptide is labeled with a fluorescent dye. Numerous known fluorescent dyes of a wide variety of chemical structures and physical characteristics are suitable for use in the practice of the present invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514., etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/

570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", $9^{th}$ Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

c. Enzymes

In certain embodiments, a reduced lysine chlorotoxin polypeptide is labeled with an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a reduced lysine chlorotoxin polypeptide using a linker group such as a carbodiimide, a diisocyanate, a glutaraldehyde, and the like.

It will be recognized by those of ordinary skill in the art that in some embodiments, a particular non-chlorotoxin entity or moiety may serve more than one purpose. For example, a moiety may have both a therapeutic purpose and a diagnostic purpose. To give but one example, radioactive iodine such as $^{131}I$ has been used as both a radiolabel and a cytotoxic therapeutic agent within a chlorotoxin conjugate in the treatment of a variety of tumors including malignant glioma.

III. Pharmaceutical Compositions

Chlorotoxin conjugates described herein may be administered per se and/or in the form of a pharmaceutical composition. In some embodiments, provided are pharmaceutical compositions comprising an effective amount of at least one chlorotoxin conjugate and at least one pharmaceutically acceptable carrier.

A chlorotoxin conjugate, or a pharmaceutical composition thereof, may be administered according to the present invention in such amounts and for such a time as is necessary or sufficient to achieve at least one desired result. For example, an inventive pharmaceutical composition can be administered in such amounts and for such a time that it kills cancer cells, reduces tumor size, inhibits tumor growth or metastasis, treats various leukemias, and/or prolongs the survival time of mammals (including humans) with those diseases, or otherwise yields clinical benefit.

Pharmaceutical compositions of the present invention may be administered using any amount and any route of administration effective for achieving the desired therapeutic effect.

The exact amount of pharmaceutical composition to be administered will vary from subject to subject, depending on the species, age, and general condition of the subject, the severity of the condition, and the like (see below).

The optimal pharmaceutical formulation can be varied depending upon the route of administration and desired dosage. Such formulations may influence the physical state, stability, rate of in vivo release, and rate of in vivo clearance of the administered compounds.

Pharmaceutical compositions of the present invention may be formulated in dosage unit form for ease of administration and uniformity of dosage. The expression "unit dosage form", as used herein, refers to a physically discrete unit of chlorotoxin conjugate (with or without one or more additional agents) for the patient to be treated. It will be understood, however, that the total daily usage of compositions of the present invention will be decided by the attending physician within the scope of sound medical judgment.

After formulation with one or more appropriate physiologically acceptable carrier(s) or excipient(s) in a desired dosage, pharmaceutical compositions of the present invention can be administered to humans or other mammals by any suitable route. Various delivery systems are known and can be used to administer such compositions, including, tablets, capsules, injectable solutions, etc. Methods of administration include, but are not limited to, dermal, intradermal, intramuscular, intraperitoneal, intravenous, subcutaneous, intranasal, pulmonary, epidural, ocular, and oral routes. A composition may be administered by any convenient or otherwise appropriate route, for example, by infusion or bolus injection, by absorption through epithelial or mucocutaneous linings (e.g., oral, mucosa, rectal and intestinal mucosa, etc) and may be administered together with other biologically active agents. Administration can be systemic and/or local.

Injectable preparations, for example, sterile injectable aqueous or oleaginous suspensions, may be formulated according to the known art using suitable dispersing or wetting agents, and suspending agents. A sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid from compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion (e.g., 30 minute intravenous infusion). Where necessary, the composition may include a local anesthetic to ease pain at the site of injection.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming micro-encapsuled matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes (also known as lipid vesicles) or microemulsions that are compatible with body tissues.

Liquid dosage forms for oral administration include, but are not limited to, pharmaceutically acceptable emulsions, microemulsions, solutions, suspensions, syrups, elixirs, and pressurized compositions. In addition to the active ingredient (i.e., conjugate), the liquid dosage form may contain inert diluents commonly used in the art such as, for example, water or other solvent, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, suspending agents, preservatives, sweetening, flavoring, and perfuming agents, thickening agents, colors, viscosity regulators, stabilizers or osmoregulators. Suitable examples of liquid carriers for oral administration include water (partially containing additives as above; e.g., cellulose derivatives, such as sodium caboxymethyl cellulose solution), alcohols (including monohydric alcohols and polyhydric alcohols such as glycols) and their derivatives, and oils (e.g., fractionated coconut oil and arachis oil)).

Solid dosage forms for oral administration include, for example, capsules, tablets, pills, powders, and granules. In such solid dosage forms, the active ingredient is mixed with at least one inert, physiologically acceptable excipient or carrier such as sodium citrate or dicalcium phosphate and one or more of: (a) fillers or extenders such as starches, lactose, sucrose, glucose, mannitol, and silicic acid; (b) binders such as, for example, carboxymethylcellulose, alginates, gelatin, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulfate, and mixtures thereof. Additional or alternative excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents. The amount of solid carrier per solid dosage form will vary widely. In some embodiments, the amount of solid carrier per solid dosage form is from about 25 mg to about 1 g.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

In certain embodiments, it may be desirable to administer an inventive composition locally to an area in need of treatment. This may be achieved, for example, by local infusion during surgery, topically application, by injection, by means of a catheter, by means of suppository, or by means of a skin patch or stent or other implant, among other ways.

Some compositions for topical administration may be formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurate (5%) in water, or sodium lauryl sulfate (5%) in water. Other materials such as antioxidants, humectants, viscosity stabilizers, and similar agents may be added as necessary. Percutaneous penetration enhancers such as Azone may also be included.

In addition, in certain instances, compositions may be disposed within transdermal devices placed upon, in, or under the skin. Such devices include patches, implants, and injections which release the compound onto the skin, by either passive or active release mechanisms. Transdermal administrations include all administrations across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished, for example, through use of a transdermal patch containing active ingredient(s) and a carrier that is non-toxic to the skin, and allows the delivery of at least some of the active ingredient(s) for systemic absorption into the bloodstream via the skin. The carrier may take any number of forms such as creams and ointments, pastes, gels, and occlusive devices. Creams and ointments may be viscous liquid or semisolid emulsions of either the oil-in-water or water-in-oil type. Pastes comprised of absorptive powders dispersed in petroleum or hydrophilic petroleum containing active ingredient(s) may also be suitable.

A variety of occlusive devices may be used to release active ingredient(s) into the bloodstream such as a semipermeable membrane covering a reservoir containing the active ingredient(s) with or without a carrier, or a matrix containing the active ingredient.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

Materials and methods for producing various formulations are known in the art and may be adapted for practicing the subject invention.

Encapsulating Agents

In some embodiments, compositions provided by the present invention include one or more encapsulating agents. In general, an encapsulating agent can be any physiologically tolerable agent that can be used to entrap an entity such as a conjugate or a moiety. By "entrapped" it is meant that the encapsulating agent may encircle or enclose the entity, or an "entrapped" entity may be embedded partially or wholly within the material comprising the encapsulating agent.

In some embodiments, the encapsulating agent is part of the moiety (such as therapeutic moiety), and the reduced lysine chlorotoxin polypeptide is conjugated to the encapsulating agent. In some such embodiments, the reduced lysine chlorotoxin polypeptide is conjugated to the outer surface of the encapsulating agent. In some such embodiments, the reduced lysine chlorotoxin polypeptide is exposed on the environment external to the encapsulating agent. The reduced lysine chlorotoxin polypeptide may be conjugated to the encapsulating agent by a direct interaction (which may be non-covalent or covalent), or it may be conjugated to the encapsulating agent via a linker.

In some embodiments, the conjugate comprising the reduced lysine chlorotoxin polypeptide and the moiety (e.g., therapeutic moiety) is enclosed by the encapsulating agent. The conjugate may be enclosed partially or wholly within a space or environment (for example, an aqueous environment) defined and/or created by the encapsulating agent. In some embodiments, the conjugate is at least partially embedded within the encapsulating agent. For example, if the encapsulating agent comprises lipid membranes, the conjugate may be at least partially embedded within or among lipid molecules in the membrane. In some embodiments, the conjugate is wholly embedded within the encapsulating agent.

A variety of types of encapsulating agents are known in the art, as are methods of using such agents to entrap drugs, biomolecules, and the like. In certain embodiments, the encapsulating agent comprises a small particle having a core and a surface. Such encapsulating agents include, but are not limited to, liposomes, micelles, microparticles, nanoparticles, etc.

Liposomes are typically approximately spherically shaped bilayer structures or vesicles and comprised of natural or synthetic phospholipid membranes. Liposomes may further comprise other membrane components such as cholesterol and protein. The interior core of liposomes typically contain an aqueous solution. Therapeutic agents and/or conjugates may be dissolved in the aqueous solution. As previously mentioned, therapeutic agents and conjugates may be embedded within the membrane of the liposome. Liposomes may be especially useful for delivering agents such as nucleic acid agents (such as those described above), including inhibitory RNAs such as siRNAs.

Micelles are similar to liposomes, except they generally form from a single layer of phospholipids and lack an internal aqueous solution. Reverse micelles that are made to include internal aqueous solution may also be used in accordance with the present invention.

In some embodiments, the particle is a microparticle, at least one dimension of which averages to be smaller than about 1 μm. For example, the smallest dimension of the particles can average about 100 nm, about 120 nm, about 140 nm, about 160 nm, about 180 nm, about 200 nm, about 220 nm, about 240 nm, about 260 nm, about 280 nm, about 300 nm, about 320 nm, about 340 nm, about 360 nm, about 380 nm, about 400 nm, about 420 nm, about 440 nm, about 460 nm, about 480 nm, about 500 nm, about 550 nm, about 600 nm, about 650 nm, about 700 nm, about 750 nm, about 800 nm, about 850 nm, about 900 nm, or about 950 nm.

In some embodiments, the particle is a nanoparticle, at least one dimension of which averages to be smaller than about 100 μm. For example, the smallest dimension of the particles can average about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 22 nm, about 24 nm, about 26 nm, about 28 nm, about 30 nm, about 32 nm, about 34 nm, about 36 nm, about 38 nm, about 40 nm, about 42 nm, about 44 nm, about 46 nm, about 48 nm, about 50 nm, about 55 nm, about 60 nm, about 65 nm, about 70 nm, about 75 nm, about 80 nm, about 85 nm, about 90 nm, about 95 nm, or about 99 nm.

In some embodiments, the core of the particle comprises a material having magnetic resonance activity, which may advantageous in diagnostic and/or therapeutic applications. Materials having magnetic resonance activity include metals and their oxides, such as aluminum-cobalt-, indium-, iron-, copper-, germanium-, manganese-, nickel-, tin-, titanium-, palladium-, platinum-, selenium-, silicon-, silver-, zinc-, etc. containing metals.

In some embodiments, therapeutic agents comprise nucleic acids. Nucleic acids may be enclosed wholly within the encapsulating agent. In some embodiments, nucleic acid agents are embedded within the encapsulating agent. For example, the encapsulating agent may be a liposome and the nucleic agent may be enclosed within the liposome. The nucleic acid agent may be at least partially embedded within the lipid molecules of the liposome.

Pharmaceutical Packs or Kits

In another aspect, the present invention provides a pharmaceutical pack or kit comprising one or more containers (e.g., vials, ampoules, test tubes, flasks or bottles) containing one or more ingredients of a pharmaceutical composition as described herein, allowing administration of a chlorotoxin conjugate of the present invention.

IV. Methods of Using Chlorotoxin Conjugates

In certain embodiments, provided are methods comprising the step of administering a composition comprising a chlorotoxin conjugate as described herein to an individual having or suspected of having a tumor, such that the conjugate binds specifically to the tumor. In some embodiments, such methods are useful in treatment and/or diagnosis of cancer. In some embodiments, such methods are useful in reducing the likelihood that the individual will develop a tumor, that one or more tumors in the individual will increase in size, that one or more tumors in the individual will metastasize, and/or that the cancer will progress by any other measure (such as clinical stage).

In certain embodiments, provided are methods comprising the step of administering a composition comprising a chlorotoxin conjugate as described herein to an individual having or suspected of having a disease or condition characterized by aberrant angiogenesis, such that the chlorotoxin conjugate reduces extent of angiogenesis. In some embodiments, the chlorotoxin conjugate prevents the formation of neovasculature. In some embodiments, the chlorotoxin conjugate causes existing neovasculature to regress.

A. Dosages and Administration

Compositions according to the present invention may be administered according to a regimen consisting of a single dose or a plurality of doses over a period of time.

Chlorotoxin conjugates, or pharmaceutical compositions thereof, may be administered using any administration route effective for achieving the desired effect (e.g., therapeutic, diagnostic, etc.). In certain embodiments of the invention, chlorotoxin conjugates (or pharmaceutical compositions thereof) are delivered systemically. Typical systemic routes of administration include, but are not limited to, intramuscular, intravenous, pulmonary, and oral routes. Systemic administration may also be performed, for example, by infusion or bolus injection, or by absorption through epithelial or mucocutaneous linings (e.g., oral, mucosa, rectal and intestinal mucosa, etc). In certain embodiments, the chlorotoxin conjugate is administered intravenously.

Alternatively or additionally, other routes of administration may also be used. In certain embodiments, the chlorotoxin conjugate is administered by a route selected from the group consisting of intravenous, intracranial (including intracavitary), intramuscular, intratumoral, subcutaneous, intraocular, periocular, topical application, or by combinations thereof.

As discussed below, it may be desirable to reduce extent of angiogenesis in ocular neovascularization diseases. In some embodiments, chlorotoxin conjugates may be delivered to the eye. Delivery to the eye may be achieved, for example, using intraocular and/or periocular routes such as intravitreal injection, subjunctival injection, etc. Topical application of chlorotoxin agents to the eye may also be achieved, for example, using eye drops.

Ocular routes of administration may be particularly useful for treatment of ocular neovascularization diseases such as macular degeneration.

Administration may be one or multiple times daily, weekly (or at some other multiple day interval) or on an intermittent schedule. For example, a composition may be administered one or more times per day on a weekly basis for a period of weeks (e.g., 4-10 weeks). Alternatively, a composition may be administered daily for a period of days (e.g., 1-10 days) following by a period of days (e.g., 1-30 days) without administration, with that cycle repeated a given number of times (e.g., 2-10 cycles). In some embodiments, at least two, at least three, at least four, at least five, or at least six doses are administered. In some embodiments, the composition is administered weekly for at least two weeks, three weeks, four weeks, five weeks, or six weeks.

Administration may be carried out in any convenient manner, or in any combination of manners, such as by injection (subcutaneous, intravenous, intramuscular, intraperitoneal, or the like), oral administration, and/or intracavitary administration.

Depending on the route of administration, effective doses may be calculated according to the organ function, body weight, or body surface area of the subject to be treated. Optimization of the appropriate dosages can readily be made by one skilled in the art in light of pharmacokinetic data observed in human clinical trials. Final dosage regimen may be determined by the attending physician, considering various factors that modify the action of the drugs, e.g., the drug's specific activity, the severity of the damage and the responsiveness of the patient, the age, condition, body weight, sex and diet of the patient, the severity of any present infection, time of administration, the use (or not) of concomitant therapies, and other clinical factors.

Typical dosages range from about 1.0 pg/kg body weight to about 100 mg/kg body weight. (Dosages are presented herein in terms of the weight of the reduced lysine chlorotoxin polypeptide part of the conjugate.)

For example, for systemic administration, typical dosages range from about 100.0 ng/kg body weight to about 10.0 mg/kg body weight. For example, in certain embodiments where a chlorotoxin conjugate is administered intravenously, dosing of the agent may comprise administration of one or more doses comprising about 0.001 mg/kg to about 5 mg/kg, e.g., from about 0.001 mg/kg to about 5 mg/kg, from about 0.01 mg/kg to about 4 mg/kg, from about 0.02 mg/kg to about 3 mg/kg, from about 0.03 mg/kg to about 2 mg/kg or from about 0.03 mg/kg to about 1.5 mg/kg of chlorotoxin. For example, in some embodiments, one or more doses of chlorotoxin conjugate may be administered that each contains about 0.002 mg/kg, about 0.004 mg/kg, about 0.006 mg/kg, about 0.008 mg/kg, about 0.009 mg/kg, about 0.01 mg/kg, about 0.02 mg/kg or more than 0.02 mg/kg of chlorotoxin. In some embodiments, one or more doses of chlorotoxin conjugate may be administered that each contains about 0.03 mg/kg, about 0.04 mg/kg, about 0.05 mg/kg, about 0.06 mg/kg, about 0.07 mg/kg, about 0.09 mg/kg, about 1.0 mg/kg or more than 1.0 mg/kg of chlorotoxin. In some embodiments, one or more doses of chlorotoxin conjugate may be administered that each contains about 0.05 mg/kg, about 0.10 mg/kg, about 0.15 mg/kg, about 0.20 mg/kg, about 0.25 mg/kg, about 0.30 mg/kg, about 0.35 mg/kg, about 0.40 mg/kg, about 0.45 mg/kg, about 0.50 mg/kg, about 0.55 mg/kg, about 0.60 mg/kg, about 0.65 mg/kg, about 0.70 mg/kg, about 0.75 mg/kg, about 0.80 mg/kg, about 0.85 mg/kg, about 0.90 mg/kg, about 0.95 mg/kg, about 1.0 mg/kg, or more than about 1 mg/kg of chlorotoxin. In yet other embodiments, one or more doses of chlorotoxin conjugate may be administered that each contains about 1.0 mg/kg, about 1.05 mg/kg, about 1.10 mg/kg, about 1.15 mg/kg, about 1.20 mg/kg, about 1.25 mg/kg, about 1.3 mg/kg, about 1.35 mg/kg, about 1.40 mg/kg, about 1.45 mg/kg, about 1.50 mg/kg, or more than about 1.50 mg/kg of chlorotoxin. In such embodiments, at treatment may comprise administration of a single dose of chlorotoxin conjugate or administration of 2 doses, 3 doses, 4 doses, 5 doses, 6 doses or more than 6 doses. Two consecutive doses may be administered at 1 day interval, 2 days interval, 3 days interval, 4 days interval, 5 days interval, 6 days interval, 7 days interval, or more than 7 days interval (e.g., 10 days, 2 weeks, or more than 2 weeks).

For direct administration to the site via microinfusion, typical dosages range from about 1 ng/kg body weight to about 1 mg/kg body weight.

In certain embodiments where the chlorotoxin conjugate is administered locally, in particular in cases of intracavitary administration to the brain, dosing of the conjugate may comprise administration of one or more doses comprising about 0.01 mg to about 100 mg of chlorotoxin polypeptide, e.g., from about 0.05 to about 50 mg, from about 0.1 mg to about 25 mg, from about 0.1 mg to about 10 mg, from about 0.1 mg to about 5 mg, or from about 0.1 mg to about 1.0 mg. For example, in certain embodiments, one or more doses of chlorotoxin conjugate may be administered that each contains about 1 mg, about 1.5 mg, about 2 mg, about 2.5 mg, about 3 mg, about 3.5 mg, about 4 mg, about 4.5 mg or about 5 mg of reduced lysine chlorotoxin polypeptide. In some embodiments, one or more doses of chlorotoxin conjugate may be administered that each contains about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg or about 1 mg of reduced lysine chlorotoxin polypeptide. In some embodiments, a treatment may comprise administration of a single dose of chlorotoxin conjugate or administration of 2 doses, 3 doses, 4 doses, 5 doses, 6 doses or more than 6 doses. Two consecutive doses may be administered at 1 day interval, 2 days interval, 3 days interval, 4 days interval, 5 days interval, 6 days interval, 7 days interval, or more than 7 days interval (e.g., 10 days, 2 weeks, or more than 2 weeks). In some embodiments, multiple doses are administered, and the amount of reduced lysine chlorotoxin polypeptide administered is not the same for every dose. For example, in some embodiments, doses may be adjusted (e.g., escalated or reduced) from one dose to another as determined by the attending clinician.

It will be appreciated that pharmaceutical combinations of the present invention can be employed in combination with additional therapies (i.e., a treatment according to the present invention can be administered concurrently with, prior to, or subsequently to one or more desired therapeutics or medical procedures). The particular combination of therapies (therapeutics and/or procedures) to employ in such a combination regimen will take into account compatibility of the desired therapeutics and/or procedures and the desired therapeutic effect to be achieved.

For example, methods and compositions of the present invention can be employed together with other procedures including surgery, radiotherapy (e.g., γ-radiation, proton beam radiotherapy, electron beam radiotherapy, proton therapy, brachytherapy, and systemic radioactive isotopes), endocrine therapy, hyperthermia and cryotherapy.

Alternatively or additionally, methods and compositions of the present invention can be employed together with other agents to attenuate any adverse effects (e.g., antiemetics), and/or with other approved chemotherapeutic drugs, including, but not limited to, alkylating drugs (mechlorethamine, chlorambucil, cyclophosphamide, melphalan, ifosfamide), antimetabolites (methotrexate), purine antagonists and pyrimidine antagonists (6-mercaptopurine, 5-fluorouracil, cytarabile, gemcitabine), spindle poisons (vinblastine, vincristine, vinorelbine, paclitaxel), podophyllotoxins (etoposide, irinotecan, topotecan), antibiotics (doxorubicin, bleomycin, mitomycin), nitrosoureas (carmustine, lomustine), inorganic ions (cisplatin, carboplatin), enzymes (asparaginase), and hormones (tamoxifen, leuprolide, flutamide, and megestrol), to name a few. For a more comprehensive discussion of updated cancer therapies see <www.cancer.gov>, a list of the FDA approved oncology drugs at <www.fda.gov/cder/cancer/druglistfframe.htm>, and The Merck Manual, Seventeenth Ed. 1999, the entire contents of which are hereby incorporated by reference.

Methods and compositions of the present invention can also be employed together with one or more further combinations of cytotoxic agents as part of a treatment regimen. In some embodiments, the further combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and pro carb azine); AB VD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); Ch1VPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

B. Indications

Compositions and methods of the present invention can be used in a variety of antiproliferative and/or antiangiogenic contexts to treat and/or diagnose diseases or conditions.

1. Anti-Proliferative Contexts

In certain embodiments, compositions and methods of the present invention are used to treat and/or diagnose conditions involving uncontrolled cell proliferation, such as primary and/or metastatic cancers, and other cancerous conditions. For example, compositions and methods of the present invention should be useful for reducing size of solid tumors, inhibiting tumor growth or metastasis, treating various lymphatic cancers, and/or prolonging the survival time of mammals (including humans) suffering from these diseases.

Examples of cancers and cancer conditions that can be treated and/or diagnosed according to the present invention include, but are not limited to, tumors of the brain and central nervous system (e.g., tumors of the meninges, brain, spinal cord, cranial nerves and other parts of the CNS, such as glioblastomas or medulloblastomas); head and/or neck cancer, breast tumors, tumors of the circulatory system (e.g., heart, mediastinum and pleura, and other intrathoracic organs, vascular tumors, and tumor-associated vascular tissue); tumors of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, haematopoietic and related tissues, such as diffuse large cell lymphoma, T-cell lymphoma or cutaneous T-cell lymphoma); tumors of the excretory system (e.g., kidney, renal pelvis, ureter, bladder, and other urinary organs); tumors of the gastrointestinal tract (e.g., esophagus, stomach, small intestine, colon, colorectal, rectosigmoid junction, rectum, anus, and anal canal); tumors involving the liver and intrahepatic bile ducts, gall bladder, and other parts of the biliary tract, pancreas, and other digestive organs; tumors of the oral cavity (e.g., lip, tongue, gum, floor of mouth, palate, parotid gland, salivary glands, tonsil, oropharynx, nasopharynx, puriform sinus, hypopharynx, and other sites of the oral cavity); tumors of the reproductive system (e.g., vulva, vagina, Cervix uteri, uterus, ovary, and other sites associated with female genital organs, placenta, penis, prostate, testis, and other sites associated with male genital organs); tumors of the respiratory tract (e.g., nasal cavity, middle ear, accessory sinuses, larynx, trachea, bronchus and lung, such as small cell lung cancer and non-small cell lung cancer); tumors of the skeletal system (e.g., bone and articular cartilage of limbs, bone articular cartilage and other sites); tumors of the skin (e.g., malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneoum and peritoneum, eye and adnexa, thyroid, adrenal gland, and other endocrine glands and related structures, secondary and unspecified malignant neoplasms of lymph nodes, secondary malignant neoplasm of respiratory and digestive systems and secondary malignant neoplasms of other sites.

In some embodiments, the tumor is cutaneous or intraocular melanoma. In some embodiments, the tumor is metastatic melanoma. In some embodiments, the tumor is non-small cell lung cancer. In some embodiments, the tumor is colon or colorectal cancer.

In some embodiments, compositions and methods are useful in the treatment and/or diagnosis of neuroectodermal tumors. (See, e.g., U.S. Pat. No. 6,667,156; the entire contents of which are herein incorporated by reference.) In some embodiments, the neuroectodermal tumor is glioma. (See, e.g., U.S. Pat. Nos. 5,905,027; 6,028,174; 6,319,891; 6,429,187; and 6,870,029; and International Patent Application publications WO03/101475A2, WO09/021136A1, and WO 2009/140599; the entire contents of each of which are herein incorporated by reference.) Types of glioma for which compositions and methods of the invention are useful include, but are not limited to, glioblastoma multiformes (WHO grad IV), anaplastic astrocytomas (WHO grade III), low grade gliomas (WHO grade II), pliocytic astrocytomas (WHO grade I), oligodendrogliomas, gangliomas, meningiomas, and ependymomas. In some embodiments, the neuroectodermal tumor is selected from the group consisting of medulloblastomas, neuroblastomas, pheochromocytomas, melanomas, peripheral primitive neuroectodermal tumors, small cell carcinoma of the lung, Ewing's sarcoma, and metastatic tumors in the brain.

In certain embodiments of the present invention, compositions and methods are used in the treatment and/or diagnosis of sarcomas. In some embodiments, compositions and methods of the present invention are used in the treatment and/or diagnosis of bladder cancer, breast cancer, chronic lymphoma leukemia, head and neck cancer, endometrial cancer, Non-Hodgkin's lymphoma, non-small cell lung cancer, ovarian cancer, pancreatic cancer, and prostate cancer. In some embodiments, the sarcoma is selected from the group consisting of prostate cancer or breast cancer. (See, e.g., International Patent Application publications W003/101474A1, W003/10475A2, and WO 2009/140599, the entire contents of each of which are herein incorporated by reference.) In some embodiments, the sarcoma is pancreatic cancer.

In certain embodiments of the present invention, compositions and methods are useful in the treatment and/or diagnosis of myeloproliferative disorders (e.g., tumors of myeloid origin) and/or lymphoproliferative disorders (e.g., tumors of lymphoid origin). (See, e.g., International Patent Application publication WO05/099774, the entire contents of which are herein incorporated by reference.)

Types of myeloproliferative disorders for which compositions and methods of the present invention are useful include, but are not limited to, polycythemia vera (PV), essential thrombocythemia (ET), agnogenic myeloid metaplasia (AMM) (also referred to as idiopathic myelofibrosis (IMF)), and chronic myelogenous leukemia (CML).

In some embodiments, compositions and methods of the present invention are used to treat and/or diagnose a lymphoproliferative disorder. In some embodiments, the lymphoproliferative disorder is a non-Hodgkin's lymphoma. In some embodiments, the lymphoproliferative disorder is a B cell neoplasm, such as, for example, a precursor B-cell lymphoblastic leukemia/lymphoma or a mature B cell neoplasm. Non-limiting types of mature B cell neoplasms include B cell chronic lymphocytic leukemia/small lymphocytic lymphoma, B cell prolymphocytic leukemia, lymphoplasmacytic lymphoma, splenic marginal zone B cell lymphoma, hairy cell leukemia, extranodal marginal zone B cell lymphoma, mantle cell lymphoma, follicular lymphoma, nodal marginal zone lymphoma, diffuse large B cell lymphoma, Burkitt's lymphoma, plasmacytoma, and plasma cell myeloma.

In some embodiments, compositions and methods of the present invention are used to treat a T cell neoplasm. Non-limiting types of T cell neoplasms include T cell prolymphocytic leukemia, T cell large granular lymphocytic leukemia, NK cell leukemia, extranodal NK/T cell lymphoma, mycosis fungoides, primary cutaneous anaplastic large cell lymphoma, subcutaneous panniculitis-like T cell lymphoma, enteropathy-type intestinal T cell lymphoma, hepatosplenic gamma-delta T cell lymphoma, angioimmunoblastic T cell lymphoma, peripheral T cell lymphoma, anaplastic large cell lymphoma, and adult T cell lymphoma.

Tumors that can be treated using compositions and methods of the present invention may be refractory to treatment with other chemotherapeutics. The term "refractory", when used herein in reference to a tumor means that the tumor (and/or metastases thereof), upon treatment with at least one chemotherapeutic other than an inventive composition, shows no or only weak anti-proliferative response (i.e., no or only weak inhibition of tumor growth) after the treatment of such a chemotherapeutic agent—that is, a tumor that cannot be treated at all or only with unsatisfying results with other (preferably standard) chemotherapeutics. The present invention, where treatment of refractory tumors and the like is mentioned, is to be understood to encompass not only (i) tumors where one or more chemotherapeutics have already failed during treatment of a patient, but also (ii) tumors that can be shown to be refractory by other means, e.g., biopsy and culture in the presence of chemotherapeutics.

2. Anti-Angiogenic Contexts

Chlorotoxin has been shown to exert anti-angiogenic properties. See, e.g., International Patent Application publication WO2009/117018, the entire contents of which are herein incorporated by reference. In certain embodiments, compositions and methods of the present invention are used to treating, diagnose, and/or ameliorate a disease or condition such as, for example cancer (including metastatic cancer, as described above), ocular neovascularization (such as macular degeneration), inflammatory diseases (such as arthritis), etc. In some embodiments, the condition or disease is characterized by choroidal neovascularization. Examples of such conditions or diseases include, but are not limited to, macular degeneration (including wet macular degeneration, age-related macular degeneration, etc.), myopia, ocular trauma, pseudoxanthoma elasticum, and combinations thereof.

Macular degeneration is the leading cause of vision loss and blindness in Americans aged 65 and older. Macular degeneration typically occurs in the age-related form (often called AMD or ARMD), though juvenile macular degeneration occurs as well. In AMD/ARMD, the macula—the part of the retina that is responsible for sharp, central vision—degenerates. Macular degeneration is typically diagnosed as either dry (non-neovascular) or wet (neovascular).

In dry macular degeneration, yellowish spots known as drusen begin to accumulate from deposits or debris from deteriorating tissue from mostly around the macula. Central vision less usually occurs gradually and is not as severe as vision loss in wet macular degeneration.

Wet macular degeneration, as the "neovascular" designation suggests, is characterized by new blood vessels growing aberrantly, e.g., on the macula. Such new blood vessels may grow beneath the retina, leaking blood and fluid. Such leakage causes permanent damage to light-sensitive retinal cells, which die and create blind spots in central vision. Wet macular degeneration may be further grouped into two categories. In the occult form of wet macular degeneration, new blood vessel growth beneath the retina is not as pronounced and leakage is less evident, typically resulting in less severe vision less. In the classic form of wet macular degeneration, blood vessel growth and scarring have very clear, delineated outlines that are observable beneath the retina. Classic wet macular degeneration is also known as classic choroidal neovascularization and usually results in more severe vision loss.

Given the role of angiogenesis in wet macular degeneration, which comprises many AMD/ARMD cases, inventive compositions and methods may be useful in treating, diagnosing, and/or ameliorating such disorders. Current therapies for wet macular degeneration involve angiogenesis inhibitors such as Lucentis™, Macugen™, and/or Visudyne™, optionally combined with photodynamic therapy (PDT) to target drugs to specific cells. Photocoagulation, in which a high energy laser beam is used to create small burns in areas of the retina with abnormal blood vessels, is also used to treat wet macular degeneration.

In some embodiments, chlorotoxin conjugates (or a pharmaceutical composition thereof) are administered to a subject suffering from wet macular degeneration and/or age-related macular degeneration. Among subjects suffering from wet macular degeneration, subjects may suffer from the occult or the classic form. In some embodiments, chlorotoxin conjugates cause regression of existing neovasculature. In some embodiments, chlorotoxin conjugates prevent sprouting of new vessels. In certain embodiments, chlorotoxin conjugates are combined with other treatments for wet macular degeneration, such as photocoagulation, treatment with other angiogenesis inhibitors, photodynamic therapy, etc.

In some embodiments, chlorotoxin agents as described herein are administered in combination with or as part of a therapeutic regimen with one or more therapeutic regimens recommended for treatment of a disease, disorder, or condition associated with angiogenesis. To give but a few examples, recommended regimens for treatment of cancer can be found at <www.cancer.gov>, the website of the National Cancer Institute. Recommended regimens for treatment of macular degeneration can be found at <www.mayoclinic.org/macular-degeneration/treatment.html>. Treatment regimens may include chemotherapy, surgery, and/or radiation therapy.

EXAMPLES

Example 1

Synthesis of Reduced Lysine Chlorotoxin Polypeptides

Reduced lysine chlorotoxin polypeptides having amino acid sequences of SEQ ID NOs. 1-28 as shown in Table 1 and Table 2 can be synthesized using solid phase peptide synthesis (SPPS). Small, solid, and porous beads are treated with linkers through which the synthesized polypeptide is covalently attached to the beads during synthesis. Nascent polypeptides are consequently immobilized on the solid-phase and retained during washing steps.

Repeated cycles of coupling and deprotection are used to generate polypeptides having sequences of SEQ ID NOs: 1-28. In each cycle of coupling and deprotection, the free N-terminal amine of a peptide or polypeptide attached to the solid phase is coupled to a single amino acid unit that is protected at its N-terminus by an Fmoc (9H-(f)luoren-9-yl (m)eth(o)xy(c)arbonyl) protecting group. This unit on the growing peptide/polypeptide chain is then deprotected in basic conditions such as 20% piperidine in dimethylformamide to generate a new N-terminal amine that can be attached to a further amino acid in the next round of coupling-deprotection.

After all cycles have been completed as desired, the polypeptide is cleaved from the bead using trifluoroacetic acid.

To generate additional reduced lysine chlorotoxin polypeptides, polypeptides having amino acid sequences of SEQ ID NOS: 1, 11, 12 and 13 are modified by pegylation at lysines according to Table 2.

Example 2

Assays for Binding Activity of Reduced Lysine Chlorotoxin Polypeptides

Chlorotoxin has been shown to bind selectively to many different tumor types including U251 glioma cells and PC3 prostate cancer cells. In the present Example, reduced lysine chlorotoxin polypeptides generated as described in Example 2 are labeled with biotin and assayed for binding activity. Each biotinylated reduced lysine chlorotoxin polypeptide is incubated with U251 glioma cells and separately with PC3 prostate cancer cells obtained from subconfluent cell cultures. After incubation, cells are stained with avidin-HRP (horse-radish peroxidase) using a commercial kit according to manufacturer's instructions. Chlorotoxin is used as a positive staining control, and an incubation reaction with no polypeptide is used as a negative staining control. A peptide with an amino acid sequence that is scrambled as compared to that of chlorotoxin may also be used as a negative staining control. Positive staining as evidenced by presence of a colored reaction product of HRP is used as an indication of binding by the biotinylated reduced lysine chlorotoxin polypeptide.

Reduced lysine chlorotoxin polypeptides that exhibit binding to U251 or PC3 cells are then tested (in labeled form) in competitive binding assays in which un-labeled chlorotoxin is used as a competitor. Reduced lysine chlorotoxin polypeptides that exhibit decreasing levels of binding in the presence of increasing amounts of chlorotoxin are identified.

To quantitate percentage of cells bound, avidin coupled to a fluorescent dye such as FITC or Texas Red is used instead of avidin-HRP to stain cells after incubation with biotinylated polypeptides, and cells are analyzed by FACS (fluorescence-activated cell sorting).

Example 3

Additional Assays for Binding Activity of Reduced Lysine Chlorotoxin Polypeptides Reduced lysine chlorotoxin polypeptides identified as binding competitively with chlorotoxin to U251 and/or PC3 in Example 2 cells are further assayed for binding activity to a wider range of cell types, in order to obtain a more comprehensive binding profile.

Table 3 lists cell lines and primary cultured cells, any or any combination of which may be tested in binding assays with reduced lysine chlorotoxin polypeptides. Cell lines and primary cultured cells listed in table 3 include both glioma and non-glioma cell lines from human, rat, and mouse.

TABLE 3

| Primary Cells and Tumor Cell Lines to which binding may be tested |
|---|
| Human Glioma Cell Lines |
| D54-MG |
| U251-MG |
| CH235 |
| STTG1 |
| U138-MG |
| U87-MG |
| U373-MG |
| T98G |
| A172 |
| G26 |
| Other Glioma Cell Lines |
| C6 rat |
| 9L rat |
| GL2g1 mouse |
| Primary cells |
| Rat primary normal cortical and spinal cord astrocyte cultures |
| Human primary glioma cultures |
| Human normal astrocyte cultures |
| Human normal fibroblast cultures |
| Human umbilical vascular endothelial cells (HUVEC) |
| Non-Glioma Cell Lines |
| SH-SY5Y human neuroblastoma |
| SH-N-MC human neuroblastoma |
| HCN-2 human neuronal |
| PFSK-1 human primitive neuroectodermal |
| HT 29 human colon carcinoma |
| COS-2 monkey kidney cell line |
| BALBc 3T3 mouse fibroblast cell line |
| HEK 293 human epithelial kidney |
| NIH 3T3 mouse fibroblast cell line |
| CCD19lu human lung fibroblast |
| H460 human lung fibroblast |
| A549 human lung |
| A-427 human lung carcinoma |
| W-62 human lung cancer |
| NIH-H1466 human lung adenocarcinoma |
| 1299 human non-small cell lung cell line |
| Caco-2 human colon carcinoma |
| HCT116 human colon carcinoma |
| SW948 human colorectal adenocarcinoma |
| DU 145 human prostate cancer |
| PC-3 human prostate cancer |
| LNCaP human prostate cancer |
| 2LMP human metastatic breast cancer |

TABLE 3-continued

| Primary Cells and Tumor Cell Lines to which binding may be tested |
|---|
| MDA-MB-453 human breast cancer |
| DY3672 human breast cancer |
| HeLa human cervix carcinoma |
| LCC6 human breast cancer |
| HCN-2 human neuronal cell line |
| BT474 human breast carcinoma |
| CCD986Sk human skin fibroblast |
| SK-BR-3 human breast adenocarcinoma |
| MCSF-7 human breast cancer |
| MDA-MB-231 human breast adenocarcinoma |
| MDA-MB-468 human breast adenocarcinoma |
| CHO Chinese hamster ovary |
| SKMEL-31 human melanoma |
| SKMEL-28 human melanoma |
| Malme 3M human metastastic melanoma |
| Panc-1 human pancreatic cancer |
| PaCa-2 human pancreatic cancer |
| HepG2 human hepatic carcinoma |
| Caki-1 human clear cell renal carcinoma |
| ACHN human renal cell adenocarcinoma |
| Raji human lymphoma |
| Daudi human lymphoma |
| MOLT4 human leukemia |
| HL60 human acute promyelocytic leukemia |

Example 4

Conjugation of Monolsyine Chlorotoxin Polypeptides to Paclitaxel

One or more monolysine chlorotoxin polypeptides synthesized in Example 1 and optionally assayed for finding in Examples 2 and/or 3 is/are conjugated to paclitaxel, which by itself is a water insoluble anti-cancer therapeutic agent. Paclitaxel is a mitotic inhibitor.

Reduced lysine chlorotoxin polypeptides are reacted with a paclitaxel-ester-linker carboxy entity (e.g., NHS/EEDQ) in PBS and incubated. Samples from the purified final product are analyzed by high performance liquid chromatography (HPLC) and mass spectrometry (MS) to confirm that single species conjugates are generated. Resulting conjugates are tested for water solubility by determining the saturation concentration and rate of solution. Conjugates that are water soluble are identified for further analysis as drug candidates.

Example 5

Conjugation of Reduced Lysine Chlorotoxin Polypeptides to Gemcitabine

Reduced lysine chlorotoxin polypeptides that have no lysine residues at all (see, e.g., SEQ ID NOs: 2, 5 and 6) are synthesized as described in Example 1 and optionally assayed for binding in Examples 2 and/or 3. The reduced lysine chlorotoxin polypeptides are conjugated to gemcitabine (Gemzar™), a nucleoside analog, via the N-terminus.

Example 6

In Vitro Binding Assay of Chlorotoxin Conjugates

Chlorotoxin conjugates from Examples 4 and 5 can be individually tested for binding to tumor cell lines as described for reduced lysine chlorotoxin polypeptides, as described in Examples 2 and 3.

Example 7

In Vitro Cytotoxicity Assay of Chlorotoxin Conjugates

Chlorotoxin conjugates obtained from Examples 4 and 5 and optionally tested for binding as described in Example 6 are tested for cytotoxicity in one or more cell lines listed in Table 3. Cells in culture are exposed to chlorotoxin conjugates by incubating in varying concentrations of chlorotoxin conjugate. After 1.5 hours of exposure, cell viability is measured and a plot of the percentage of viable cells versus molar concentration of chlorotoxin conjugate is calculated. For comparison, cells are separately incubated with cytotoxic agent alone (e.g., paclitaxel from Example 4 or temozolomide from Example 5) and a similar dose-response curve for viability is calculated.

Example 8

In Vivo Uptake of Chlorotoxin Conjugates

In vivo uptake of chlorotoxin conjugates of the present invention can be assessed by imaging using in situ radiolabeled peptide (labeled with $^{13}$C, $^{2}$H, or $^{15}$N, etc.) and/or radiolabeled entity/moiety; nanoparticles and magnetic resonance imaging; and/or near infrared dyes and biophotonicimagine. Anti-chlorotoxin polypeptide antibodies may also be used to detect uptake in tissues.

Example 9

Biological Activity of Reduced Lysine Chlorotoxin Polypeptides to Inhibit Cell Invasion Reduced lysine chlorotoxin polypeptides (or conjugates thereof) are tested for ability to inhibit invasion of tumor cells using a Trans-well migration assay. In this assay, tumor cells are plated on the upper chamber of the trans-well with or without the reduced lysine chlorotoxin polypeptide (or conjugates thereof) and migration of the cells is stimulated with a growth factor such as VEGF or PDGF. After approximately 24 hours of incubation in cell culture media, non-migrating cells remaining on the upper side of the trans-well filter are removed and migrated cells on the lower side are stained for visualization. Migrated cells are counted as an index of invasion. Modified chlorotoxin variants that have similar biological activity to chlorotoxin are considered to retain functional activity.

Example 10

Chlorotoxin Conjugates in In Vivo Breast Cancer Tumor Model

Therapeutic activity of chlorotoxin conjugates is tested in an in vivo breast cancer model. In this example, a mouse tumor model created by xenografting MDA-MB-468 breast cancer cells into recipient mice is used to test for effects of paclitaxel-chlorotoxin conjugates generated in Examples 4 on tumor growth.

Mice bearing flank tumors are injected intravenously at a paclitaxel dose of 3.7 mg/kg three times per week for a total of 8 doses. The concentration of conjugate being used in these experiments is "sub-therapeutic" in that the same dosing regimen using non-conjugated paclitaxel is not enough to have a therapeutic effect. A group of mice is injected with saline alone as a control. Another group of mice is injected with paclitaxel at a dose of 3.7 mg/kg. Tumor growth is monitored using calipers to measure the length and width of the tumor during and after the treatment interval. Tumor growth over time is plotted as percent of original tumor size versus time.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

---

The invention claimed is:

1. A method for imaging a tissue imagable by chlorotoxin, the method comprising the step of:
contacting the tissue imagable by chlorotoxin with a chlorotoxin conjugate to image the tissue,
wherein the chlorotoxin conjugate comprises a modified chlorotoxin peptide having at least 90% sequence identity with SEQ ID NO: 1,
and wherein the modified chlorotoxin peptide comprises a single lysine residue and is covalently coupled to an imaging agent.

2. A method for detecting cancer detectable by chlorotoxin, the method comprising the step of:
contacting the cancer tissue detectable by chlorotoxin with a chlorotoxin conjugate to detect the cancer tissue,
wherein the chlorotoxin conjugate comprises a modified chlorotoxin peptide having at least 90% sequence identity with SEQ ID NO: 1,
and wherein the modified chlorotoxin peptide comprises a single lysine residue and is covalently coupled to a detectable agent.

3. The method of claim 1 or claim 2, wherein the single lysine residue is at a position corresponding to position 27 of SEQ ID NO: 1.

4. The method of claim 3, wherein Lys 15 and Lys 23 of the modified chlorotoxin peptide are substituted by an amino acid independently selected from the group consisting of natural and unnatural amino acids.

5. The method of claim 4, wherein Lys 15 and Lys 23 of the modified chlorotoxin peptide are substituted by alanine.

6. The method of claim 4, wherein Lys 15 and Lys 23 of the modified chlorotoxin peptide are substituted by arginine.

7. The method of claim 4, wherein Lys 15 of the modified chlorotoxin peptide is substituted by alanine and Lys 23 of the modified chlorotoxin peptide is substituted by arginine.

8. The method of claim 4, wherein Lys 15 of the modified chlorotoxin peptide is substituted by arginine and Lys 23 of the modified chlorotoxin peptide is substituted by alanine.

9. The method of claim 1 or claim 2, wherein the single lysine residue is at a position corresponding to position 15 of SEQ ID NO: 1.

10. The method of claim 1 or claim 2, wherein the single lysine residue is at a position corresponding to position 23 of SEQ ID NO: 1.

11. The method of claim 1, wherein the imaging agent is selected from the group consisting of a fluorescent label, a radioactive or paramagnetic isotope or ion, a ligand, a chemiluminescent agent, a bioluminescent agent, a photosensitizer, a quantum dot, a microparticle, a metal nanoparticle, a nanocluster, an enzyme, a colorimetric label, a hapten, a molecular beacon, an aptamer beacon, biotin, and dioxigenin.

12. The method of claim 11, wherein the imaging agent comprises a fluorescent label.

13. The method of claim 11, wherein the imaging agent comprises a radioactive isotope.

14. The method of claim 11, wherein the imaging agent comprises a paramagnetic isotope or ion.

15. The method of claim 11, wherein the imaging agent comprises a chemiluminescent agent selected from the group consisting of an acridinum ester and a stabilized dioxetane.

16. The method of claim 11, wherein the imaging agent comprises a photosensitizer selected from the group consisting of porphyrins, porphyrin derivatives, metalloporphyrins, metallophthalocyanines, angelicins, chalcogenapyrrillium dyes, chlorophylls, flavins, alloxazine, fullerenes, pheophorbides, pyropheophorbides, pheophytins, sapphyrins, texaphyrins, purpurins, porphycenes, phenothiaziniums, methylene blue derivatives, naphthalimides, nile blue derivatives, quinones, perylenequinones, psoralens, retinoids, thiophenes, verdins, xanthene dyes, dimeric porphyrins, oligomeric porphyrins, and 5-aminolevulinic acid.

17. The method of claim 11, wherein the imaging agent comprises a metal nanoparticle selected from the group consisting of a gold nanoparticle, a silver nanoparticle, a copper nanoparticle, and a platinum nanoparticle.

18. The method of claim 11, wherein the imaging agent comprises a colorimetic label selected from the group consisting of a dye and colloidal gold.

19. The method of claim 11, wherein the imaging agent comprises a radioactive or paramagnetic isotope selected from the group consisting of an isotope of hydrogen, an isotope of carbon, an isotope of fluorine, an isotope of phosphorous, an isotope of copper, an isotope of gallium, an isotope of yttrium, an isotope of technetium, an isotope of indium, an isotope of iodine, an isotope of rhenium, an isotope of thallium, an isotope of bismuth, an isotope of astatine, an isotope of samarium, and an isotope of lutetium.

20. The method of claim 11, wherein the imaging agent comprises a radioactive or paramagnetic isotope or ion selected from the group consisting of $^{3}H$, $^{13}C$, $^{14}C$, $^{18}F$, $^{32}P$, $^{35}S$, $^{64}Cu$, $^{67}Ga$, $^{90}Y$, $^{99M}Tc$, $^{111}In$, $^{125}I$, $^{123}I$, $^{129}I$, $^{131}I$, $^{135}I$, $^{186}Re$, $^{187}Re$, $^{201}Tl$, $^{212}Bi$, $^{211}At$, $^{153}Sm$, and $^{177}Lu$.

21. The method of claim 11, wherein the imaging agent comprises a radioactive or paramagnetic isotope or ion selected from the group consisting of iodine-131 ($^{131}I$), iodine-125 ($^{125}I$), bismuth-212 ($^{212}Bi$), bismuth-213 ($^{213}Bi$), astatine-221 ($^{221}At$), copper-67 ($^{67}Cu$), copper-64 ($^{64}Cu$), rhenium-186 ($^{186}Re$), rhenium-188 ($^{188}Re$), phosphorus-32 ($^{32}P$), samarium-153 ($^{153}Sm$), technetium-99m ($^{99m}Tc$), gallium-67 ($^{67}Ga$), and thallium-201 ($^{201}Tl$).

22. The method of claim 11, wherein the imaging agent comprises a radioactive or paramagnetic isotope or ion selected from a group consisting of gadolinium III (Gd3+), chromium III (Cr3+), dysprosium III (Dy3+), iron III (Fe3+), manganese II (Mn2+), and ytterbium III (Yb3+).

23. The method of claim 11, wherein the imaging agent comprises a radioactive or paramagnetic isotope or ion selected from a group consisting of carbon-13 ($^{13}C$) and fluorine-19 ($^{19}F$).

24. The method of claim 11, wherein the imaging agent comprises an isotope of lutetium (Lu).

25. The method of claim 24, wherein the isotope of lutetium (Lu) comprises lutetium-177 ($^{177}Lu$).

26. The method of claim 11, wherein the imaging agent comprises an isotope of indium (In).

27. The method of claim 26, wherein the isotope of indium (In) comprises indium-111 ($^{111}In$).

28. The method of claim 11, wherein the imaging agent comprises a fluorescent label selected from the group consisting of a fluorescein dye, a rhodamine dye, a coumarin dye, a cyanine dye, a styryl dye, an oxonol dye, a carbocyanine, merocyanine, phycoerythrin, erythrosin, and eosin.

29. The method of claim 28, wherein the fluorescent label comprises a fluorescein dye selected from the group consisting of fluorescein, fluorescein isothiocyanine, naphthofluorescein, 4',5'-dichloro-2',7'-dimethoxyfluorescein, and 6-carboxyfluorescein.

30. The method of claim 28, wherein the fluorescent label comprises a rhodamine dye selected from the group consisting of carboxytetramethyl-rhodamine, carboxyrhodamine 6G, carboxy-X-rhodamine, lissamine rhodamine B, rhodamine 6G, rhodamine Green, rhodamine Red, and tetramethylrhodamine.

31. The method of claim 28, wherein the fluorescent label comprises a coumarin dye selected from the group consisting of coumarin, methoxycoumarin, dialkylaminocoumarin, hydroxycoumarin, and aminomethylcoumarin.

32. The method of claim 11, wherein the imaging agent comprises an enzyme selected from the group consisting of horseradish peroxidase, beta-galactosidase, luciferase, alkaline phosphatase, beta-glucuronidase, beta-D-glucosidase, urease, and glucose oxidase.

33. The method of claim 1, wherein the imaging agent comprises a boron nanoparticle, a boron and carbon nanoparticle, a boron carbide nanoparticle, a boron-containing polymer, a boron and carbon containing polymer, a boron carbide polymer, or any of these nanoparticles or polymers further comprising gadolinium.

34. The method of claim 1, wherein the imaging agent is imagable by magnetic resonance imaging (MRI), nuclear magnetic resonance spectroscopy (MRS), single photon emission computed tomography (SPECT), gamma camera imaging, or position emission tomography (PET).

35. The method of claim 1, wherein the imaging agent is imagable by spectroscopic, photochemical, biochemical, immunochemical, electrical, optical, or chemical detection or imaging.

36. The method of claim 1, wherein the imaging agent is covalently coupled to the modified chlorotoxin peptide through the single lysine residue.

37. The method of claim 1, wherein the modified chlorotoxin peptide is further covalently coupled to a targeting agent.

38. The method of claim 1, wherein the modified chlorotoxin peptide is further covalently coupled to a diagnostic agent.

39. The method of claim 1, wherein the modified chlorotoxin peptide is further covalently coupled to a therapeutic agent.

40. The method of claim 39, wherein the therapeutic agent is selected from the group consisting of methotrexate, docetaxel, cisplatin, etoposide, paclitaxel, a single-stranded deoxyribonucleic acid (ssDNA), a double-stranded deoxyribonucleic acid (dsDNA), a short interfering ribonucleic acid (siRNA), a short hairpin ribonucleic acid (shRNA), and a ribonucleic acid that mediates ribonucleic acid interference (RNAi).

41. The method of claim 11, wherein the imaging agent comprises riboflavin.

42. The method of claim 2, wherein the detectable agent is selected from the group consisting of a fluorescent label, a radioactive or paramagnetic isotope or ion, a ligand, a chemiluminescent agent, a bioluminescent agent, a photosensitizer, a quantum dot, a microparticle, a metal nanoparticle, a nanocluster, an enzyme, a colorimetric label, a hapten, a molecular beacon, an aptamer beacon, biotin, and dioxigenin.

43. The method of claim 42, wherein the detectable agent comprises a fluorescent label.

44. The method of claim 42, wherein the detectable agent comprises a radioactive isotope.

45. The method of claim 42, wherein the detectable agent comprises a paramagnetic isotope or ion.

46. The method of claim 42, wherein the detectable agent comprises a chemiluminescent agent selected from the group consisting of an acridinum ester and a stabilized dioxetane.

47. The method of claim 42, wherein the detectable agent comprises a photosensitizer selected from the group consisting of porphyrins, porphyrin derivatives, metalloporphyrins, metallophthalocyanines, angelicins, chalcogenapyrrillium dyes, chlorophylls, flavins, alloxazine, fullerenes, pheophorbides, pyropheophorbides, pheophytins, sapphyrins, texaphyrins, purpurins, porphycenes, phenothiaziniums, methylene blue derivatives, naphthalimides, nile blue derivatives, quinones, perylenequinones, psoralens, retinoids, thiophenes, verdins, xanthene dyes, dimeric porphyrins, oligomeric porphyrins, and 5-aminolevulinic acid.

48. The method of claim 42, wherein the detectable agent comprises a metal nanoparticle selected from the group consisting of a gold nanoparticle, a silver nanoparticle, a copper nanoparticle, and a platinum nanoparticle.

49. The method of claim 42, wherein the detectable agent comprises a colorimetic label selected from the group consisting of a dye and colloidal gold.

50. The method of claim 42, wherein the detectable agent comprises a radioactive or paramagnetic isotope selected from the group consisting of an isotope of hydrogen, an isotope of carbon, an isotope of fluorine, an isotope of phosphorous, an isotope of copper, an isotope of gallium, an isotope of yttrium, an isotope of technetium, an isotope of indium, an isotope of iodine, an isotope of rhenium, an isotope of thallium, an isotope of bismuth, an isotope of astatine, an isotope of samarium, and an isotope of lutetium.

51. The method of claim 42, wherein the detectable agent comprises a radioactive or paramagnetic isotope or ion selected from the group consisting of $^{3}$H, $^{13}$C, $^{14}$C, $^{18}$F, $^{32}$P, $^{35}$S, $^{64}$Cu, $^{67}$Ga, $^{90}$Y, $^{99m}$Tc, $^{111}$In, $^{125}$I, $^{123}$I, $^{129}$I, $^{131}$I, $^{135}$I, $^{186}$Re, $^{187}$Re, $^{201}$Tl, $^{212}$Bi, $^{211}$At, $^{153}$Sm, and $^{177}$Lu.

52. The method of claim 42, wherein the detectable agent comprises a radioactive or paramagnetic isotope or ion selected from the group consisting of iodine-131 ($^{131}$I), iodine-125 ($^{125}$I), bismuth-212 ($^{212}$Bi), bismuth-213 ($^{213}$Bi), astatine-221 ($^{221}$At), copper-67 ($^{67}$Cu), copper-64 ($^{64}$Cu), rhenium-186 ($^{186}$Re), rhenium-188 ($^{188}$Re), phosphorus-32 ($^{32}$P), samarium-153 ($^{153}$Sm), technetium-99m ($^{99m}$Tc), gallium-67 ($^{67}$Ga), and thallium-201 ($^{201}$Tl).

53. The method of claim 42, wherein the detectable agent comprises a radioactive or paramagnetic isotope or ion selected from a group consisting of gadolinium III (Gd3+), chromium III (Cr3+), dysprosium III (Dy3+), iron III (Fe3+), manganese II (Mn2+), and ytterbium III (Yb3+).

54. The method of claim 42, wherein the detectable agent comprises a radioactive or paramagnetic isotope or ion selected from a group consisting of carbon-13 ($^{13}$C) and fluorine-19 ($^{19}$F).

55. The method of claim 42, wherein the detectable agent comprises an isotope of lutetium (Lu).

56. The method of claim 55, wherein the isotope of lutetium (Lu) comprises lutetium-177 ($^{177}$Lu).

57. The method of claim 42, wherein the detectable agent comprises an isotope of indium (In).

58. The method of claim 57, wherein the isotope of indium (In) comprises indium-111 ($^{111}$In).

59. The method of claim 42, wherein the detectable agent comprises a fluorescent label selected from the group consisting of a fluorescein dye, a rhodamine dye, a coumarin dye, a cyanine dye, a styryl dye, an oxonol dye, a carbocyanine, merocyanine, phycoerythrin, erythrosin, and eosin.

60. The method of claim 59, wherein the fluorescent label comprises a fluorescein dye selected from the group consisting of fluorescein, fluorescein isothiocyanine, naphthofluorescein, 4',5'-dichloro-2',7'-dimethoxyfluorescein, and 6-carboxyfluorescein.

61. The method of claim 59, wherein the fluorescent label comprises a rhodamine dye selected from the group consisting of carboxytetramethyl-rhodamine, carboxyrhodamine 6G, carboxy-X-rhodamine, lissamine rhodamine B, rhodamine 6G, rhodamine Green, rhodamine Red, and tetramethylrhodamine.

62. The method of claim 59, wherein the fluorescent label comprises a coumarin dye selected from the group consisting of coumarin, methoxycoumarin, dialkylaminocoumarin, hydroxycoumarin, and aminomethylcoumarin.

63. The method of claim 42, wherein the detectable agent comprises an enzyme selected from the group consisting of horseradish peroxidase, beta-galactosidase, luciferase, alkaline phosphatase, beta-glucuronidase, beta-D-glucosidase, urease, and glucose oxidase.

64. The method of claim 2, wherein the detectable agent comprises a boron nanoparticle, a boron and carbon nanoparticle, a boron carbide nanoparticle, a boron-containing polymer, a boron and carbon containing polymer, a boron carbide polymer, or any of these nanoparticles or polymers further comprising gadolinium.

65. The method of claim 2, wherein the detectable agent is detectable by magnetic resonance imaging (MRI), nuclear magnetic resonance spectroscopy (MRS), single photon emission computed tomography (SPECT), gamma camera imaging, or position emission tomography (PET).

66. The method of claim 2, wherein the detectable agent is detectable by spectroscopic, photochemical, biochemical, immunochemical, electrical, optical, or chemical detection or imaging.

67. The method of claim 2, wherein the detectable agent is covalently coupled to the modified chlorotoxin peptide through the single lysine residue.

68. The method of claim 2, wherein the modified chlorotoxin peptide is further covalently coupled to a targeting agent.

69. The method of claim 2, wherein the modified chlorotoxin peptide is further covalently coupled to a diagnostic agent.

70. The method of claim 2, wherein the modified chlorotoxin peptide is further covalently coupled to a therapeutic agent.

71. The method of claim 70, wherein the therapeutic agent is selected from the group consisting of methotrexate, docetaxel, cisplatin, etoposide, paclitaxel, a single-stranded deoxyribonucleic acid (ssDNA), a double-stranded deoxyribonucleic acid (dsDNA), a short interfering ribonucleic acid (siRNA), a short hairpin ribonucleic acid (shRNA), and a ribonucleic acid that mediates ribonucleic acid interference (RNAi).

72. The method of claim 42, wherein the detectable agent comprises riboflavin.

* * * * *

SEQUENCE LISTING

```
<160> NUMBER OF SEQ ID NOS: 29

<210> SEQ ID NO 1
<211> LENGTH: 36
<212> TYPE: PRT
<213> ORGANISM: Leiurus quinquestriatus

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 2

Met Cys Met Pro Cys Phe Thr Thr Asp His Gln Met Ala Arg Cys Asp
1               5                   10                  15

Asp Cys Cys Gly Gly Gly Arg Gly Cys Tyr Gly Pro Gln Cys Leu Cys
            20                  25                  30

Arg

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Met Cys Met Pro Cys Phe Thr Thr Asp His Gln Met Ala Arg Cys
1               5                   10                  15

Asp Asp Cys Cys Gly Gly Gly Arg Gly Cys Tyr Gly Pro Gln Cys Leu
            20                  25                  30

Cys Arg

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Cys Met Pro Cys Phe Thr Thr Asp His Gln Met Ala Arg Cys Asp
1               5                   10                  15

Asp Cys Cys Gly Gly Gly Arg Gly Cys Tyr Gly Pro Gln Cys Leu Cys
            20                  25                  30

Arg Lys

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Cys Met Pro Cys Phe Thr Thr Asp His Gln Met Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg
        35

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Met Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Met Cys Met Pro Cys Phe Thr Thr Asp His Gln Met Ala Arg Ala
1               5                   10                  15

Cys Asp Asp Cys Cys Gly Gly Ala Gly Arg Gly Ala Cys Tyr Gly Pro
            20                  25                  30

Gln Cys Leu Cys Arg
        35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Lys Met Cys Met Pro Cys Phe Thr Thr Asp His Gln Met Ala Arg Arg
1               5                   10                  15

Cys Asp Asp Cys Cys Gly Gly Arg Gly Arg Gly Arg Cys Tyr Gly Pro
            20                  25                  30

Gln Cys Leu Cys Arg
        35

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Cys Met Pro Cys Phe Thr Thr Asp His Gln Met Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg Lys
        35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 10

Met Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg Lys
        35

<210> SEQ ID NO 11
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Cys Met Pro Cys Phe Thr Thr Asp His Gln Met Ala Arg Cys Asp
1               5                   10                  15

Asp Cys Cys Gly Gly Lys Gly Arg Gly Lys Cys Tyr Gly Pro Gln Cys
            20                  25                  30

Leu Cys Arg
        35

<210> SEQ ID NO 12
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Cys Met Pro Cys Phe Thr Thr Asp His Gln Met Ala Arg Lys Cys
1               5                   10                  15

Asp Asp Cys Cys Gly Gly Gly Arg Gly Lys Cys Tyr Gly Pro Gln Cys
            20                  25                  30

Leu Cys Arg
        35

<210> SEQ ID NO 13
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Cys Met Pro Cys Phe Thr Thr Asp His Gln Met Ala Arg Lys Cys
1               5                   10                  15

Asp Asp Cys Cys Gly Gly Lys Gly Arg Gly Cys Tyr Gly Pro Gln Cys
            20                  25                  30

Leu Cys Arg
        35

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Cys Met Pro Cys Phe Thr Thr Asp His Gln Met Ala Arg Cys Asp
1               5                   10                  15

Asp Cys Cys Gly Gly Gly Arg Gly Lys Cys Tyr Gly Pro Gln Cys Leu
            20                  25                  30

Cys Arg

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Cys Met Pro Cys Phe Thr Thr Asp His Gln Met Ala Arg Cys Asp
1               5                   10                  15

Asp Cys Cys Gly Gly Lys Gly Arg Gly Cys Tyr Gly Pro Gln Cys Leu
            20                  25                  30

Cys Arg

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Cys Met Pro Cys Phe Thr Thr Asp His Gln Met Ala Arg Lys Cys
1               5                   10                  15

Asp Asp Cys Cys Gly Gly Gly Arg Gly Cys Tyr Gly Pro Gln Cys Leu
            20                  25                  30

Cys Arg

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Cys Met Pro Cys Phe Thr Thr Asp His Gln Met Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Cys Met Pro Cys Phe Thr Thr Asp His Gln Met Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35
```

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Cys Met Pro Cys Phe Thr Thr Asp His Gln Met Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35
```

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Cys Met Pro Cys Phe Thr Thr Asp His Gln Met Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35
```

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Cys Met Pro Cys Phe Thr Thr Asp His Gln Met Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35
```

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 22

Met Cys Met Pro Cys Phe Thr Thr Asp His Gln Met Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Cys Met Pro Cys Phe Thr Thr Asp His Gln Met Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Cys Met Pro Cys Phe Thr Thr Asp His Gln Met Ala Arg Cys Asp
1               5                   10                  15

Asp Cys Cys Gly Gly Ala Gly Arg Gly Ala Cys Tyr Gly Pro Gln Cys
            20                  25                  30

Leu Cys Arg
        35

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Cys Met Pro Cys Phe Thr Thr Asp His Gln Met Ala Arg Ala Cys
1               5                   10                  15

Asp Asp Cys Cys Gly Gly Gly Arg Gly Ala Cys Tyr Gly Pro Gln Cys
            20                  25                  30

Leu Cys Arg
        35

<210> SEQ ID NO 26
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

Met Cys Met Pro Cys Phe Thr Thr Asp His Gln Met Ala Arg Arg Cys
1               5                   10                  15

Asp Asp Cys Cys Gly Gly Arg Gly Arg Gly Cys Tyr Gly Pro Gln Cys
                20                  25                  30

Leu Cys Arg
        35

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Met Cys Met Pro Cys Phe Thr Thr Asp His Gln Met Ala Arg Lys
1               5                   10                  15

Cys Asp Asp Cys Cys Gly Gly Lys Gly Arg Gly Lys Cys Tyr Gly Pro
                20                  25                  30

Gln Cys Leu Cys Arg
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
                20                  25                  30

Cys Leu Cys Arg Lys
        35

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Thr Asp His Gln Met Ala Arg
1               5